United States Patent
Hayashi et al.

(10) Patent No.: US 8,080,066 B2
(45) Date of Patent: Dec. 20, 2011

(54) AZO COMPOUNDS, AZO PIGMENTS, AND DISPERSION, COLORING COMPOSITION AND INK FOR INKJET RECORDING CONTAINING THE AZO COMPOUNDS OR AZO PIGMENTS, INK TANK FOR INKJET RECORDING, INKJET RECORDING METHOD, AND RECORDED PRODUCTS

(75) Inventors: Shinya Hayashi, Shizuoka (JP); Keiichi Tateishi, Shizuoka (JP); Naoyuki Hanaki, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/921,327

(22) PCT Filed: Mar. 5, 2009

(86) PCT No.: PCT/JP2009/054178
§ 371 (c)(1),
(2), (4) Date: Sep. 7, 2010

(87) PCT Pub. No.: WO2009/110555
PCT Pub. Date: Sep. 11, 2009

(65) Prior Publication Data
US 2011/0018946 A1  Jan. 27, 2011

(30) Foreign Application Priority Data

Mar. 7, 2008 (JP) ................. 2008-058712
Dec. 26, 2008 (JP) ................. 2008-334956

(51) Int. Cl.
*A61Q 5/10* (2006.01)
*C09D 11/00* (2006.01)

(52) U.S. Cl. ...... 8/637.1; 8/639; 8/690; 8/692; 106/31.6
(58) Field of Classification Search .............. 8/637.1, 8/639, 690, 692; 106/31.6
See application file for complete search history.

(56) References Cited

U.S. PATENT DOCUMENTS 2,936,306 A  5/1960  Schmid et al.
(Continued)

FOREIGN PATENT DOCUMENTS

EP  1906401 A2  4/2008
(Continued)

OTHER PUBLICATIONS

STIC Seach Report dated Jun. 9, 2010.*
(Continued)

*Primary Examiner* — Eisa Elhilo
(74) *Attorney, Agent, or Firm* — Sughrue Mion, PLLC

(57) ABSTRACT

An azo pigment represented by the general formula (1), a tautomer, salt, or hydrate thereof:

General formula (1)

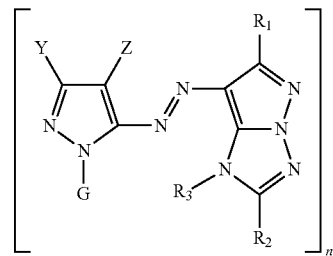

wherein
$R_1$, $R_2$, $R_3$, Y, Z, and G each independently represents a hydrogen atom or a substituent, n represents an integer of from 2 to 4 and, when n=2, the general formula (1) represents a dimer formed through $R_1$, $R_2$, $R_3$, Y, Z, or G and, when n=3, the general formula (1) represents a trimer formed through $R_1$, $R_2$, $R_3$, Y, Z, or G and, when n=4, the general formula (1) represents a tetramer formed through $R_1$, $R_2$, $R_3$, Y, Z, or G.

18 Claims, 6 Drawing Sheets

U.S. PATENT DOCUMENTS

2005/0126431 A1  6/2005  Potenza et al.

FOREIGN PATENT DOCUMENTS

| JP | 56-38354 A | | 4/1987 |
| --- | --- | --- | --- |
| JP | 11-100519 A | | 4/1999 |
| JP | 2003-277662 A | | 10/2003 |
| JP | 2005-162812 A | | 6/2005 |
| JP | 20051622812 | * | 6/2005 |
| JP | 2005-220217 A | | 8/2005 |
| JP | 2008-007732 A | | 1/2008 |

OTHER PUBLICATIONS

International Search Report dated Jun. 2, 2009 issued in counterpart Application No. PCT/JP2009/054178.

Written Opinion (PCT/ISA/237) for PCT/JP2009/054178, dated Jun. 2, 2009.

Extended European Search Report issued on Oct. 4, 2011 in the corresponding European Patent Application No. 09716401.6 English.

* cited by examiner

US 8,080,066 B2

AZO COMPOUNDS, AZO PIGMENTS, AND DISPERSION, COLORING COMPOSITION AND INK FOR INKJET RECORDING CONTAINING THE AZO COMPOUNDS OR AZO PIGMENTS, INK TANK FOR INKJET RECORDING, INKJET RECORDING METHOD, AND RECORDED PRODUCTS

TECHNICAL FIELD

The present invention relates to azo compounds, azo pigments, and a dispersion, coloring composition and ink for inkjet recording containing the azo compound or the azo pigment, an ink tank for inkjet recording, an inkjet recording method, and recorded products.

BACKGROUND ART

In recent years, as image-recording materials, materials for forming color images have been predominant and, specifically, recording materials for an ink jet system, recording materials for a thermal transfer system, recording materials for an electro-photographic system, transfer type silver halide light-sensitive materials, printing inks, and recording pens have found widespread use. Also, in photographing devices such as CCDs for photographing equipment, and in LCDs and PDPs for display, color filters are used for recording or reproducing a color image. In these color image recording materials and color filters, colorants (dyes or pigments) of three primary colors of a so-called additive color mixing process or subtractive color mixing process have been used in order to display or record full-color images. In actuality, however, there is no fast colorant having the absorption characteristics capable of realizing a preferred color reproduction region and resisting various use conditions and environmental conditions. Thus, the improvement thereof has strongly been desired.

Dyes or pigments to be used for the above-mentioned uses are required to have in common the following properties. That is, they are required to have absorption characteristics favorable in view of color reproduction and have good fastness under the conditions of the environment wherein they are used, for example, fastness against light, heat, and an oxidative gas such as ozone. In addition, in the case where the colorant is a pigment, the pigment is further required to be substantially insoluble in water or in an organic solvent, to have a good fastness to chemicals, and not to lose the preferred absorption characteristics it shows in a molecularly dispersed state even when used as particles. Although the required properties described above can be controlled by adjusting the intensity of intermolecular interaction, both of them are in a trade-off relation with each other, thus being difficult to allow them to be compatible with each other. Besides, in the case of using a pigment as the colorant, the pigment is additionally required to have a particle size and a particle shape necessary for realizing desired transparency, to have good fastness under the conditions of the environment wherein they are used, for example, fastness against light, heat, and an oxidative gas such as ozone, to have good fastness to an organic solvent and chemicals such as a sulfurous acid gas, and to be capable of being dispersed in a used medium to a level of fine particles, with the dispersed state being stable. In particular, there is a strong demand for a pigment which has a good yellow hue and is fast to light, moist heat, and active gases in the environment, particularly for a pigment having high tinctorial strength and is fast against light.

That is, in comparison with a dye which is required to have properties as colorant molecules, the pigment is required to have more properties, i.e., it is required to satisfy all of the above-mentioned requirements as a solid of an aggregate of a colorant (dispersion of fine particles) as well as the properties as molecules of a colorant molecule. As a result, a group of compounds which can be used as pigments are extremely limited in comparison with dyes. Even when high-performance dyes are converted to pigments, few of them can satisfy requirement for the properties as a dispersion of fine particles. Thus, such pigments are difficult to develop. This can be confirmed from the fact that the number of pigments registered in Color Index is no more than $1/10$ of the number of dyes.

Azo pigments are excellent in hue and tinctorial strength which are characteristics of coloring, and hence they have widely been used in printing inks, ink for an inkjet system, and electro-photographic materials. Of the pigments, diarylide pigments are the most typically used as yellow azo pigments. Examples of such diarylide pigments include C.I. pigment yellow 12, C.I. pigment yellow 13, and C.I. pigment yellow 17. However, diarylide pigments are inferior in fastness, particularly light fastness, and hence they are decomposed when prints printed by them are exposed to light, thus being inappropriate for prints which are to be stored for a long time.

In order to remove such defects, there have been disclosed azo pigments having a fastness improved by increasing molecular weight or by introducing a group having a strong intermolecular interaction (see, for example, patent documents 1 to 3). However, even the improved pigments, for example, the pigments described in patent document 1 have the defect that they have still insufficient light fastness though improved to some extent, and pigments described in, for example, patent documents 2 and 3 have a greenish hue and a low tinctorial strength, thus being inferior in coloring characteristics.

Also, patent documents 4, 5 and 6 disclose colorants which have absorption characteristics of excellent color reproducibility and has a sufficient fastness. However, all of the specific compounds described in the patent documents are soluble in water or in an organic solvent, thus being insufficient in resistance to chemicals.

In the case of expressing a full-color image based on the subtractive color mixing process using three colors of yellow, magenta, and cyan or using four colors further including black, use of a pigment having an inferior fastness as a yellow pigment would change gray balance of the prints with the lapse of time, and use of a pigment having inferior coloring characteristics would reduce color reproducibility upon printing. Thus, in order to obtain prints which can maintain high color reproducibility for a long time, there have been desired a yellow pigment and a pigment dispersion which have both good coloring characteristics and good fastness.

Patent document 1: JP-A-56-38354
Patent document 2: U.S. Pat. No. 2,936,306
Patent document 3: JP-A-11-100519
Patent document 4: JP-A-2003-277662
Patent document 5: JP-A-2005-220217
Patent document 6: JP-A-2008-7732

DISCLOSURE OF THE INVENTION

Problems that the Invention is to Solve

An object of the invention is to provide azo compounds, azo pigments having excellent coloring characteristics such as hue and having high tinctorial strength and excellent fastness such as light fastness and ozone fastness, a dispersion, a coloring composition and an ink for inkjet recording containing the azo compound or the azo pigment, an ink tank for inkjet recording which contains the ink, an inkjet recording method using it, and recorded products having the above-described coloring characteristics and the above-described fastness.

Means for Solving the Problem

As a result of intensive investigations in consideration of the above-mentioned circumstances, the inventors have obtained novel azo pigments and have found that the azo pigments are excellent in that they can provide excellent coloring characteristics and fastness at the same time, thus having achieved the present invention.

That is, the invention is as follows.

[1]

An azo pigment represented by the general formula (1), a tautomer, salt, or hydrate thereof.

General formula (1)

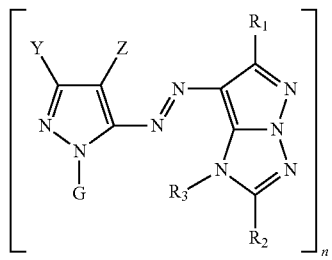

In general formula (1), $R_1$, $R_2$, $R_3$, Y, Z, and G each independently represents a hydrogen atom or a substituent; n represents an integer of from 2 to 4; when n=2, the general formula (1) represents a dimer formed through $R_1$, $R_2$, $R_3$, Y, Z, or G; when n=3, the general formula (1) represents a trimer formed through $R_1$, $R_2$, $R_3$, Y, Z, or G; and when n=4, the general formula (1) represents a tetramer formed through $R_1$, $R_2$, $R_3$, Y, Z, or G.

[2]

An azo pigment represented by the following general formula (2), a tautomer, salt, or hydrate thereof.

General formula (2)

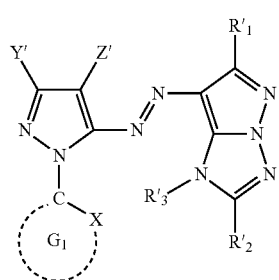

In general formula (2), $R'_1$, $R'_2$, and Y' each independently represents a hydrogen atom, a straight or branched alkyl group containing from 1 to 4 carbon atoms, an alkenyl group containing from 2 to 4 carbon atoms, an alkynyl group containing from 2 to 4 carbon atoms, an acyl group containing from 1 to 5 carbon atoms, an aralkyl group containing from 7 to 9 carbon atoms, a 5- to 8-membered, saturated or unsaturated hydrocarbon ring group, or a 5- to 8-membered, saturated or unsaturated heterocyclic group; $R'_3$ represents a hydrogen atom or a monovalent substituent; Z' represents an electron-withdrawing group having a Hammett σp value of 0.2 or more; X represents a hetero atom adjacent to the carbon atom; $G_1$ represents atoms necessary for forming a 5- to 8-membered, saturated or unsaturated heterocyclic ring; when any one of $R'_1$, $R'_2$, Y', and $G_1$ represents a 5- to 8-membered, saturated or unsaturated heterocyclic ring, it represents a monocyclic ring or a condensed ring; and when any one of $R'_1$, $R'_2$, $R'_3$, Y', and $G_1$ represents a 5-membered unsaturated heterocyclic ring, it has two or more nitrogen atoms within the ring.

[3]

The azo pigment, tautomer, salt or hydrate according to [2], wherein X in the general formula (2) is a nitrogen atom.

[4]

The azo pigment, tautomer, salt or hydrate according to [2], wherein $G_1$ in the general formula (1) is selected from the substituent group represented by the following general formulae (3)-1 to (3)-6.

General formula (3)

(3)-1

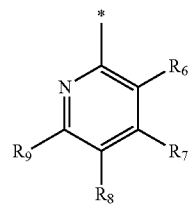

(3)-2

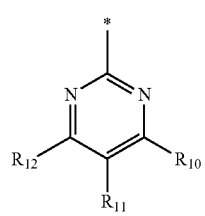

(3)-3

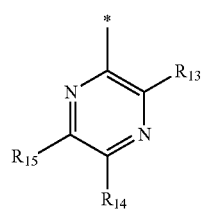

(3)-4

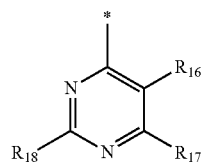

General formula (3)

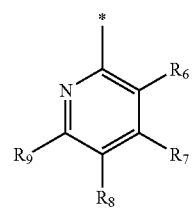
(3)-1

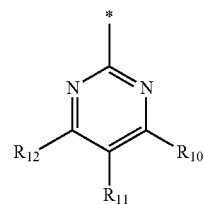
(3)-2

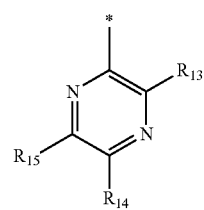
(3)-3

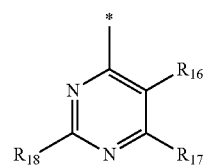
(3)-4

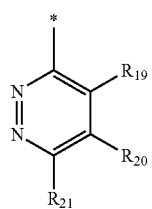
(3)-5

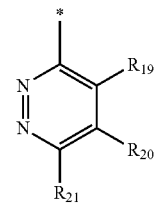
(3)-5

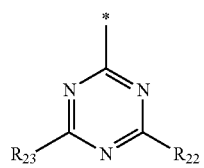
(3)-6

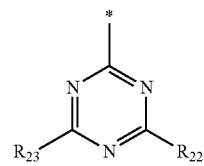
(3)-6

In general formula (3), $R_6$ to $R_{23}$ each independently represents a hydrogen atom or a substituent; and $R_6$ to $R_{21}$ may be connected to each other to form a ring.

[5]

The azo pigment, tautomer, salt or hydrate according to [1], wherein the azo pigment represented by the general formula (1) is an azo pigment represented by the following general formula (4).

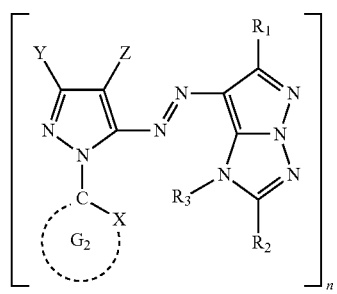
General formula (4)

In general formula (4), n, $R_1$, $R_2$, $R_3$, Y, and Z are respectively the same as defined for n, $R_1$, $R_2$, $R_3$, Y, and Z in the general formula (1); X represents a hetero atom adjacent to the carbon atom; $G_2$ represents atoms necessary for forming a 5- to 8-membered, saturated or unsaturated heterocyclic ring; when n=2, the general formula (4) represents a dimer formed through $R_1$, $R_2$, $R_3$, Y, Z, or $G_2$; when n=3, the general formula (4) represents a trimer formed through $R_1$, $R_2$, $R_3$, Y, Z, or $G_2$; when n=4, the general formula (4) represents a tetramer formed through $R_1$, $R_2$, $R_3$, Y, Z, or $G_2$; and when any one of $R_1$, $R_2$, $R_3$, Y and $G_2$ represents a 5- to 8-membered, saturated or unsaturated heterocyclic ring, it represents a monocyclic ring or a condensed ring.

[6]

The azo pigment, tautomer, salt or hydrate according to [5], wherein X in the general formula (4) is a nitrogen atom.

[7]

The azo pigment, tautomer, salt or hydrate according to [5] or [6], wherein $G_2$ in the general formula (4) is a group selected from the substituent group represented by the following general formulae (3)-1 to (3)-6.

In general formula (3), $R_6$ to $R_{23}$ each independently represents a hydrogen atom or a substituent; and $R_6$ to $R_{21}$ may be connected to each other to form a ring.

[8]

An azo compound represented by the following general formula (2).

General formula (2)

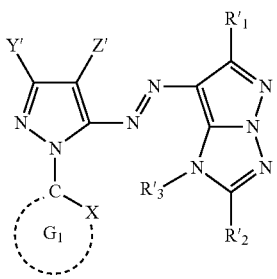

In general formula (2), $R'_1$, $R'_2$, and Y' each independently represents a hydrogen atom, a straight or branched alkyl group containing from 1 to 4 carbon atoms, an alkenyl group containing from 2 to 4 carbon atoms, an alkynyl group containing from 2 to 4 carbon atoms, an acyl group containing from 1 to 5 carbon atoms, an aralkyl group containing from 7 to 9 carbon atoms, a 5- to 8-membered, saturated or unsaturated hydrocarbon ring group, or a 5- to 8-membered, saturated or unsaturated heterocyclic group; $R'_3$ represents a hydrogen atom or a monovalent substituent; Z' represents an electron-withdrawing group having a Hammett σp value of 0.2 or more; X represents a hetero atom adjacent to the carbon atom; $G_1$ represents atoms necessary for forming a 5- to 8-membered, saturated or unsaturated heterocyclic ring; when any one of $R'_1$, $R'_2$, Y', and $G_1$ represents a 5- to 8-membered, saturated or unsaturated heterocyclic ring, it represents a monocyclic ring or a condensed ring; and when any one of $R'_1$, $R'_2$, $R'_3$, Y', and $G_1$ represents a 5-membered unsaturated heterocyclic ring, it has two or more nitrogen atoms within the ring.

[9]

The azo compound according to [8], wherein $G_1$ in the general formula (2) is selected from the substituent group represented by the following general formulae (3)-1 to (3)-6.

General formula (3)

(3)-1

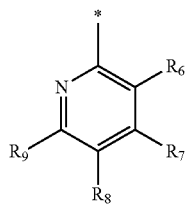

(3)-2

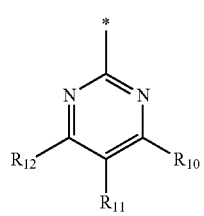

(3)-3

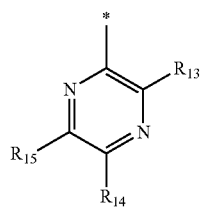

(3)-4

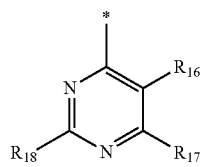

(3)-5

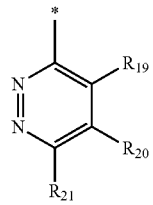

(3)-6

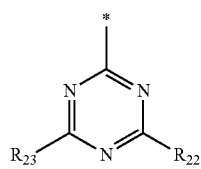

In general formula (3), $R_6$ to $R_{23}$ each independently represents a hydrogen atom or a substituent, and $R_6$ to $R_{21}$ may be connected to each other to form a ring.

[10]

An azo compound represented by the following general formula (4).

General formula (4)

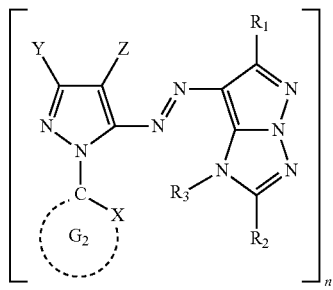

In general formula (4), $R_1$, $R_2$, $R_3$, Y, and Z each independently represents a hydrogen atom or a substituent; n represents an integer of 2 to 4; X represents a hetero atom adjacent to the carbon atom, $G_2$ represents atoms necessary for forming a 5- to 8-membered, saturated or unsaturated heterocyclic ring; when n=2, the general formula (4) represents a dimer formed through $R_1$, $R_2$, $R_3$, Y, Z, or $G_2$; when n=3, the general formula (4) represents a trimer formed through $R_1$, $R_2$, $R_3$, Y, Z, or $G_2$; when n=4, the general formula (4) represents a tetramer formed through $R_1$, $R_2$, $R_3$, Y, Z, or $G_2$; and when any one of $R_1$, $R_2$, $R_3$, Y, Z and $G_2$ represents a 5- to 8-membered, saturated or unsaturated heterocyclic ring, it represents a monocyclic ring or a condensed ring.

[11]

The azo compound according to [10], wherein $G_2$ in the general formula (4) is a group selected from the substituent group represented by the following general formulae (3)-1 to (3)-6.

General formula (3)

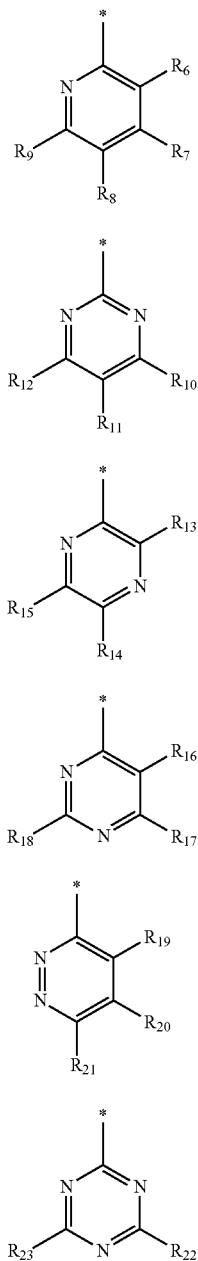

In general formula (3), $R_6$ to $R_{23}$ each independently represents a hydrogen atom or a substituent, and $R_6$ to $R_{21}$ may be connected to each other to form a ring.

[12]

A dispersion which contains at least one of the azo pigments described in any one of [1] to [7], the tautomers, salts, and hydrates thereof or at least one of the azo compounds described in any one of [8] to [11].

[13]

A coloring composition, which contains the dispersion recited in [12].

[14]

An ink for inkjet recording, which contains the dispersion recited in [12].

[15]

An ink tank for inkjet recording, which contains the ink for inkjet recording recited in [14].

[16]

An inkjet recording method containing using the ink for inkjet recording recited in [14].

[17]

A recorded product obtained by using the ink for inkjet recording recited in [14].

ADVANTAGES OF THE INVENTION

According to the present invention, there are provided azo pigments having excellent coloring characteristics such as tinctorial strength and hue and good fastness such as ozone fastness, particularly having excellent light fastness and dispersibility. A pigment dispersion having excellent coloring characteristics, fastness, and dispersion stability is obtained by dispersing the pigment of the invention in various media. Also, according to the invention, there are provided a coloring composition and an ink for inkjet recording, which contain the azo pigment, and an ink tank for inkjet recording. Also, according to the invention, there is provided an inkjet recording method which can provide a recorded product having the above-described excellent coloring characteristics and the above-described fastness. Also, according to the invention, there is provided a recorded product having the above-described characteristic properties and the above-described fastness. The pigment dispersion can be used for an ink for printing such as inkjet printing, a color toner for electrophotography, a display such as LCD or PDP, a color filter to be used in photographing equipment such as CCD, a paint, a colored plastic, etc.

BEST MODE FOR CARRYING OUT THE INVENTION

Figure 1:
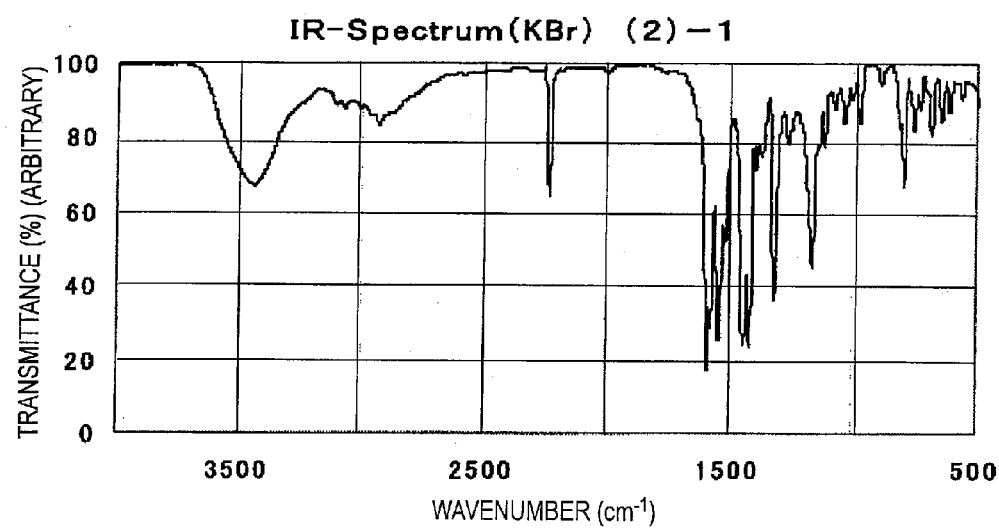
FIG. 1 is an infrared absorption spectrum of an illustrative compound (2)-1 of the azo pigment obtained in Example 2.

The present invention will be described in detail below.

A Hammett substituent constant σp to be used in this specification is briefly explained below.

The Hammett's rule is an empirical rule advocated by L. P. Hammett in 1935 in an attempt to quantitatively discuss the influences of a substituent on the reaction or equilibrium of a benzene derivative, the validity of which has been widely accepted nowadays. Substituent constants obtained by the Hammett's rule include σp and σm values. These values are found in a number of general books. The details are given in, for example, J. A. Dean (ed.), *Lange's Handbook of Chemistry*, the 12th Ed., MacGraw-Hill, 1979 and *Kagakuno Ryoiki*, Extra No. 122, Nankodo, 1979, 96-103. While substituents are described in the invention by reference to their Hammett substituent constants σp, it is needless to say that such description applies to not only the substituents whose Hammett substituent constants σp are known from the literature but those whose Hammett substituent constants σp are unknown from the literature but are to fall within a range in question when determined in accordance with the Hammett's rule. Although compounds of the invention represented by the general formulae (1), (2), (4) and (5) are not benzene derivatives, σp values are referred to as a measure of the electron effect of their substituents irrespective of the position of substitution. In the invention, the σp value will be used hereinafter.

Azo Pigments

Pigments are in a state wherein molecules constituting them are strongly connected to each other through aggregation energy produced by strong interaction between pigment molecules. In order to realize this state, van der Waals force and intermolecular hydrogen bond are necessary as described in, for example, *The Imaging Society of Japan*, vol. 43, p. 10 (2004).

In order to increase the intermolecular van der Waals force, introduction of an aromatic group, a polar group and/or a hetero atom to a molecule may be considered. Also, in order to form intermolecular hydrogen bond, introduction of a substituent which contains a hydrogen atom connected to a hetero atom and/or introduction of an electron donative substituent may be considered. Further, polarity of the entire molecule may preferably be considered to be higher. For these purposes, with a chain group such as an alkyl group, a shorter group may be considered to be preferred and, with respect to the value of molecular weight/azo group, a smaller value may be considered to be preferred.

From these standpoints, pigment particles preferably contain an amido bond, a sulfonamido bond, an ether bond, a sulfon group, an oxycarbonyl group, an imido group, a carbamoylamino group, a heterocyclic ring, a benzene ring, or the like.

The azo pigments of the invention are represented by the following general formula (1).

The compounds represented by the general formula (1) intend to produce intermolecular interaction between colorant molecules due to the unique structure thereof, show a low solubility for water or for an organic solvent, thus being usable as azo pigments.

As is different from dyes which are used by dissolving in water or an organic solvent in a molecular dispersion state, pigments are used by finely dispersing in a solvent as solid particles such as molecular aggregates.

The azo pigments represented by the general formula (1) and the tautomers, polymorphic forms, salts, and complexes thereof will be described in detail below.

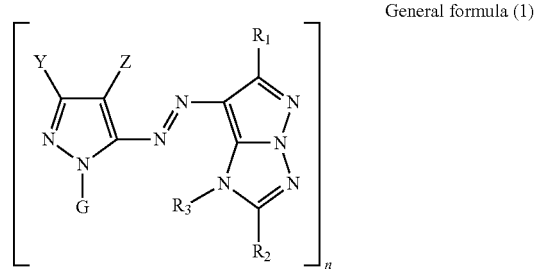

General formula (1)

(In the general formula (1), $R_1$, $R_2$, $R_3$, Y, Z, and G each independently represents a hydrogen atom or a substituent, and n represents an integer of from 2 to 4. When n=2, the general formula (1) represents a dimer formed through $R_1$, $R_2$, $R_3$, Y, Z, or G. When n=3, the general formula (1) represents a trimer formed through $R_1$, $R_2$, $R_3$, Y, Z, or G. When n=4, the general formula (1) represents a tetramer formed through $R_1$, $R_2$, $R_3$, Y, Z, or G.)

The foregoing general formula (1) will be described in detail below.

In the general formula (1), n represents an integer of from 2 to 4, preferably 2 or 3, more preferably 2.

When n represents 2 or more, the molecular weight becomes larger, and intermolecular interaction such as intermolecular π-π stacking becomes stronger. When the intermolecular interaction becomes stronger, there results improved solvent resistance. Further, when the intermolecular interaction becomes stronger and the crystallinity is more enhanced, energy relaxation due to lattice vibration is liable to occur, thus light fastness being improved. On the other hand, when n exceeds 4, the molecular weight becomes large, but it becomes difficult for the molecule to keep it in a planar form due to its steric hindrance. As a result, the intermolecular interaction is weakened, and light fastness and solvent fastness tend to be reduced.

$R_1$, $R_2$, $R_3$, Y, Z, or G may have a substituent.

In the general formula (1), examples of the group represented by $R_1$, $R_2$, $R_3$, Y, Z, or G include a hydrogen atom, a straight or branched alkyl group containing from 1 to 6 carbon atoms, a straight or branched aralkyl group containing from 7 to 12 carbon atoms, a straight or branched alkenyl group containing from 2 to 6 carbon atoms, a straight or branched alkynyl group containing from 2 to 6 carbon atoms, a cycloalkyl group containing from 3 to 6 carbon atoms, a cycloalkenyl group containing from 3 to 10 carbon atoms (for example, methyl, ethyl, n-propyl, i-propyl, n-butyl, i-butyl, sec-butyl, t-butyl, 2-ethylhexyl, 2-methylsulfonylethyl, 3-phenoxypropyl, trifluoromethyl, or cyclopentyl), a halogen atom (for example, a fluorine atom, a chlorine atom, or a bromine atom), an aryl group (e.g., phenyl, 4-t-butylphenyl, 2,4-di-t-amylphenyl, or 4-acetamidophenyl), a heterocyclic group (for example, imidazolyl, pyrazolyl, triazolyl, 2-furyl, 2-thienyl, 2-pyridyl, 2-pyrimidinyl, or 2-benzothiazolyl), a cyano group, a hydroxyl group, a nitro group, a carboxyl group, an amino group, an alkyloxy group (for example, methoxy, ethoxy, 2-methoxyethoxy, or 2-methylsulfonylethoxy), an aryloxy group (for example, phenoxy, 2-methylphenoxy, 4-t-butylphenoxy, 3-nitrophenoxy, 3-t-butyloxycarbonylphenoxy, or 3-methoxycarbonylphenyloxy), an acylamino group (for example, acetamido, benzamido, or 4-(3-t-butyl-4-hydroxyphenoxy)butanamido), an alkylamino group (for example, methylamino, butylamino, diethylamino, or methylbutylamino), an arylamino group (for example, phenylamino or 2-chloroanilino), a ureido group (for example, phenylureido, methylureido, or N,N-dibutylureido), a sulfamoylamino group (for example, N,N-dipropylsulfamoylamino), an alkylthio group (for example, methylthio, octylthio, or 2-phenoxyethylthio), an arylthio group (for example, phenylthio, 2-butyoxy-5-t-octylphenylthio, or 2-carboxyphenylthio), an alkyloxycarbonylamino group (for example, methoxycarbonylamino), an alkylsulfonylamino group, arylsulfonylamino group (for example, methylsulfonylamino, phenylsulfonylamino, or p-toluenesulfonylamino), a carbamoyl group (for example, carbamoyl, N-ethylcarbamoyl, or N,N-dibutylcarbamoyl), a sulfamoyl group (for example, N-ethylsulfamoyl, N,N-dipropylsulfamoyl, or N-phenylsulfamoyl), a sulfonyl group (for example, methylsulfonyl, phenylsulfonyl, or p-toluenesulfonyl), an alkyloxycarbonyl group (for example, methoxycarbonyl or ethoxycarbonyl), a heterocyclic oxy group (for example, 1-phenyltetrazol-5-oxy or 2-tetrahydropyranyloxy), an azo group (for example, phenylazo, 4-methoxyphenylazo, 4-pivaloylaminophenylazo, or 2-hydroxy-4-propanoylphenylazo), an acyloxy group (for example, acetoxy group), a carbamoyloxy group (for example, N-methylcarbamoyloxy or N-phenylcarbamoyloxy), a silyloxy group (for example, trimethylsilyloxy or dibutylmethylsilyloxy), an aryloxycarbonylamino group (for example, phenoxycarbonylamino), an imido group (for example, N-succinimido or N-phthalimido), a heterocyclic thio group (for example, 2-benzothiazolylthio, 2,4-di-phenoxy-1,3,5-triazole-6-thio group, or 2-pyridylthio), a sulfinyl group (for example, 3-phenoxypropylsulfinyl), a phosphonyl group (for example, phenoxyphosphonyl, octyloxyphosphonyl, or phenylphosphonyl), an aryloxycarbonyl group (for example, phenoxycarbonyl), an acyl group (for example, acetyl, 3-phenylpropanoyl, or benzoyl), and an ionic hydrophilic group (for example, a carboxyl group, a sulfo group, a phosphono group, or a quaternary ammonium group).

In the case where the azo pigment of the invention contains an ionic hydrophilic group as a substituent, it is preferably a salt with a multi-valent metal cation (for example, magnesium ion, calcium ion, or barium ion), and is particularly preferably a lake pigment.

In the general formula (1), $R_1$ and $R_2$ each independently represents preferably a hydrogen atom, a straight or branched alkyl group containing from 1 to 6 carbon atoms, a straight or branched alkenyl group containing from 2 to 6 carbon atoms, a straight or branched alkynyl group containing from 2 to 6 carbon atoms, an aralkyl group containing from 7 to 9 carbon atoms, a substituted or unsubstituted, 5- to 8-membered aryl group, or a substituted or unsubstituted, 5- to 8-membered heterocyclic group, more preferably a hydrogen atom, a straight or branched alkyl group containing from 1 to 4 carbon atoms or a substituted or unsubstituted, 5- to 8-membered aryl group. Of these, a straight or branched alkyl group containing from 1 to 4 carbon atoms or a substituted or unsubstituted 5- to 6-membered aryl group are most preferred.

In the general formula (1), examples of a monovalent substituent represented by $R_3$ include a straight or branched alkyl group containing from 1 to 6 carbon atoms (for example, methyl, ethyl, n-propyl, i-propyl, n-butyl, i-butyl, sec-butyl, t-butyl, 2-ethylhexyl, 2-methylsulfonylethyl, 3-phenoxypropyl, or trifluoromethyl), an aralkyl group containing from 7 to 12 carbon atoms (for example, benzyl or 4-aminophenylmethyl), a straight or branched alkenyl group containing from 2 to 6 carbon atoms (for example, ethenyl, 1-propenyl, or 1,3-butanedienyl), a straight or branched alkynyl group containing from 2 to 6 carbon atoms (for example, ethynyl, 1-propynyl, or 1-butynyl), a cycloalkyl group containing from 3 to 6 carbon atoms (for example, cyclopentyl), a cycloalkenyl group containing from 3 to 10 carbon atoms (for example, cyclohexenyl or cyclohexanedienyl), an aryl group (for example, phenyl, 4-t-butylphenyl, or 2,4-di-t-amylphenyl), a heterocyclic group (for example, imidazolyl, pyrazolyl, triazolyl, 2-furyl, 2-thienyl, 2-pyrimidinyl, or 2-benzothiazolyl), an alkyloxycarbonyl group (for example, methoxycarbonyl or butyloxycarbonyl), an aryloxycarbonyl group (for example, phenoxycarbonyl), and an acyl group (for example, acetyl, 3-phenylpropanoyl, or benzoyl).

Preferred examples of $R_3$ include a hydrogen atom, a straight or branched alkyl group containing from 1 to 4 carbon atoms (for example, methyl, ethyl, n-propyl, i-propyl, n-butyl, i-butyl, sec-butyl, or t-butyl), an alkenyl group containing from 2 to 4 carbon atoms (for example, ethenyl), and an alkynyl group containing from 2 to 4 carbon atoms (for example, ethynyl).

More preferred examples of $R_3$ include a hydrogen atom, a methyl group, an ethyl group, an ethenyl group, and an ethynyl group. Of these, a hydrogen atom is particularly preferred.

Preferred examples of Y include a hydrogen atom, a straight or branched alkyl group containing from 1 to 6 carbon atoms, a straight or branched alkenyl group containing from 2 to 6 carbon atoms, a straight or branched alkynyl group containing from 2 to 6 carbon atoms, a carbamoyl group containing from 1 to 6 carbon atoms, an alkoxycarbonyl group containing from 1 to 6 carbon atoms, a substituted or unsubstituted, 5- to 8-membered aryl group, a substituted or unsubstituted, and 5- to 8-membered heterocyclic group, and more preferred are a hydrogen atom, a straight or branched alkyl group containing from 1 to 4 carbon atoms, a carbamoyl group containing from 1 to 4 carbon atoms, an alkoxycarbonyl group containing from 1 to 5 carbon atoms, and a substituted or unsubstituted, 5- to 8-membered aryl group. Of these, a hydrogen atom, a methyl group, a substituted or unsubstituted, 5- or 6-membered aryl group are particularly preferred.

In the general formula (1), Z is an electron-withdrawing group having a Hammett substituent constant σp value of 0.2 or more, preferably an electron-withdrawing group having a Hammett substituent constant σp value of 0.30 or more. With respect to the upper limit of σp value, an electron-withdrawing group having a Hammett substituent constant σp value of 1.0 or less is preferred.

Specific examples of Z which is an electron-withdrawing group having a σp value of 0.2 or more include an acyl group, an acyloxy group, a carbamoyl group, an alkyloxycarbonyl group, an aryloxycarbonyl group, a cyano group, a nitro group, a dialkylphosphono group, a diarylphosphono group, a diarylphosphinyl group, an alkylsulfinyl group, an arylsulfinyl group, an alkylsulfonyl group, an arylsulfonyl group, a sulfonyloxy group, an acylthio group, a sulfamoyl group, a thiocyanato group, a thiocarbonyl group, a halogenated alkyl group, a halogenated alkoxy group, a halogenated aryloxy group, a halogenated alkylamino group, a halogenated alkylthio group, an aryl group substituted by other electron-withdrawing group having a σp value of 0.2 or more, a heterocyclic group, a halogen atom, an azo group, and a selenocyanato group.

Preferred examples of Z include an acyl group containing from 2 to 6 carbon atoms, an acyloxy group containing from 2 to 6 carbon atoms, a carbamoyl group containing from 1 to 8 carbon atoms, an alkyloxycarbonyl group containing from 2 to 8 carbon atoms, an aryloxycarbonyl group containing from 7 to 12 carbon atoms, a cyano group, a nitro group, an alkylsulfinyl group containing from 1 to 6 carbon atoms, an arylsulfinyl group containing from 6 to 10 carbon atoms, an alkylsulfonyl group containing from 1 to 6 carbon atoms, an arylsulfonyl group containing from 6 to 10 carbon atoms, a sulfamoyl group containing from 0 to 9 carbon atoms, a halogenated alkyl group containing from 1 to 6 carbon atoms, a halogenated alkyloxy group containing from 1 to 6 carbon atoms, a halogenated alkylthio group containing from 1 to 6 carbon atoms, a halogenated aryloxy group containing from 6 to 12 carbon atoms, an aryl group containing from 7 to 12 carbon atoms and being substituted by two or more other electron-withdrawing groups having a σp value of 0.2 or more, and a 5- to 8-membered heterocyclic group containing from 1 to 10 carbon atoms and containing a nitrogen atom, an oxygen atom, or a sulfur atom.

More preferred are a cyano group, an alkyloxycarbonyl group containing from 2 to 8 carbon atoms, an alkylsulfonyl group containing from 1 to 6 carbon atoms, an arylsulfonyl group containing from 6 to 10 carbon atoms, and a sulfamoyl group containing from 0 to 9 carbon atoms. Particularly preferred are a cyano group, an alkyloxycarbonyl group containing from 2 to 8 carbon atoms, an alkylsulfonyl group containing from 1 to 4 carbon atoms, an arylsulfonyl group containing from 6 to 8 carbon atoms, and a sulfamoyl group containing from 0 to 8 carbon atoms, with a cyano group being most preferred.

In the general formula (1), preferred examples of G include a hydrogen atom, a straight or branched alkyl group, a cycloalkyl group, an acyl group, an alkenyl group, an alkynyl group, an aralkyl group, a 5- to 8-membered, saturated or unsaturated hydrocarbon ring and a 5- to 8-membered, saturated or unsaturated heterocyclic ring, when G represents a 5- to 8-membered, saturated or unsaturated hydrocarbon ring or heterocyclic ring, G is a monocyclic ring or a condensed ring. Also, G may have a substituent. More preferred examples of G include a hydrogen atom, a straight or branched alkyl group containing from 1 to 6 carbon atoms, an acyl group containing from 1 to 6 acyl group, a 5- to 8-membered, saturated or unsaturated hydrocarbon ring, and a 5- to 8-membered, saturated or unsaturated heterocyclic ring and, when G represents a 5- to 8-membered, saturated or unsaturated hydrocarbon ring or heterocyclic ring, G is a monocyclic ring or a condensed ring. Also, G may have a substituent. In particular, G is preferably a 5- to 8-membered, substituted or unsubstituted aromatic hydrocarbon ring or a 5- to 8-membered, substituted or unsubstituted heterocyclic ring group. When G represents a 5- to 8-membered, substituted or unsubstituted aromatic hydrocarbon ring or a 5- to 8-membered, substituted or unsubstituted heterocyclic ring group, G is a monocyclic ring or a condensed ring.

To illustrate the heterocyclic group represented by G in the general formula (1) without restricting the substitution position, there can be illustrated a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolyl group, and a sulfolanyl group.

Preferred examples of the heterocyclic group include a pyridyl group, a pyrazinyl group, a pyrimidinyl group, a pyridazinyl group, and a triazinyl group, with a pyridyl group, a pyrimidinyl group, and a triazinyl group being particularly preferred.

When foregoing G is a group which can further have a substituent, examples of the substituent include those which have been illustrated with respect to $R_1$, $R_2$, $R_3$, Y, Z, and G in the foregoing general formula (1).

$R_1$, $R_2$, $R_3$, Y, and Z may have a substituent, and examples of the substituent include those which have been illustrated with respect to $R_1$, $R_2$, $R_3$, Y, Z, and G in the foregoing general formula (1).

When $R_1$, $R_2$, $R_3$, Y, Z, and G each represents a divalent group, preferred examples of the divalent group include an alkylene group (for example, methylene, ethylene, propylene, butylenes, or pentylene), an alkenylene group (for example, ethenylene or propenylene), an alkynylene group (for example, ethynylene or propynylene), an arylene group (for example, phenylene or naphthylene), a divalent heterocyclic group (for example, a 6-chloro-1,3,5-triazine-2,4-diyl group, a pyrimidine-2,4-diyl group, a pyrimidine-4,6-diyl group, a quinoxaline-2,3-diyl group, or a pyridazine-3,6-diyl group), —O—, —CO—, —NR'— (wherein R' represents a hydrogen atom, an alkyl group, or an aryl group), —S—, —SO$_2$—, —SO—, or a combination thereof (for example, —NHCH$_2$CH$_2$NH— or —NHCONH—).

The alkylene group, alkenylene group, alkynylene group, arylene group, divalent heterocyclic group, and the alkyl or aryl group of R' may have a substituent.

Examples of the substituent include those which have been illustrated with respect to $R_1$, $R_2$, $R_3$, Y, Z, and G in the foregoing general formula (1).

The alkyl and aryl groups of the above-described R' are the same as those substituent examples which have been illustrated with respect to the alkyl or aryl group represented by $R_1$, $R_2$, $R_3$, Y, Z, and G in the foregoing general formula (1).

More preferred is an alkylene group containing 6 or less carbon atoms, an alkenylene group containing 6 or less carbon atoms, an alkynylene group containing 6 or less carbon atoms, an arylene group containing from 6 to 10 carbon atoms, a divalent heterocyclic group, —S—, —SO—, —SO$_2$— or a combination thereof (for example, —SCH$_2$CH$_2$S— or —SCH$_2$CH$_2$CH$_2$S—).

The divalent linking group contains preferably a total of from 0 to 20 carbon atoms, more preferably a total of from 0 to 15 carbon atoms, most preferably a total of from 0 to 10 carbon atoms.

When $R_1$, $R_2$, $R_3$, Y, Z, and G each represents a trivalent group, the trivalent group is preferably a trivalent hydrocarbon group, a trivalent heterocyclic group, >N—, or a combination thereof and a divalent group (for example, >NCH$_2$CH$_2$NH— or >NCONH—).

The trivalent linking group contains preferably a total of from 0 to 20 carbon atoms, more preferably a total of from 0 to 15 carbon atoms, most preferably a total of from 0 to 10 carbon atoms.

Regarding a preferred combination of the groups in the pigment of the invention represented by the general formula (1), compounds wherein at least one of the various groups is the aforesaid preferred group are preferred, compounds wherein more of the various groups are the aforesaid preferred groups are more preferred, and compounds wherein all of the groups are the aforesaid preferred groups are most preferred.

Particularly preferred combinations as an azo pigment of the invention represented by the general formula (1) include the following (i) to (vi).

(i) n represents an integer of from 2 to 4, preferably an integer of 2 or 3, particularly preferably 2.

(ii) $R_1$ and $R_2$ each independently represents preferably a hydrogen atom, a straight or branched alkyl group containing from 1 to 6 carbon atoms, a straight or branched alkenyl group containing from 2 to 6 carbon atoms, a straight or branched alkynyl group containing from 2 to 6 carbon atoms, a substituted or unsubstituted, 5- to 8-membered aryl group, or a substituted or unsubstituted, 5- to 8-membered heterocyclic group, more preferably a hydrogen atom, a straight or branched alkyl group containing from 1 to 4 carbon atoms, or a substituted or unsubstituted, 5- to 8-membered aryl group, most preferably a methyl group, a t-butyl group, or a substituted or unsubstituted, 5- to 6-membered aryl group.

(iii) Y represents preferably a hydrogen atom, a straight or branched alkyl group containing from 1 to 6 carbon atoms, a straight or branched alkenyl group containing from 2 to 6 carbon atoms, a straight or branched alkynyl group containing from 2 to 6 carbon atoms, a carbamoyl group containing from 1 to 6 carbon atoms, an alkoxycarbonyl group containing from 1 to 6 carbon atoms, a substituted or unsubstituted, 5- to 8-membered aryl group, or a substituted or unsubstituted, 5- to 8-membered heterocyclic group, more preferably a hydrogen atom, a straight or branched alkyl group containing from 1 to 4 carbon atoms, a carbamoyl group containing from 1 to 4 carbon atoms, an alkoxycarbonyl group containing from 1 to 4 carbon atoms, or a substituted or unsubstituted, 5- to 8-membered aryl group, most preferably a hydrogen atom, a methyl group, or a substituted or unsubstituted, 5- or 6-membered aryl group.

(iv) $R_3$ represents preferably a hydrogen atom or a monovalent substituent, more preferably a hydrogen atom, a methyl group, an ethyl group, an ethenyl group, or an ethynyl group, most preferably a hydrogen atom.

(v) Z represents preferably a cyano group, an acyl group containing from 2 to 6 carbon atoms, an acyloxy group containing from 2 to 6 carbon atoms, a carbamoyl group containing from 1 to 8 carbon atoms, an alkyloxycarbonyl group containing from 2 to 8 carbon atoms, an aryloxycarbonyl group containing from 7 to 12 carbon atoms, a nitro group, an alkylsulfinyl group containing from 1 to 6 carbon atoms, an arylsulfinyl group containing from 6 to 10 carbon atoms, an alkylsulfonyl group containing from 1 to 6 carbon atoms, an arylsulfonyl group containing from 6 to 10 carbon atoms, a sulfamoyl group containing from 0 to 9 carbon atoms, a halogenated alkyl group containing from 1 to 6 carbon atoms, a halogenated aryl group containing from 1 to 6 carbon atoms, a halogenated alkyloxy group containing from 1 to 6 carbon atoms, a halogenated alkylthio group containing from 1 to 6 carbon atoms, a halogenated aryloxy group containing from 6 to 12 carbon atoms, or a 5- to 8-membered heterocyclic group, more preferably a cyano group, an alkyloxycarbonyl group containing from 2 to 8 carbon atoms, an alkylsulfonyl group containing from 1 to 6 carbon atoms, an arylsulfonyl group containing from 6 to 10 carbon atoms, or a sulfamoyl group containing from 0 to 8 carbon atoms, most preferably a cyano group.

(vi) G represents preferably a hydrogen atom, a straight or branched alkyl group containing from 1 to 6 carbon atoms, an acyl group containing from 1 to 4 carbon atoms, an alkenyl group containing from 2 to 6 carbon atoms, an alkynyl group containing from 2 to 6 carbon atoms, an aralkyl group containing from 7 to 10 carbon atoms, a 5- to 8-membered, saturated or unsaturated hydrocarbon ring, or a 5- to 8-membered, saturated or unsaturated heterocyclic ring and, when G represents a 5- to 8-membered, saturated or unsaturated hydrocarbon ring or heterocyclic ring, the ring is a monocyclic ring or a condensed ring. Also, G may have a substituent. Further, G represents preferably a substituted or unsubstituted, 5- to 8-membered aromatic hydrocarbon ring or a substituted or unsubstituted, 5- to 8-membered aromatic heterocyclic ring and, when G represents a 5- to 8-membered aromatic hydrocarbon or aromatic heterocyclic ring, the ring is a monocyclic ring or a condensed ring. Of these, G most preferably represents a substituted or unsubstituted, 6-membered aromatic heterocyclic ring and, when G represents a substituted or unsubstituted, 6-membered aromatic heterocyclic ring, the ring is a monocyclic ring or a condensed ring.

The invention includes in its scope tautomers of the azo pigments represented by the general formula (1). Although the general formula (1) is shown in the form of limiting structure among several tautomer forms which are possible in view of chemical structure, the azo pigment may be tautomers of other structure than the shown one, and may be used as a mixture containing plural tautomers. For example, with the pigment represented by the general formula (1), azo-hydrazone tautomers represented by the following general formula (1') can be considered.

The invention also includes in its scope tautomers of the azo pigments represented by the following general formula (1') which is a tautomer of the azo pigment represented by the general formula (1).

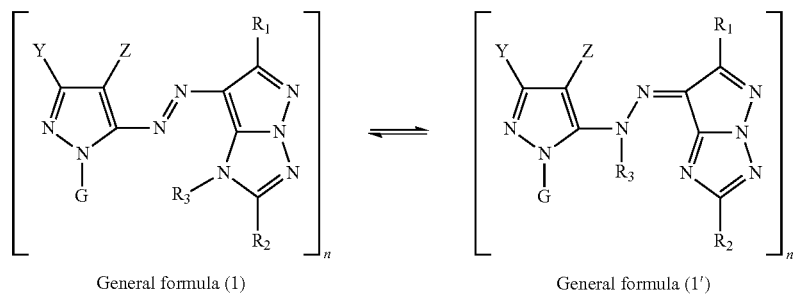

General formula (1)        General formula (1')

(n, $R_1$, $R_2$, $R_3$, Y, Z, and G in the general formula (1') are the same as defined with respect to n, $R_1$, $R_2$, $R_3$, Y, Z, and G in the general formula (1).)

The invention also relates to the azo pigments represented by the following general formula (2), tautomers, salts, and hydrates thereof.

The azo pigments represented by the following general formula (2), tautomers, salts, and hydrates thereof will be described in detail hereinafter.

General formula (2)

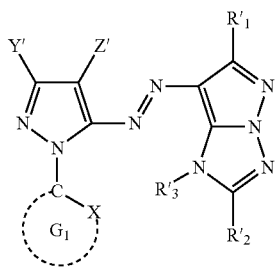

In the general formula (2), $R'_1$, $R'_2$, and $Y'$ each independently represents a hydrogen atom, a straight or branched alkyl group containing from 1 to 4 carbon atoms, an alkenyl group containing from 2 to 4 carbon atoms, an alkynyl group containing from 2 to 4 carbon atoms, an acyl group containing from 1 to 5 carbon atoms, an aralkyl group containing from 7 to 9 carbon atoms, a 5- to 8-membered, saturated or unsaturated hydrocarbon ring group, or a 5- to 8-membered, saturated or unsaturated heterocyclic group. $R'_3$ represents a hydrogen atom or a monovalent substituent. $Z'$ represents an electron-withdrawing group having a Hammett σp value of 0.2 or more. X represents a hetero atom adjacent to the carbon atom, and $G_1$ represents atoms necessary for forming a 5- to 8-membered, saturated or unsaturated heterocyclic ring. When any one of $R'_1$, $R'_2$, $Y'$, and $G_1$ represents a 5- to 8-membered saturated or unsaturated heterocyclic ring, it represents a monocyclic ring or a condensed ring. When any one of $R'_1$, $R'_2$, $R'_3$, $Y'$, and $G_1$ represents a 5-membered unsaturated heterocyclic ring, it has two or more nitrogen atoms within the ring. $R'_1$, $R'_2$, $R'_3$, $Y'$, and $G_1$ may have a substituent.

$R'_1$, $R'_2$, $R'_3$, $Y'$, $Z'$, X, and $G_1$ in the foregoing general formula (2) will be described in more detail hereinafter.

$R'_1$, $R'_2$, $R'_3$, $Y'$, $Z'$, and $G_1$ may have a substituent.

In the general formula (2), $R'_1$ and $R'_2$ each independently represents preferably a hydrogen atom, a straight or branched alkyl group containing from 1 to 4 carbon atoms, an alkenyl group containing from 2 to 4 carbon atoms, an alkynyl group containing from 2 to 4 carbon atoms, an aralkyl group containing from 7 to 9 carbon atoms, a 5- to 8-membered, saturated or unsaturated hydrocarbon ring group, or a 5- to 8-membered, saturated or unsaturated heterocyclic group. When either $R'_1$ or $R'_2$ represents a 5- to 8-membered, saturated or unsaturated hydrocarbon ring group or a 5- to 8-membered, saturated or unsaturated heterocyclic group, it is a monocyclic ring or a condensed ring and, when it may have a substituent, it may or may not have a substituent. $R'_1$ and $R'_2$ each independently represents more preferably a hydrogen atom, a straight or branched alkyl group containing from 1 to 4 carbon atoms, a 5- to 8-membered, saturated or unsaturated hydrocarbon ring group, or a 5- to 8-membered, saturated or unsaturated heterocyclic group. When either $R'_1$ or $R'_2$ represents a 5- to 8-membered, saturated or unsaturated hydrocarbon ring group or a 5- to 8-membered, saturated or unsaturated heterocyclic group, it is a monocyclic ring or a condensed ring and, when it may have a substituent, it may or may not have a substituent. Of these, a methyl group, a t-butyl group, a substituted or unsubstituted, 5- to 8-membered aryl group, and a substituted or unsubstituted, 5- to 8-membered aromatic heterocyclic group are most preferred.

Examples of the group of $R'_3$ are the same as those for $R_3$ in the foregoing general formula (1), and preferred examples are also the same as described there.

Examples of the group of $Z'$ are the same as those for Z in the foregoing general formula (1), and preferred examples are also the same as described there.

Preferred examples of $Y'$ in the general formula (2) include a hydrogen atom, a straight or branched alkyl group containing from 1 to 4 carbon atoms, an alkenyl group containing from 2 to 4 carbon atoms, an alkynyl group containing from 2 to 4 carbon atoms, an aralkyl group containing from 7 to 9 carbon atoms, a 5- to 8-membered, saturated or unsaturated hydrocarbon ring group, and a 5- to 8-membered saturated or unsaturated heterocyclic group. When $Y'$ represents a 5- to 8-membered, saturated or unsaturated hydrocarbon ring group, or a 5- to 8-membered, saturated or unsaturated heterocyclic group, it is a monocyclic ring or a condensed ring and, when it may have a substituent, it may or may not have a substituent. Of these, a hydrogen atom, a straight or branched alkyl group containing from 1 to 4 carbon atoms, a 5- to 8-membered, saturated or unsaturated hydrocarbon ring group, and a 5- to 8-membered, saturated or unsaturated heterocyclic ring group are more preferred. When $Y'$ represents a 5- to 8-membered, saturated or unsaturated hydrocarbon ring group, or a 5- to 8-membered, saturated or unsaturated heterocyclic group, it is a monocyclic ring or a condensed ring and, when it may have a substituent, it may or may not have a substituent. Of these, a hydrogen atom, a methyl group, a t-butyl group, a substituted or unsubstituted, 6-membered aryl group, and a substituted or unsubstituted, 6-membered aromatic heterocyclic group are particularly preferred.

In the general formula (2), X represents an atom adjacent to the carbon atom, preferably a hetero atom, more preferably a nitrogen atom, a sulfur atom, an oxygen atom, or a selenium atom, particularly preferably a nitrogen atom, a sulfur atom, or an oxygen atom, most preferably a nitrogen atom. A pigment wherein X is a nitrogen atom not only shows the intermolecular action of colorant molecules but also tends to form a strong intramolecular interaction, which serves to constitute a stable molecular arrangement with ease and exhibit good hue and high fastness (for example, light fastness, gas fastness, heat fastness, and solvent fastness), thus being preferred.

$G_1$ preferably represents a 5- to 8-membered, saturated or unsaturated heterocyclic ring and, when $G_1$ represents a 5- to 8-membered, saturated or unsaturated heterocyclic ring, it is a monocyclic ring or a condensed ring. Also, $G_1$ may have a substituent. More preferably, $G_1$ represents a 5- to 8-membered, aromatic heterocyclic ring and, when $G_1$ represents a 5- to 8-membered, aromatic heterocyclic ring, it is a monocyclic ring or a condensed ring. When $G_1$ represents a 5-membered aromatic heterocyclic ring, it has two or more nitrogen atoms within the ring. Particularly preferably, $G_1$ represents a substituted or unsubstituted, 6-membered aromatic heterocyclic ring and, most preferably, $G_1$ represents a substituent selected from a group of the substituents represented by (3)-1 to (3)-6 among the following general formula (3):

General formula (3)

(3)-1
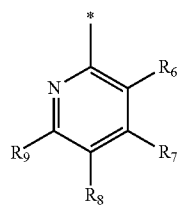

(3)-2
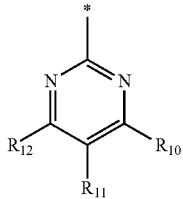

(3)-3
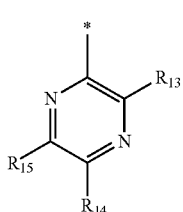

(3)-4
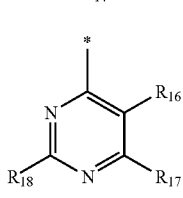

(3)-5
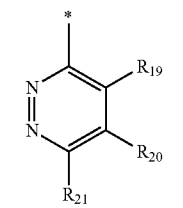

(3)-6
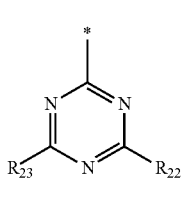

In the general formula (3), $R_6$ to $R_{23}$ each independently represents a hydrogen atom, a hydroxyl group, an amino group, a straight or branched alkyl group containing from 1 to 4 carbon atoms, a cycloalkyl group containing from 5 to 8 carbon atoms, an acyl group containing from 1 to 5 carbon atoms, an alkenyl group containing from 2 to 4 carbon atoms, an alkynyl group containing from 2 to 4 carbon atoms, an alkyloxy group containing from 1 to 4 carbon atoms, an alkylamino group containing from 1 to 8 carbon atoms, an alkyloxycarbonyl group containing from 2 to 5 carbon atoms, an amido group containing from 1 to 5 carbon atoms, an aralkyl group containing from 7 to 10 carbon atoms, a 5- to 8-membered, saturated or unsaturated hydrocarbon ring, or a 5- to 8-membered, saturated or unsaturated heterocyclic ring.

When $R_6$ to $R_{23}$ each independently represents a 5- to 8-membered, saturated or unsaturated hydrocarbon ring or a 5- to 8-membered, saturated or unsaturated heterocyclic ring, it is a monocyclic ring or a condensed ring. Also, when $R_6$ to $R_{23}$ may further have a substituent, they may or may not have a substituent. More preferably, $R_6$ to $R_{23}$ each independently represents a hydrogen atom, a hydroxyl group, an amino group, a straight or branched alkyl group containing from 1 to 4 carbon atoms, an acyl group containing from 1 to 5 carbon atoms, an alkyloxy group containing from 1 to 4 carbon atoms, an alkylamino group containing from 1 to 8 carbon atoms, an alkyloxycarbonyl group containing from 2 to 5 carbon atoms, or an amido group containing from 1 to 5 carbon atoms. Of these, a hydrogen atom, a hydroxyl group, an amino group, a methyl group, a methyloxy group, a methylamino group, and an acetamido group are particularly preferred.

$R_6$ to $R_{21}$ each may be connected to each other and, in such cases, $R_6$ to $R_{21}$ represent preferably non-metallic atoms necessary for forming a 5- to 7-membered hydrocarbon ring or a 5- to 7-membered heterocyclic ring, more preferably non-metallic atoms necessary for forming a 6-membered aromatic hydrocarbon ring or a 6-membered aromatic heterocyclic ring.

To illustrate the heterocyclic group represented by $G_1$ in the general formula (2) without restricting the substitution position, there can be illustrated a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a pyrazolyl group, an imidazolyl group, a benzimidazolyl group, a triazolyl group, an oxazolyl group, a benzoxazolyl group, a thiadiazolyl group, an isoxazolyl group, a benzisoxazolyl group, a pyrrolidinyl group, a piperidinyl group, a piperazinyl group, an imidazolidinyl group, and a sulfolanyl group.

Preferred examples of the heterocyclic group include a pyridyl group, a pyrazinyl group, a pyrimidinyl group, a pyridazinyl group, and a triazinyl group, with a pyridyl group, a pyrimidinyl group, and a triazinyl group being particularly preferred.

When foregoing $G_1$ is a group which can further have a substituent, examples of the substituent include those which have been illustrated with respect to $R_1$, $R_2$, $R_3$, Y, Z, and G in the foregoing general formula (1).

Regarding a preferred combination of the groups in the pigment of the invention represented by the general formula (2), compounds wherein at least one of the various groups is the aforesaid preferred group are preferred, compounds wherein more of the various groups are the aforesaid preferred groups are more preferred, and compounds wherein all of the groups are the aforesaid preferred groups are most preferred.

Particularly preferred combinations as an azo pigment of the invention represented by the general formula (2) include the following (i) to (vii).

(i) $R'_1$ and $R'_2$ each independently represents preferably a hydrogen atom, a straight or branched alkyl group containing from 1 to 4 carbon atoms, a straight or branched alkenyl group containing from 2 to 4 carbon atoms, a straight or branched alkynyl group containing from 2 to 4 carbon atoms, an aralkyl group containing from 7 to 9 carbon atoms, a 5- to 8-membered, saturated or unsaturated hydrocarbon ring group, or a 5- to 8-membered, saturated or unsaturated heterocyclic group. When either $R'_1$ or $R'_2$ represents a 5- to 8-membered, saturated or unsaturated hydrocarbon ring group or a 5- to 8-membered, saturated or unsaturated heterocyclic group, it is a monocyclic ring or a condensed ring and, when it may have a substituent, it may or may not have a substituent. $R'_1$ and $R'_2$ each independently represents more preferably a hydrogen atom, a straight or branched alkyl group containing from 1 to 4 carbon atoms, a 5- to 8-membered, saturated or unsaturated hydrocarbon ring group, or a 5- to 8-membered, saturated or unsaturated heterocyclic group. When either $R'_1$ or $R'_2$ represents a 5- to 8-membered, saturated or unsaturated hydrocarbon ring group or a 5- to 8-membered, saturated or unsaturated heterocyclic group, it is a monocyclic ring or a condensed ring and, when it may have a substituent, it may or may not have a substituent. Of these, a methyl group, a t-butyl group, a substituted or unsubstituted, 5- to 8-membered aryl group, and a substituted and unsubstituted, 5- to 8-membered aromatic heterocyclic group are most preferred.

(ii) Y' represents preferably a hydrogen atom, a straight or branched alkyl group containing from 1 to 4 carbon atoms, a straight or branched alkenyl group containing from 2 to 4 carbon atoms, a straight or branched alkynyl group containing from 2 to 4 carbon atoms, an aralkyl group containing from 7 to 9 carbon atoms, a 5- to 8-membered, saturated or unsaturated hydrocarbon ring group, or a 5- to 8-membered, saturated or unsaturated heterocyclic group. When Y' represents a 5- to 8-membered, saturated or unsaturated hydrocarbon ring group or a 5- to 8-membered, saturated or unsaturated heterocyclic group, it is a monocyclic ring or a condensed ring and, when it may have a substituent, it may or may not have a substituent. Of these, a hydrogen atom, a straight or branched alkyl group containing from 1 to 4 carbon atoms, a 5- to 8-membered, saturated or unsaturated hydrocarbon ring group, and a 5- to 8-membered, saturated or unsaturated heterocyclic group are more preferred. When Y' represents a 5- to 8-membered, saturated or unsaturated hydrocarbon ring group or a 5- to 8-membered, saturated or unsaturated heterocyclic group, it is a monocyclic ring or a condensed ring and, when it may have a substituent, it may or may not have a substituent. Of these, a hydrogen atom, a methyl group, a t-butyl group, a substituted or unsubstituted, 6-membered aromatic hydrocarbon group, and a substituted and unsubstituted, 6-membered aromatic heterocyclic group are most preferred.

(iii) $R'_3$ represents preferably a hydrogen atom or a monovalent substituent, more preferably a hydrogen atom, a methyl group, an ethyl group, an ethenyl group, or an ethynyl group, most preferably a hydrogen atom.

(iv) Z represents preferably a cyano group, an acyl group containing from 2 to 6 carbon atoms, an acyloxy group containing from 2 to 6 carbon atoms, a carbamoyl group containing from 1 to 8 carbon atoms, an alkyloxycarbonyl group containing from 2 to 8 carbon atoms, an aryloxycarbonyl group containing from 7 to 12 carbon atoms, a nitro group, an alkylsulfinyl group containing from 1 to 6 carbon atoms, an arylsulfinyl group containing from 6 to 10 carbon atoms, an alkylsulfonyl group containing from 1 to 6 carbon atoms, an arylsulfonyl group containing from 6 to 10 carbon atoms, a sulfamoyl group containing from 0 to 9 carbon atoms, a halogenated alkyl group containing from 1 to 6 carbon atoms, a halogenated aryl group containing from 1 to 6 carbon atoms, a halogenated alkyloxy group containing from 1 to 6 carbon atoms, a halogenated alkylthio group containing from 1 to 6 carbon atoms, a halogenated aryloxy group containing from 6 to 12 carbon atoms, or a 5- to 8-membered heterocyclic group, more preferably a cyano group, an alkyloxycarbonyl group containing from 2 to 8 carbon atoms, an alkylsulfonyl group containing from 1 to 6 carbon atoms, an arylsulfonyl group containing from 6 to 10 carbon atoms, or a sulfamoyl group containing from 0 to 8 carbon atoms, most preferably a cyano group.

(v) X represents preferably a hetero atom, more preferably a nitrogen atom, an oxygen atom, a sulfur atom, or a selenium atom, particularly preferably a nitrogen atom, an oxygen atom, or a sulfur atom, most preferably a nitrogen atom.

(vi) $G_1$ represents preferably a 5- to 8-membered, saturated or unsaturated heterocyclic ring and, when G represents a 5- to 8-membered, saturated or unsaturated heterocyclic ring, the ring is a monocyclic ring or a condensed ring. Also, $G_1$ may have a substituent. When $G_1$ represents a 5-membered heterocyclic ring, the ring has two or more nitrogen atoms within the ring. Further, $G_1$ more preferably represents a substituted or unsubstituted, 5- to 8-membered aromatic heterocyclic ring and, when G represents a substituted or unsubstituted, 5- to 8-membered aromatic heterocyclic ring, the ring is a monocyclic ring or a condensed ring. When $G_1$ represents a 5-membered aromatic heterocyclic ring, the ring has two or more nitrogen atoms within the ring. $G_1$ particularly preferably represents a substituted or unsubstituted, 6-membered aromatic heterocyclic ring, most preferably represents a substituent selected from a group of the substituents represented by (3)-1 to (3)-6 among the following general formula (3):

General formula (3)

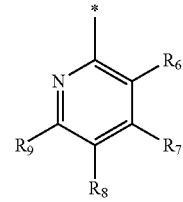

(3)-1

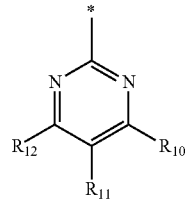

(3)-2

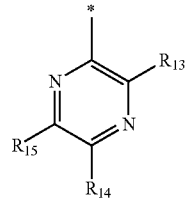

(3)-3

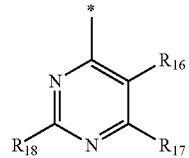

(3)-4

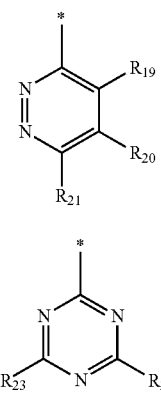

(vii)

$R_6$ to $R_{23}$ each independently represents a hydrogen atom, a hydroxyl group, an amino group, a straight or branched alkyl group containing from 1 to 4 carbon atoms, a cycloalkyl group containing from 5 to 8 carbon atoms, an acyl group containing from 1 to 5 carbon atoms, an alkenyl group containing from 2 to 4 carbon atoms, an alkynyl group containing from 2 to 4 carbon atoms, an alkyloxy group containing from 1 to 4 carbon atoms, an alkylamino group containing from 1 to 8 carbon atoms, an alkyloxycarbonyl group containing from 2 to 5 carbon atoms, an amido group containing from 1 to 5 carbon atoms, an aralkyl group containing from 7 to 10 carbon atoms, a 5- to 8-membered, saturated or unsaturated hydrocarbon ring, or a 5- to 8-membered, saturated or unsaturated heterocyclic ring. When $R_6$ to $R_{23}$ each independently represents a 5- to 8-membered, saturated or unsaturated hydrocarbon ring or a 5- to 8-membered, saturated or unsaturated heterocyclic ring, it is a monocyclic ring or a condensed ring. Also, $R_6$ to $R_{23}$ may further have a substituent. More preferably, $R_6$ to $R_{23}$ each independently represents a hydrogen atom, a hydroxyl group, an amino group, a straight or branched alkyl group containing from 1 to 4 carbon atoms, an acyl group containing from 1 to 5 carbon atoms, an alkyloxy group containing from 1 to 4 carbon atoms, an alkylamino group containing from 1 to 8 carbon atoms, an alkyloxycarbonyl group containing from 2 to 5 carbon atoms, or an amido group containing from 1 to 5 carbon atoms. Of these, a hydrogen atom, a hydroxyl group, an amino group, a methyl group, a methyloxy group, a methylamino group, and an acetamido group are particularly preferred.

$R_6$ to $R_{21}$ each may be connected to each other and, in such cases, $R_6$ to $R_{21}$ represent preferably non-metallic atoms necessary for forming a 5- to 7-membered hydrocarbon ring or a 5- to 7-membered heterocyclic ring, more preferably non-metallic atoms necessary for forming a 6-membered aromatic hydrocarbon ring or a 6-membered aromatic heterocyclic ring.

The invention includes in its scope tautomers of the azo pigments represented by the general formula (2). Although the general formula (2) is shown in the form of limiting structure among several tautomer forms which are possible in view of chemical structure, the azo pigment may be tautomers of other structure than the shown one, and may be used as a mixture containing plural tautomers. For example, with the pigment represented by the general formula (2), azo-hydrazone tautomers represented by the following general formula (2') can be considered.

The invention also includes in its scope tautomers of the azo pigments represented by the following general formula (2') which is a tautomer of the azo pigment represented by the general formula (2).

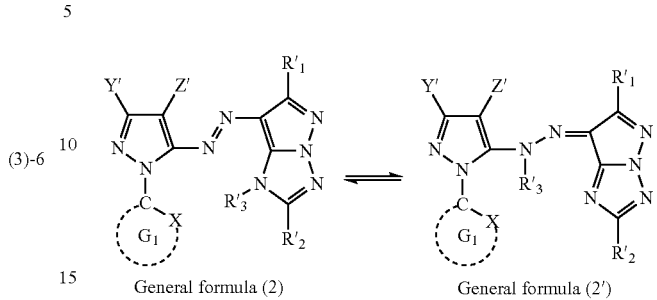

General formula (2)  General formula (2')

$R'_1$, $R'_2$, $R'_3$, $Y'$, $Z'$, and $G_1$ in the general formula (2') are the same as defined with respect to $R'_1$, $R'_2$, $R'_3$, $Y'$, $Z'$, and $G_1$ in the general formula (2).

The azo pigments represented by the foregoing general formula (1) are preferably azo pigments represented by the following general formula (4).

The azo pigments represented by the general formula (4), tautomers, salts, and hydrates thereof will be described in detail hereinafter.

General formula (4)

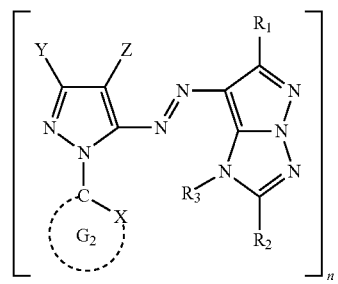

In the general formula (4), n, $R_1$, $R_2$, $R_3$, Y, and Z are respectively the same as defined for n, $R_1$, $R_2$, $R_3$, Y, and Z in the general formula (1), and X is the same as defined for X in the general formula (2). $G_2$ represents atoms necessary for forming a 5- to 8-membered, saturated or unsaturated heterocyclic ring and, when n=2, the general formula (4) represents a dimer formed through $R_1$, $R_2$, $R_3$, Y, Z, or $G_2$. When n=3, the general formula (4) represents a trimer formed through $R_1$, $R_2$, $R_3$, Y, Z, or $G_2$. When n=4, the general formula (4) represents a tetramer formed through $R_1$, $R_2$, $R_3$, Y, Z, or $G_2$. When any one of $R_1$, $R_2$, $R_3$, Y, Z, or $G_2$ represents a 5- to 8-membered, saturated or unsaturated heterocyclic ring, it represents a monocyclic ring or a condensed ring. $R_1$, $R_2$, $R_3$, Y, Z, and $G_2$ may have a substituent.

n, $R_1$, $R_2$, $R_3$, Y, Z, X, and $G_2$ in the foregoing general formula (4) will be described in more detail hereinafter.

In formula (4), examples of n, and the groups of $R_1$, $R_2$, $R_3$, Y, and Z are respectively the same as those for n, $R_1$, $R_2$, $R_3$, Y, and Z in the foregoing general formula (1), and preferred examples are also the same as described there.

Examples of X are the same as those for X in the foregoing general formula (2), and preferred examples are also the same as described there.

$G_2$ preferably represents a 5- to 8-membered, saturated or unsaturated heterocyclic ring and, when $G_2$ represents a 5- to 8-membered, saturated or unsaturated heterocyclic ring, it is a monocyclic ring or a condensed ring. Also, G₂ may have a substituent. G₂ more preferably represents a 5- to 8-membered aromatic heterocyclic ring and, when G₂ represents a 5- to 8-membered aromatic heterocyclic ring, it is a monocyclic ring or a condensed ring. Particularly preferably, G₂ represents a substituted or unsubstituted, 6-membered aromatic heterocyclic ring and, most preferably, G₁ represents a substituent selected from a group of the substituents represented by (3)-1 to (3)-6 among the following general formula (3):

General formula (3)

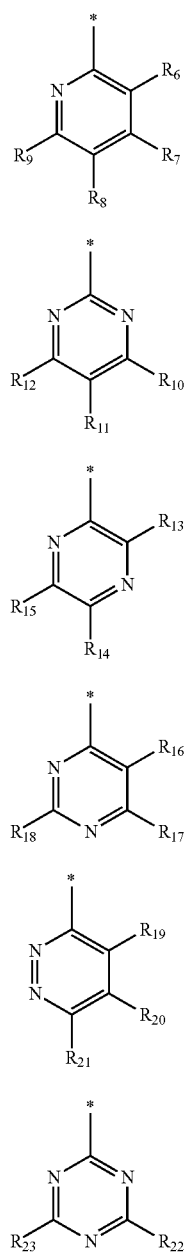

In the general formula (3), $R_6$ to $R_{23}$ each independently represents a hydrogen atom, a hydroxyl group, an amino group, a straight or branched alkyl group containing from 1 to 4 carbon atoms, a cycloalkyl group containing from 5 to 8 carbon atoms, an acyl group containing from 1 to 5 carbon atoms, an alkenyl group containing from 2 to 4 carbon atoms, an alkynyl group containing from 2 to 4 carbon atoms, an alkyloxy group containing from 1 to 4 carbon atoms, an alkylamino group containing from 1 to 8 carbon atoms, an alkyloxycarbonyl group containing from 2 to 5 carbon atoms, an amido group containing from 1 to 5 carbon atoms, an aralkyl group containing from 7 to 10 carbon atoms, a 5- to 8-membered, saturated or unsaturated hydrocarbon ring, or a 5- to 8-membered, saturated or unsaturated heterocyclic ring. When $R_6$ to $R_{23}$ each independently represents a 5- to 8-membered, saturated or unsaturated hydrocarbon ring or a 5- to 8-membered, saturated or unsaturated heterocyclic ring, it is a monocyclic ring or a condensed ring. Also, when $R_6$ to $R_{23}$ may further have a substituent, they may or may not have a substituent. More preferably, $R_6$ to $R_{23}$ each independently represents a hydrogen atom, a hydroxyl group, an amino group, a straight or branched alkyl group containing from 1 to 4 carbon atoms, an acyl group containing from 1 to 5 carbon atoms, an alkyloxy group containing from 1 to 4 carbon atoms, an alkylamino group containing from 1 to 8 carbon atoms, an alkyloxycarbonyl group containing from 2 to 5 carbon atoms, or an amido group containing from 1 to 5 carbon atoms. Of these, a hydrogen atom, a hydroxyl group, an amino group, a methyl group, a methyloxy group, a methylamino group, and an acetamido group are particularly preferred.

$R_6$ to $R_{21}$ each may be connected to each other and, in such cases, $R_6$ to $R_{21}$ represent preferably non-metallic atoms necessary for forming a 5- to 7-membered hydrocarbon ring or a 5- to 7-membered heterocyclic ring, more preferably non-metallic atoms necessary for forming a 6-membered aromatic hydrocarbon ring or a 6-membered aromatic heterocyclic ring.

To illustrate the heterocyclic group represented by G₂ in the general formula (4) without restricting the substitution position, there can be illustrated a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, and a sulfolanyl group.

Preferred examples of the heterocyclic group include a pyridyl group, a pyrazinyl group, a pyrimidinyl group, a pyridazinyl group, and a triazinyl group, with a pyridyl group, a pyrimidinyl group, and a triazinyl group being particularly preferred.

When foregoing G₂ is a group which can further have a substituent, examples of the substituent include those which have been illustrated with respect to $R_1$, $R_2$, $R_3$, Y, Z, and G in the foregoing general formula (1).

When $R_1$, $R_2$, $R_3$, Y, and Z each represents a divalent group, preferred examples of the divalent group include an alkylene group (for example, methylene, ethylene, propylene, butylene, or pentylene), an alkenylene group (for example, ethenylene or propenylene), an alkynylene group (for example, ethynylene or propynylene), an arylene group (for example, phenylene or naphthylene), a divalent heterocyclic group (for example, a 6-chloro-1,3,5-triazine-2,4-diyl group, a pyrimidine-2,4-diyl group, a pyrimidine-4,6-diyl group, a quinoxaline-2,3-diyl group, or a pyridazine-3,6-diyl group), —O—, —CO—, —NR'— (R' represents a hydrogen atom, an alkyl group, or an aryl group), —S—, —SO$_2$—, —SO—, or a combination thereof (for example, —NHCH$_2$CH$_2$NH— or —NHCONH—).

The alkylene group, alkenylene group, alkynylene group, arylene group, divalent heterocyclic group, and the alkyl or aryl group of R' may have a substituent.

Examples of the substituent include those which have been illustrated with respect to $R_1$, $R_2$, $R_3$, Y, Z, and G in the foregoing general formula (1).

The alkyl and aryl groups of the above-described R' are the same as those substituent examples which have been illustrated with respect to the alkyl or aryl group represented by $R_1$, $R_2$, $R_3$, Y, Z, and G.

More preferred is an alkylene group containing 6 or less carbon atoms, an alkenylene group containing 6 or less carbon atoms, an alkynylene group containing 6 or less carbon atoms, an arylene group containing from 6 to 10 carbon atoms, a divalent heterocyclic group, —S—, —SO—, —SO$_2$— or a combination thereof (for example, —SCH$_2$CH$_2$S— or —SCH$_2$CH$_2$CH$_2$S—).

When G2 represents a divalent group, the divalent group is preferably a divalent heterocyclic group (for example, a 6-chloro-1,3,5-triazine-2,4-diyl group, a pyrimidine-2,4-diyl group, a pyrimidine-4,6-diyl group, a quinoxaline-2,3-diyl group, or a pyridazine-3,6-diyl group).

The divalent heterocyclic group may have a substituent.

As examples of the substituent, there can be illustrated the same substituents as those which have been illustrated with respect to $R_1$, $R_2$, $R_3$, Y, Z, and G in the general formula (1).

The divalent linking group contains preferably a total of from 0 to 20 carbon atoms, more preferably a total of from 0 to 15 carbon atoms, most preferably from 0 to 10 carbon atoms.

When $R_1$, $R_2$, $R_3$, Y, and Z each represents a trivalent group, the trivalent group is preferably a trivalent hydrocarbon group, a trivalent heterocyclic group, >N—, or a combination thereof and a divalent group (for example, >NCH$_2$CH$_2$NH— or >NCONH—).

When $G_2$ represents a trivalent group, the trivalent group is preferably a trivalent heterocyclic group (for example, a 1,3, 5-triazine-2,4,6-triyl group or a pyrimidine-2,4,6-triyl group).

The trivalent linking group contains preferably a total of from 0 to 20 carbon atoms, more preferably a total of from 0 to 15 carbon atoms, most preferably from 0 to 10 carbon atoms.

Regarding a preferred combination of the groups in the pigment of the invention represented by the general formula (4), compounds wherein at least one of the various groups is the aforesaid preferred group are preferred, compounds wherein more of the various groups are the aforesaid preferred groups are more preferred, and compounds wherein all of the groups are the aforesaid preferred groups are most preferred.

Particularly preferred combinations as an azo pigment of the invention represented by the general formula (4) include the following (i) to (vii).

(i) n is an integer of from 2 to 4, preferably an integer of 2 or 3, more preferably 2.

(ii) $R_1$ and $R_2$ each independently represents a hydrogen atom, a straight or branched alkyl group containing from 1 to 6 carbon atoms, an alkenyl group containing from 2 to 6 carbon atoms, an alkynyl group containing from 2 to 6 carbon atoms, a substituted or unsubstituted, 5- to 8-membered aryl group, or a substituted or unsubstituted, 5- to 8-membered heterocyclic group, more preferably a hydrogen atom, a straight or branched alkyl group containing from 1 to 4 carbon atoms, or a substituted or unsubstituted, 5- to 8-membered aryl group, most preferably a methyl group, a t-butyl group, or a substituted or unsubstituted 5- to 8-membered aryl group.

(iii) Y represents preferably a hydrogen atom, a straight or branched alkyl group containing from 1 to 6 carbon atoms, a straight or branched alkenyl group containing from 2 to 6 carbon atoms, a straight or branched alkynyl group containing from 2 to 6 carbon atoms, a carbamoyl group containing from 1 to 6 carbon atoms, an alkoxycarbonyl group containing from 1 to 6 carbon atoms, a substituted or unsubstituted, 5- to 8-membered aryl group, or a substituted or unsubstituted, 5- to 8-membered heterocyclic group, more preferably a hydrogen atom, a straight or branched alkyl group containing from 1 to 4 carbon atoms, a carbamoyl group containing from 1 to 4 carbon atoms, an alkoxycarbonyl group containing from 1 to 4 carbon atoms, or a substituted or unsubstituted, 5- to 8-membered aryl group, most preferably a hydrogen atom, a methyl group, or a substituted or unsubstituted, 5- or 6-membered aryl group.

(iv) $R_3$ represents preferably a hydrogen atom or a monovalent substituent, more preferably a hydrogen atom, a methyl group, an ethyl group, an ethenyl group, or an ethynyl group, most preferably a hydrogen atom.

(v) Z represents preferably a cyano group, an acyl group containing from 2 to 6 carbon atoms, an acyloxy group containing from 2 to 6 carbon atoms, a carbamoyl group containing from 1 to 8 carbon atoms, an alkyloxycarbonyl group containing from 2 to 8 carbon atoms, an aryloxycarbonyl group containing from 7 to 12 carbon atoms, a nitro group, an alkylsulfinyl group containing from 1 to 6 carbon atoms, an arylsulfinyl group containing from 6 to 10 carbon atoms, an alkylsulfonyl group containing from 1 to 6 carbon atoms, an arylsulfonyl group containing from 6 to 10 carbon atoms, a sulfamoyl group containing from 0 to 9 carbon atoms, a halogenated alkyl group containing from 1 to 6 carbon atoms, a halogenated aryl group containing from 1 to 6 carbon atoms, a halogenated alkyloxy group containing from 1 to 6 carbon atoms, a halogenated alkylthio group containing from 1 to 6 carbon atoms, a halogenated aryloxy group containing from 6 to 12 carbon atoms, or a 5- to 8-membered heterocyclic group, more preferably a cyano group, an alkyloxycarbonyl group containing from 2 to 8 carbon atoms, an alkylsulfonyl group containing from 1 to 6 carbon atoms, an arylsulfonyl group containing from 6 to 10 carbon atoms, or a sulfamoyl group containing from 0 to 8 carbon atoms, most preferably a cyano group.

(vi) X represents preferably a hetero atom, more preferably a nitrogen atom, an oxygen atom, a sulfur atom, or a selenium atom, particularly preferably a nitrogen atom, an oxygen atom, or a sulfur atom, most preferably a nitrogen atom.

(vii) $G_2$ represents preferably a 5- to 8-membered, saturated or unsaturated heterocyclic ring and, when $G_2$ represents a 5- to 8-membered, saturated or unsaturated heterocyclic ring, the ring is a monocyclic ring or a condensed ring. Also, when $G_2$ may further have a substituent, $G_2$ may or may not have a substituent. When $G_2$ represents a 5-membered unsaturated heterocyclic ring, the ring has two or more nitrogen atoms within the ring. Further, $G_1$ more preferably represents a substituted or unsubstituted, 5- to 8-membered aromatic heterocyclic ring and, when $G_2$ represents a substituted or unsubstituted, 5- to 8-membered aromatic heterocyclic ring, the ring is a monocyclic ring or a condensed ring. When $G_2$ represents a 5-membered aromatic heterocyclic ring, the ring has two or more nitrogen atoms within the ring. $G_2$ particularly preferably represents a substituted or unsubstituted, 6-membered aromatic heterocyclic ring, most preferably represents a substituent selected from a group of the substituents represented by (3)-1 to (3)-6 among the following general formula (3).

General formula (3)

(3)-1
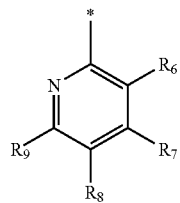

(3)-2
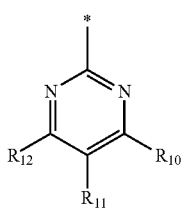

(3)-3
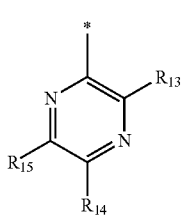

(3)-4
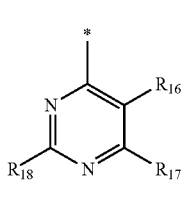

(3)-5
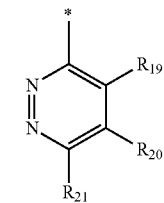

(3)-6
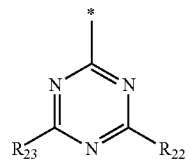

$R_6$ to $R_{23}$ each independently represents a hydrogen atom, a hydroxyl group, an amino group, a straight or branched alkyl group containing from 1 to 4 carbon atoms, a cycloalkyl group containing from 5 to 8 carbon atoms, an acyl group containing from 1 to 5 carbon atoms, an alkenyl group containing from 2 to 4 carbon atoms, an alkynyl group containing from 2 to 4 carbon atoms, an alkyloxy group containing from 1 to 4 carbon atoms, an alkylamino group containing from 1 to 8 carbon atoms, an alkyloxycarbonyl group containing from 2 to 5 carbon atoms, an amido group containing from 1 to 5 carbon atoms, an aralkyl group containing from 7 to 10 carbon atoms, a 5- to 8-membered, saturated or unsaturated hydrocarbon ring, or a 5- to 8-membered, saturated or unsaturated heterocyclic ring. When $R_6$ to $R_{23}$ each independently represents a 5- to 8-membered, saturated or unsaturated hydrocarbon ring or a 5- to 8-membered, saturated or unsaturated heterocyclic ring, it is a monocyclic ring or a condensed ring. Also, $R_6$ to $R_{23}$ may further have a substituent. More preferably, $R_6$ to $R_{23}$ each independently represents a hydrogen atom, a hydroxyl group, an amino group, a straight or branched alkyl group containing from 1 to 4 carbon atoms, an acyl group containing from 1 to 5 carbon atoms, an alkyloxy group containing from 1 to 4 carbon atoms, an alkylamino group containing from 1 to 8 carbon atoms, an alkyloxycarbonyl group containing from 2 to 5 carbon atoms, or an amido group containing from 1 to 5 carbon atoms. Of these, a hydrogen atom, a hydroxyl group, an amino group, a methyl group, a methyloxy group, a methylamino group, and an acetamido group are particularly preferred.

$R_6$ to $R_{21}$ each may be connected to each other and, in such cases, $R_6$ to $R_{21}$ represent preferably non-metallic atoms necessary for forming a 5- to 7-membered hydrocarbon ring or a 5- to 7-membered heterocyclic ring, more preferably non-metallic atoms necessary for forming a 6-membered aromatic hydrocarbon ring or a 6-membered aromatic heterocyclic ring.

The invention includes in its scope tautomers of the azo pigments represented by the general formula (4). Although the general formula (4) is shown in the form of limiting structure among several tautomer forms which are possible in view of chemical structure, the azo pigment may be tautomers of other structure than the shown one, and may be used as a mixture containing plural tautomers. For example, with the pigment represented by the general formula (4), azo-hydrazone tautomers represented by the following general formula (4') can be considered.

The invention also includes in its scope tautomers of the azo pigments represented by the following general formula (4') which is a tautomer of the azo pigment represented by the general formula (4).

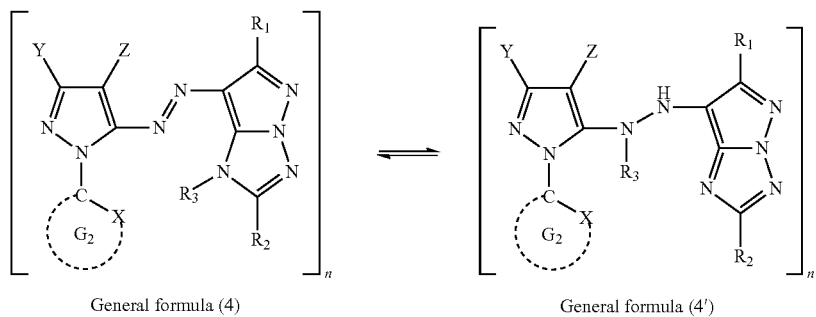

General formula (4)     General formula (4')

$R_1$, $R_2$, $R_3$, X, Y, Z, and $G_2$ in the general formula (4') are the same as defined with respect to $R_1$, $R_2$, $R_3$, X, Y, Z, and $G_2$ in the general formula (4).

The azo pigments represented by the foregoing general formula (2) are preferably azo pigments represented by the following general formula (5).

The azo pigments represented by the general formula (5), tautomers, salts, and hydrates thereof will be described in detail hereinafter.

General formula (5)

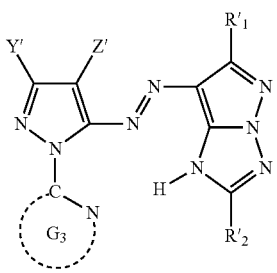

In the general formula (5), $R'_1$, $R'_2$, Y', and Z' are respectively the same as defined for $R'_1$, $R'_2$, Y', and Z' in the general formula (2). $G_3$ represents non-metallic atoms necessary for forming a 5- or 6-membered, nitrogen-containing aromatic heterocyclic ring. When $G_3$ represents a 5- to 6-membered, nitrogen-containing aromatic heterocyclic ring, it represents a monocyclic ring or a condensed ring. $G_3$ may have a substituent. When $G_3$ represents a 5-membered, nitrogen-containing aromatic heterocyclic ring, the ring contains two or more nitrogen atoms in the ring.

$R'_1$, $R'_2$, Y', Z', and $G_3$ in the foregoing general formula (5) will be described in more detail hereinafter.

$R'_1$, $R'_2$, and Y' are respectively the same as those exemplified for $R'_1$, $R'_2$, and Y' in the foregoing general formula (2), and preferred examples are also the same as described there.

Z' is the same as those exemplified for Z in the foregoing general formula (1), and preferred examples are also the same as described there.

$G_3$ in the general formula (5) preferably represents a 5- or 6-membered, nitrogen-containing aromatic heterocyclic ring and, when $G_3$ represents a 5- or 6-membered, nitrogen-containing aromatic heterocyclic ring, it is a monocyclic ring or a condensed ring. Also, when $G_3$ may have a substituent, $G_3$ may or may not have a substituent. $G_3$ more preferably represents a substituted or unsubstituted, 6-membered, nitrogen-containing aromatic heterocyclic ring. Particularly, $G_3$ represents most preferably a substituent selected from a group of the substituents represented by (3)-1 to (3)-6 among the following general formula (3):

General formula (3)

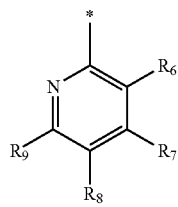
(3)-1

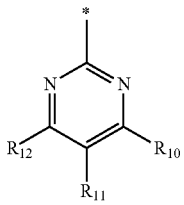
(3)-2

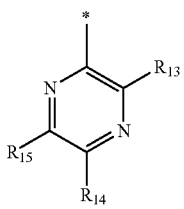
(3)-3

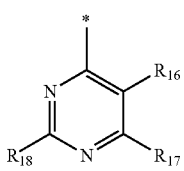
(3)-4

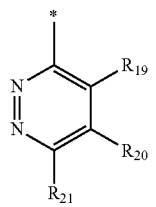
(3)-5

(3)-6

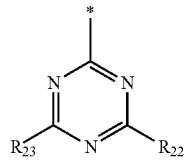

In the general formula (3), $R_6$ to $R_{23}$ each independently represents a hydrogen atom, a hydroxyl group, an amino group, a straight or branched alkyl group containing from 1 to 4 carbon atoms, a cycloalkyl group containing from 5 to 8 carbon atoms, an acyl group containing from 1 to 5 carbon atoms, an alkenyl group containing from 2 to 4 carbon atoms, an alkynyl group containing from 2 to 4 carbon atoms, an alkyloxy group containing from 1 to 4 carbon atoms, an alkylamino group containing from 1 to 8 carbon atoms, an alkyloxycarbonyl group containing from 2 to 5 carbon atoms, an amido group containing from 1 to 5 carbon atoms, an aralkyl group containing from 7 to 10 carbon atoms, a 5- to 8-membered, saturated or unsaturated hydrocarbon ring, or a 5- to 8-membered, saturated or unsaturated heterocyclic ring. When $R_6$ to $R_{23}$ each independently represents a 5- to 8-membered, saturated or unsaturated hydrocarbon ring or a 5- to 8-membered, saturated or unsaturated heterocyclic ring, it is a monocyclic ring or a condensed ring. Also, $R_6$ to $R_{23}$ may further have a substituent. More preferably, $R_6$ to $R_{23}$ each independently represents a hydrogen atom, a hydroxyl group, an amino group, a straight or branched alkyl group containing from 1 to 4 carbon atoms, an acyl group containing from 1 to 5 carbon atoms, an alkyloxy group containing from 1 to 4 carbon atoms, an alkylamino group containing from 1 to 8 carbon atoms, an alkyloxycarbonyl group containing from 2 to 5 carbon atoms, or an amido group containing from 1 to 5 carbon atoms. Of these, a hydrogen atom, a hydroxyl group, an amino group, a methyl group, a methyloxy group, a methylamino group, and an acetamido group are particularly preferred.

$R_6$ to $R_{21}$ each may be connected to each other and, in such cases, $R_6$ to $R_{21}$ represent preferably non-metallic atoms necessary for forming a 5- to 7-membered hydrocarbon ring or a 5- to 7-membered heterocyclic ring, more preferably non-metallic atoms necessary for forming a 6-membered aromatic hydrocarbon ring or a 6-membered aromatic heterocyclic ring.

To illustrate the heterocyclic group represented by $G_3$ in the general formula (5) without restricting the substitution position, there can be illustrated a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a pyrazolyl group, an imidazolyl group, a benzimidazolyl group, a triazolyl group, an oxazolyl group, a benzoxazolyl group, a thiadiazolyl group, an isoxazolyl group, a benzisoxazolyl group, a pyrrolidinyl group, a piperidinyl group, a piperazinyl group, an imidazolidinyl group, and a sulfolanyl group.

Preferred examples of the heterocyclic group include a pyridyl group, a pyrazinyl group, a pyrimidinyl group, a pyridazinyl group, and a triazinyl group, with a pyridyl group, a pyrimidinyl group, and a triazinyl group being particularly preferred.

Regarding a preferred combination of the groups in the pigment of the invention represented by the general formula (5), compounds wherein at least one of the various groups is the aforesaid preferred group are preferred, compounds wherein more of the various groups are the aforesaid preferred groups are more preferred, and compounds wherein all of the groups are the aforesaid preferred groups are most preferred.

Particularly preferred combinations as an azo pigment of the invention represented by the general formula (5) include the following (i) to (iv).

(i) $R'_1$ and $R'_2$ each independently represents preferably a hydrogen atom, a straight or branched alkyl group containing from 1 to 4 carbon atoms, a straight or branched alkenyl group containing from 2 to 4 carbon atoms, a straight or branched alkynyl group containing from 2 to 4 carbon atoms, an aralkyl group containing from 7 to 9 carbon atoms, a 5- to 8-membered, saturated or unsaturated hydrocarbon ring group, or a 5- to 8-membered, saturated or unsaturated heterocyclic group. When either $R'_1$ or $R'_2$ represents a 5- to 8-membered, saturated or unsaturated hydrocarbon ring group or a 5- to 8-membered, saturated or unsaturated heterocyclic group, it is a monocyclic ring or a condensed ring and, when it may have a substituent, it may or may not have a substituent. $R'_1$ and $R'_2$ each independently represents more preferably a hydrogen atom, a straight or branched alkyl group containing from 1 to 4 carbon atoms, a 5- to 8-membered, saturated or unsaturated hydrocarbon ring group, or a 5- to 8-membered, saturated or unsaturated heterocyclic group. When either $R'_1$ or $R'_2$ represents a 5- to 8-membered, saturated or unsaturated hydrocarbon ring group or a 5- to 8-membered, saturated or unsaturated heterocyclic group, it is a monocyclic ring or a condensed ring and, when it may have a substituent, it may or may not have a substituent. Of these, a methyl group, a t-butyl group, a substituted or unsubstituted, 5- or 6-membered aryl group, and a substituted and unsubstituted, 5- or 6-membered aromatic heterocyclic group are most preferred.

(ii) Y' represents preferably a hydrogen atom, a straight or branched alkyl group containing from 1 to 4 carbon atoms, a straight or branched alkenyl group containing from 2 to 4 carbon atoms, a straight or branched alkynyl group containing from 2 to 4 carbon atoms, an aralkyl group containing from 7 to 9 carbon atoms, a 5- to 8-membered, saturated or unsaturated hydrocarbon ring group, or a 5- to 8-membered, saturated or unsaturated heterocyclic group. When Y' represents a 5- to 8-membered, saturated or unsaturated hydrocarbon ring group or a 5- to 8-membered, saturated or unsaturated heterocyclic group, it is a monocyclic ring or a condensed ring and, when it may have a substituent, it may or may not have a substituent. Of these, a hydrogen atom, a straight or branched alkyl group containing from 1 to 4 carbon atoms, a 5- to 8-membered, saturated or unsaturated hydrocarbon ring group, and a 5- to 8-membered, saturated or unsaturated heterocyclic group are more preferred. When Y' represents a 5- to 8-membered, saturated or unsaturated hydrocarbon ring group or a 5- to 8-membered, saturated or unsaturated heterocyclic group, it is a monocyclic ring or a condensed ring and, when it may have a substituent, it may or may not have a substituent. Of these, a hydrogen atom, a methyl group, a t-butyl group, a substituted or unsubstituted, 6-membered aromatic hydrocarbon group, and a substituted or unsubstituted, 6-membered aromatic heterocyclic group are most preferred.

(iii) Z' represents preferably a cyano group, an acyl group containing from 2 to 6 carbon atoms, an acyloxy group containing from 2 to 6 carbon atoms, a carbamoyl group containing from 1 to 8 carbon atoms, an alkyloxycarbonyl group containing from 2 to 8 carbon atoms, an aryloxycarbonyl group containing from 7 to 12 carbon atoms, a nitro group, an alkylsulfinyl group containing from 1 to 6 carbon atoms, an arylsulfinyl group containing from 6 to 10 carbon atoms, an alkylsulfonyl group containing from 1 to 6 carbon atoms, an arylsulfonyl group containing from 6 to 10 carbon atoms, a sulfamoyl group containing from 0 to 9 carbon atoms, a halogenated alkyl group containing from 1 to 6 carbon atoms, a halogenated aryl group containing from 1 to 6 carbon atoms, a halogenated alkyloxy group containing from 1 to 6 carbon atoms, a halogenated alkylthio group containing from 1 to 6 carbon atoms, a halogenated aryloxy group containing from 6 to 12 carbon atoms, or a 5- to 8-membered heterocyclic group, more preferably a cyano group, an alkyloxycarbonyl group containing from 2 to 8 carbon atoms, an alkylsulfonyl group containing from 1 to 6 carbon atoms, an arylsulfonyl group containing from 6 to 10 carbon atoms, or a sulfamoyl group containing from 0 to 8 carbon atoms, most preferably a cyano group.

(iv) $G_3$ represents preferably a 5- or 6-membered, nitrogen-containing aromatic heterocyclic ring and, when $G_3$ represents a 5- or 6-membered, nitrogen-containing aromatic heterocyclic ring, the ring is a monocyclic ring or a condensed ring. Also, $G_3$ may have a substituent. Further, $G_3$ more preferably represents a substituted or unsubstituted, 6-membered nitrogen-containing aromatic heterocyclic ring, and most preferably represents a substituent selected from a group of the monovalent substituents represented by (3)-1 to (3)-6 among the foregoing general formula (3).

In the general formula (3), $R_6$ to $R_{23}$ each independently represents a hydrogen atom, a hydroxyl group, an amino group, a straight or branched alkyl group containing from 1 to 4 carbon atoms, a cycloalkyl group containing from 5 to 8 carbon atoms, an acyl group containing from 1 to 5 carbon atoms, an alkenyl group containing from 2 to 4 carbon atoms, an alkynyl group containing from 2 to 4 carbon atoms, an alkyloxy group containing from 1 to 4 carbon atoms, an alkylamino group containing from 1 to 8 carbon atoms, an alkyloxycarbonyl group containing from 2 to 5 carbon atoms, an amido group containing from 1 to 5 carbon atoms, an aralkyl group containing from 7 to 10 carbon atoms, a 5- to 8-membered, saturated or unsaturated hydrocarbon ring, or a 5- to 8-membered, saturated or unsaturated heterocyclic ring. When $R_6$ to $R_{23}$ each independently represents a 5- to 8-membered, saturated or unsaturated hydrocarbon ring or a 5- to 8-membered, saturated or unsaturated heterocyclic ring, it is a monocyclic ring or a condensed ring. Also, $R_6$ to $R_{23}$ may further have a substituent. More preferably, $R_6$ to $R_{23}$ each independently represents a hydrogen atom, a hydroxyl group, an amino group, a straight or branched alkyl group containing from 1 to 4 carbon atoms, an acyl group containing from 1 to 5 carbon atoms, an alkyloxy group containing from 1 to 4 carbon atoms, an alkylamino group containing from 1 to 8 carbon atoms, an alkyloxycarbonyl group containing from 2 to 5 carbon atoms, or an amido group containing from 1 to 5 carbon atoms. Of these, a hydrogen atom, a hydroxyl group, an amino group, a methyl group, a methyloxy group, a methylamino group, and an acetamido group are particularly preferred.

$R_6$ to $R_{21}$ each may be connected to each other and, in such cases, $R_6$ to $R_{21}$ represent preferably non-metallic atoms necessary for forming a 5- to 7-membered hydrocarbon ring or a 5- to 7-membered heterocyclic ring, more preferably non-metallic atoms necessary for forming a 6-membered aromatic hydrocarbon ring or a 6-membered aromatic heterocyclic ring.

The invention includes in its scope tautomers of the azo pigments represented by the general formula (5). Although the general formula (5) is shown in the form of limiting structure among several tautomer forms which are possible in view of chemical structure, the azo pigment may be tautomers of other structure than the shown one, and may be used as a mixture containing plural tautomers. For example, with the pigment represented by the general formula (5), azo-hydrazone tautomers represented by the following general formula (5') can be considered.

The invention also includes in its scope tautomers of the azo pigments represented by the following general formula (5') which is a tautomer of the azo pigment represented by the general formula (5).

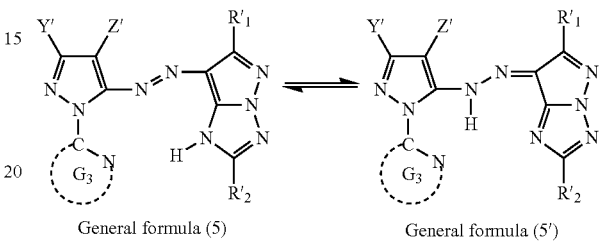

General formula (5)    General formula (5')

$R'_1$, $R'_2$, $Y'$, $Z'$, and $G_3$ in the general formula (5') are the same as defined with respect to $R'_1$, $R'_2$, $Y'$, $Z'$, and $G_3$ in the general formula (5).

The azo pigments represented by the foregoing general formula (2) are preferably azo pigments represented by the following general formula (6).

The azo pigments represented by the general formula (6), tautomers, salts, and hydrates thereof will be described in detail hereinafter.

General formula (6):

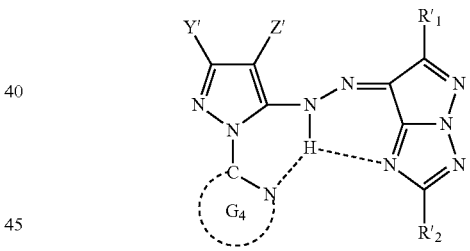

In the general formula (6), $R'_1$, $R'_2$, $Y'$, and $Z'$ are respectively the same as defined for $R'_1$, $R'_2$, and $Z'$ in the general formula (5), and preferred combinations thereof are also the same as described there. $G_4$ represents non-metallic atoms necessary for forming a 6-membered, nitrogen-containing aromatic heterocyclic ring, and the heterocyclic ring may be a monocyclic ring or a condensed ring.

With the azo pigments represented by the foregoing general formulae (1), (2), (4), (5), and (6), many tautomers can be considered. Of the azo pigments represented by the foregoing general formulae (1), (2), (4), (5), and (6), particularly preferred azo pigments are exemplified by those azo pigments which are represented by the foregoing general formula (6) as has been described hereinbefore.

The reason why this structure is preferred is that, as is shown by the general formula (6), nitrogen atoms, hydrogen atoms, and hetero atoms (oxygen atom of the carbonyl group or nitrogen atom of the amino group) constituting the heterocyclic rings contained in the azo pigment structure are liable to form at least one or more intramolecular crosslinking hydrogen bonds (intramolecular hydrogen bonds). As a result, flatness of the molecule is enhanced, the intramolecular and intermolecular interaction is improved, crystallinity of the azo pigment represented by the general formula (6) is enhanced (higher structure of the pigment becoming liable to be formed), and hence performances required as pigments, i.e., light fastness, heat stability, moist heat stability, water resistance, gas resistance, and/or solvent resistance, can markedly be improved, thus such pigments being most preferred.

The invention also relates to azo compounds represented by the general formula (2), and tautomers, salts, and hydrates thereof.

General formula (2)

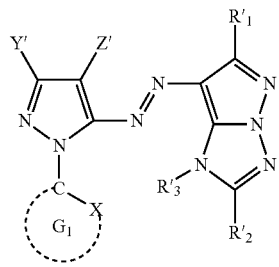

In the general formula (2), $R'_1$, $R'_2$, and Y' each independently represents a hydrogen atom, a straight or branched alkyl group containing from 1 to 4 carbon atoms, an alkenyl group containing from 2 to 4 carbon atoms, an alkynyl group containing from 2 to 4 carbon atoms, an acyl group containing from 1 to 5 carbon atoms, an aralkyl group containing from 7 to 9 carbon atoms, a 5- to 8-membered, saturated or unsaturated hydrocarbon ring group, or a 5- to 8-membered, saturated or unsaturated heterocyclic group. $R'_3$ represents a hydrogen atom or a monovalent substituent. Z' represents an electron-withdrawing group having a Hammett σp value of 0.2 or more. X represents a hetero atom adjacent to the carbon atom, and $G_1$ represents atoms necessary for forming a 5- to 8-membered, saturated or unsaturated heterocyclic ring. When any one of $R'_1$, $R'_2$, Y', and $G_1$ represents a 5- to 8-membered, saturated or unsaturated heterocyclic ring, it represents a monocyclic ring or a condensed ring. When any one of $R'_1$, $R'_2$, $R'_3$, Y', and $G_1$ represents a 5-membered unsaturated heterocyclic ring, it has two or more nitrogen atoms within the ring.

Examples of the substituents for the azo compounds of the invention represented by the general formula (2) and preferred combinations of the substituents are the same as illustrated with respect to the azo pigments represented by the general formula (2).

With the azo compounds represented by the general formula (2), those compounds are preferred wherein $G_1$ in the general formula (2) is selected from a group of the substituents represented by (3)-1 to (3)-6 among the following general formula (3).

General formula (3)

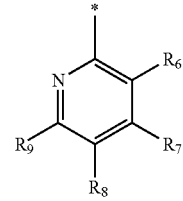
(3)-1

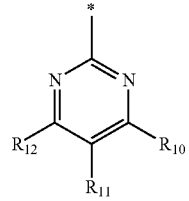
(3)-2

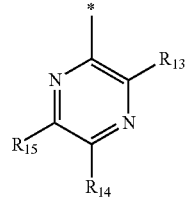
(3)-3

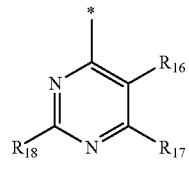
(3)-4

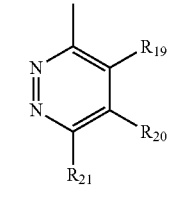
(3)-5

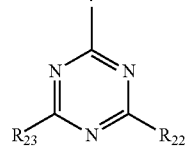
(3)-6

In the general formula (3), $R_6$ to $R_{23}$ each independently represents a hydrogen atom or a substituent. Also, $R_6$ to $R_{21}$ each may be connected to each other to form a ring.

With the azo compounds represented by the general formula (2), examples of the substituent groups represented by the general formulae (3)-1 to (3)-6 and preferred combinations of the substituents are the same as those illustrated with respect to the general formulae (3)-1 to (3)-6 in the azo pigments represented by the general formula (2).

The invention also relates to the azo compounds represented by the general formula (4), tautomers, salts, and hydrates thereof.

General formula (4)

$$\left[ \begin{array}{c} \text{structure with } Y, Z, R_1, R_2, R_3, G_2, X, N=N \end{array} \right]_n$$

In the general formula (4), n, $R_1$, $R_2$, $R_3$, Y, and Z are respectively the same as defined for n, $R_1$, $R_2$, $R_3$, Y, and Z in the general formula (1), and X represents a hetero atom adjacent to the carbon atom. $G_2$ represents atoms necessary for forming a 5- to 8-membered, saturated or unsaturated heterocyclic ring and, when n=2, the general formula (4) represents a dimer formed through $R_1$, $R_2$, $R_3$, Y, Z, or $G_2$. When n=3, the general formula (4) represents a trimer formed through $R_1$, $R_2$, $R_3$, Y, Z, or $G_2$. When n=4, the general formula (4) represents a tetramer formed through $R_1$, $R_2$, $R_3$, Y, Z, or $G_2$. When any one of $R_1$, $R_2$, $R_3$, Y, Z, or $G_2$ represents a 5- to 8-membered, saturated or unsaturated heterocyclic ring, it represents a monocyclic ring or a condensed ring.

With the azo compounds of the invention represented by the general formula (4), examples of the substituents and preferred combinations of the substituents are the same as those illustrated with respect to the azo pigments represented by the general formula (4).

The azo compounds represented by the general formula (4) are preferably those compounds wherein G2 in the general formula (4) is a group selected from the monovalent to trivalent substituent group represented by (3)-1 to (3)-6 of the following general formula (3).

General formula (3)

(3)-1
pyridine ring with $R_6$, $R_7$, $R_8$, $R_9$ (3)-2
pyrimidine ring with $R_{10}$, $R_{11}$, $R_{12}$ (3)-3
pyrazine ring with $R_{13}$, $R_{14}$, $R_{15}$ (3)-4
pyrimidine ring with $R_{16}$, $R_{17}$, $R_{18}$ (3)-5
pyridazine ring with $R_{19}$, $R_{20}$, $R_{21}$ (3)-6
triazine ring with $R_{22}$, $R_{23}$ In the general formula (3), $R_6$ to $R_{23}$ each independently represents a hydrogen atom or a substituent. Also, $R_6$ to $R_{21}$ each may be connected to each other to form a ring.

With the azo compounds represented by the general formula (4), examples of the substituent groups represented by the general formulae (3)-1 to (3)-6 and preferred combinations of the substituents are the same as those illustrated with respect to the general formulae (3)-1 to (3)-6 in the azo pigments represented by the general formula (4).

As the salts, hydrates, and tautomers of the azo compounds of the invention represented by the general formulae (2) and (4), there can be illustrated the same ones as the salts, hydrates, and tautomers of the azo pigments of the invention.

The novel azo compounds of the invention are useful as azo pigments. Also, the dispersion of the invention preferably contains at least one of the tautomers of the azo compounds represented by the general formula (2) or (4), salts, and hydrates thereof.

Specific examples of the azo pigments represented by the foregoing general formulae (1), (2), (4), (5), and (6) and the pigment dispersion, and the azo compounds represented by the general formulae (2) and (4) will be shown below. However, the azo pigments and the pigment dispersions to be used in the invention, and the azo compounds are not limited only to the following examples.

Although the structures of the following specific examples are shown in the form of limiting structure among several tautomer forms which are possible in view of chemical structure, it is needless to say that they may be other tautomer structures than the shown one.

(2)-1
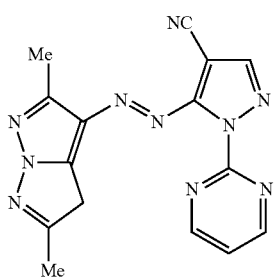
(2)-2
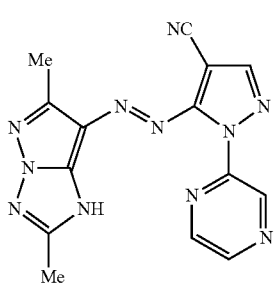
(2)-3
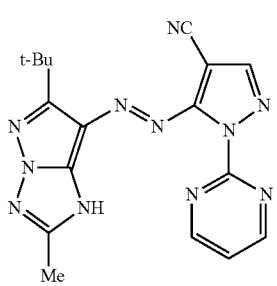
(2)-4
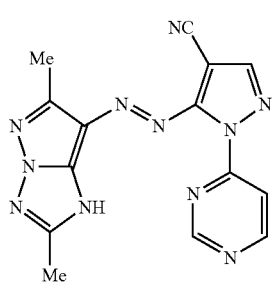
(2)-5
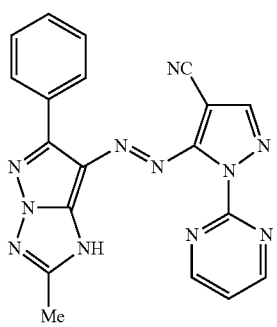
-continued
(2)-6
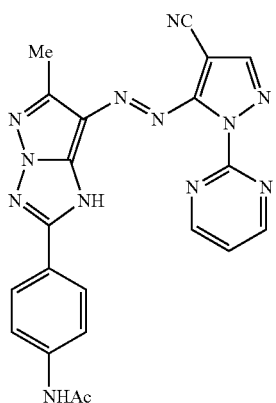
(2)-7
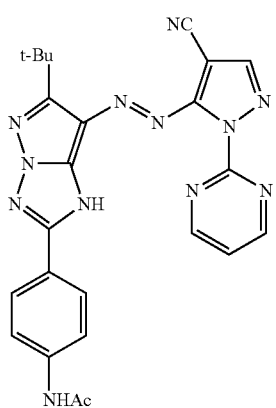
(2)-8
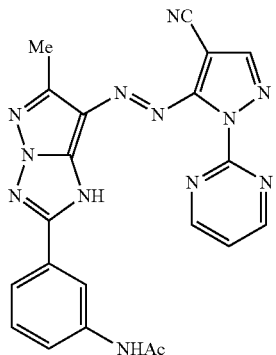
(2)-9
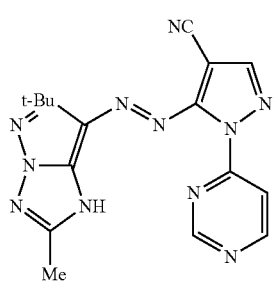

-continued
(2)-10
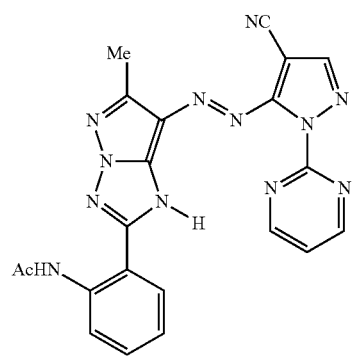
(2)-11
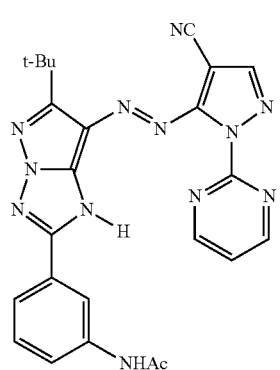
(2)-12
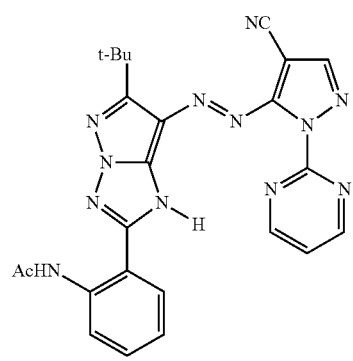
(2)-13
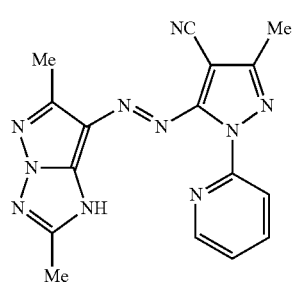
(2)-14
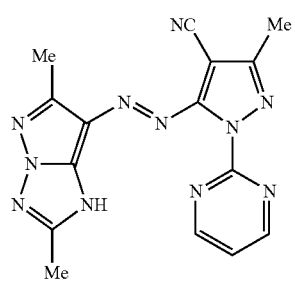
-continued
(2)-15
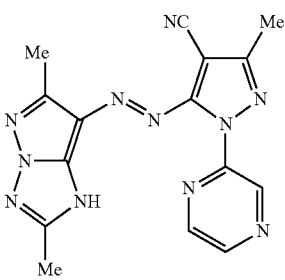
(2)-16
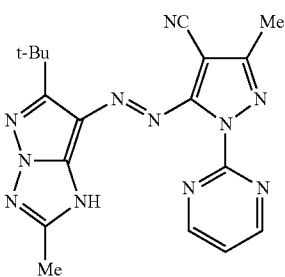
(2)-17
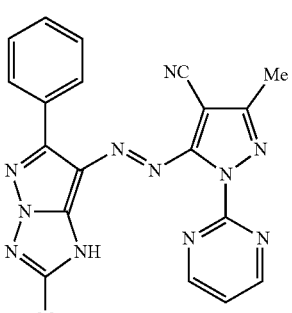
(2)-18
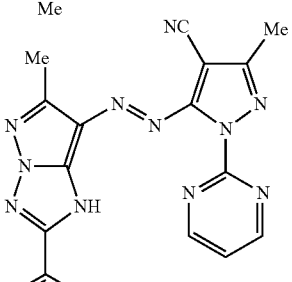
(2)-19
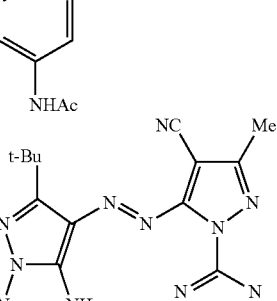

47
-continued
(2)-20
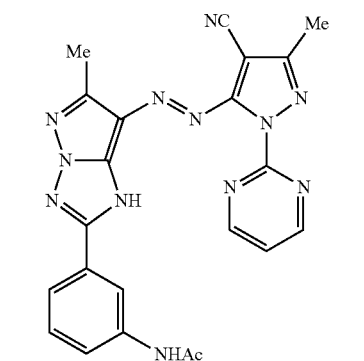
(2)-21
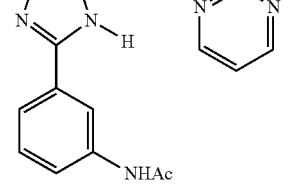
48
-continued
(2)-24
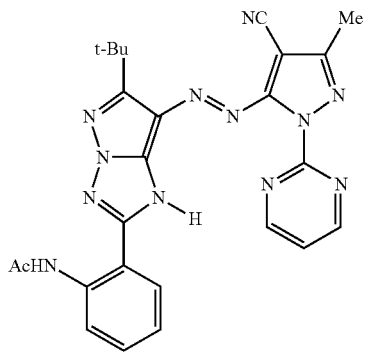
(2)-25
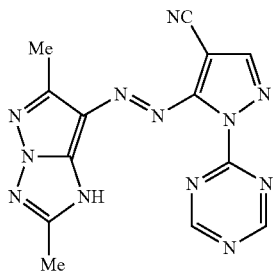
(2)-26
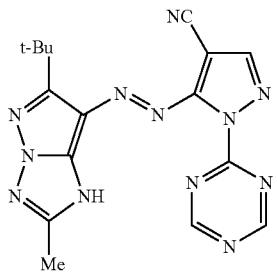
(2)-27
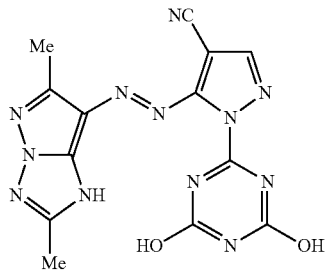
(2)-28
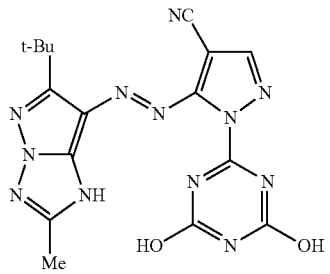

(2)-29
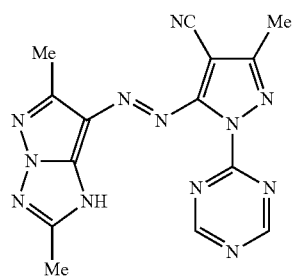
(2)-30
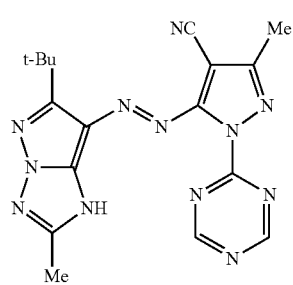
(2)-31
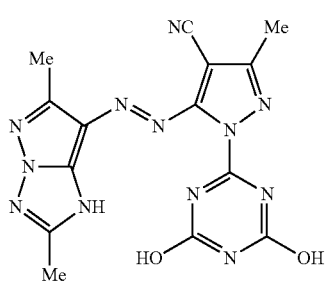
(2)-32
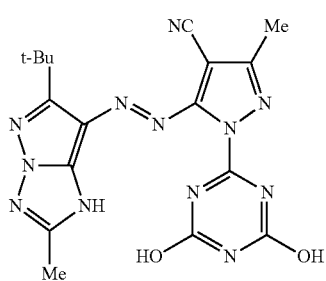
(2)-33
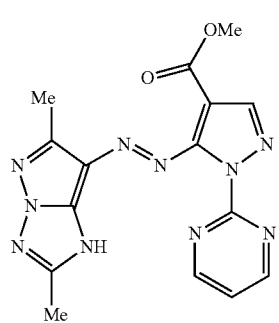
(2)-34
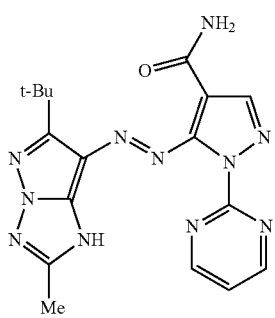
(2)-35
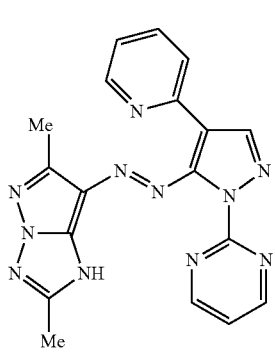
(2)-36
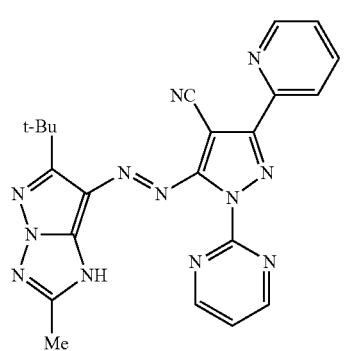
(2)-37
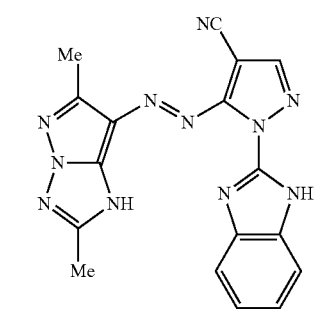
(2)-38
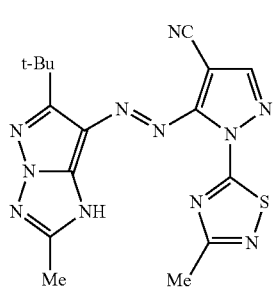

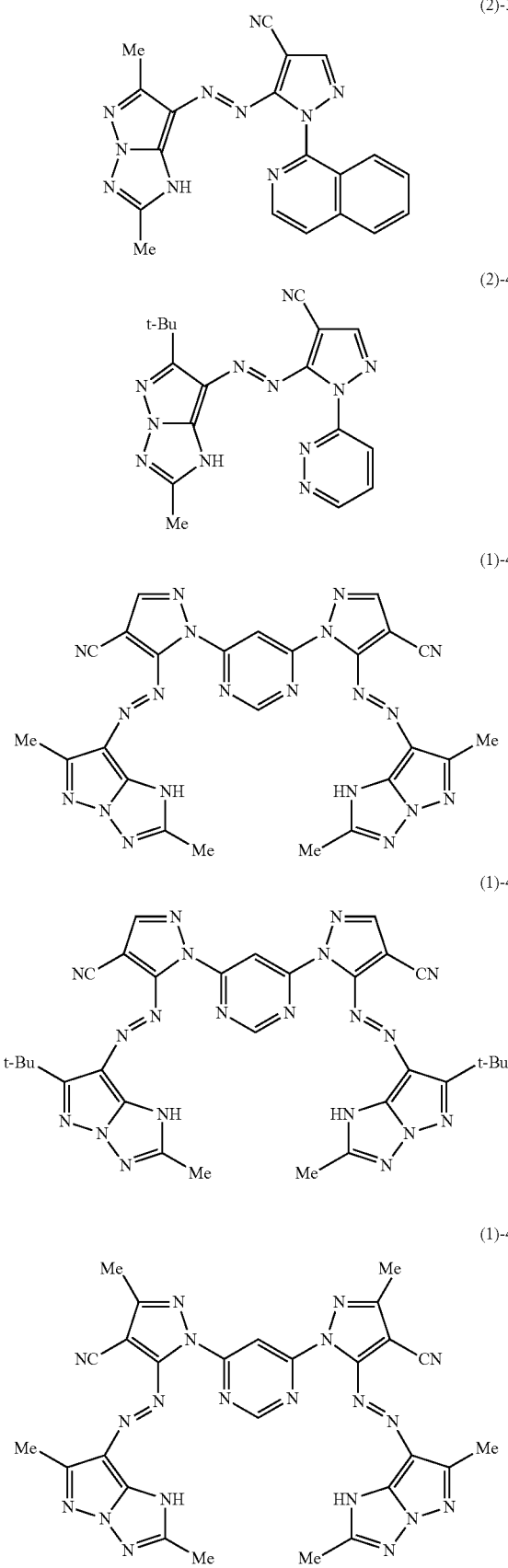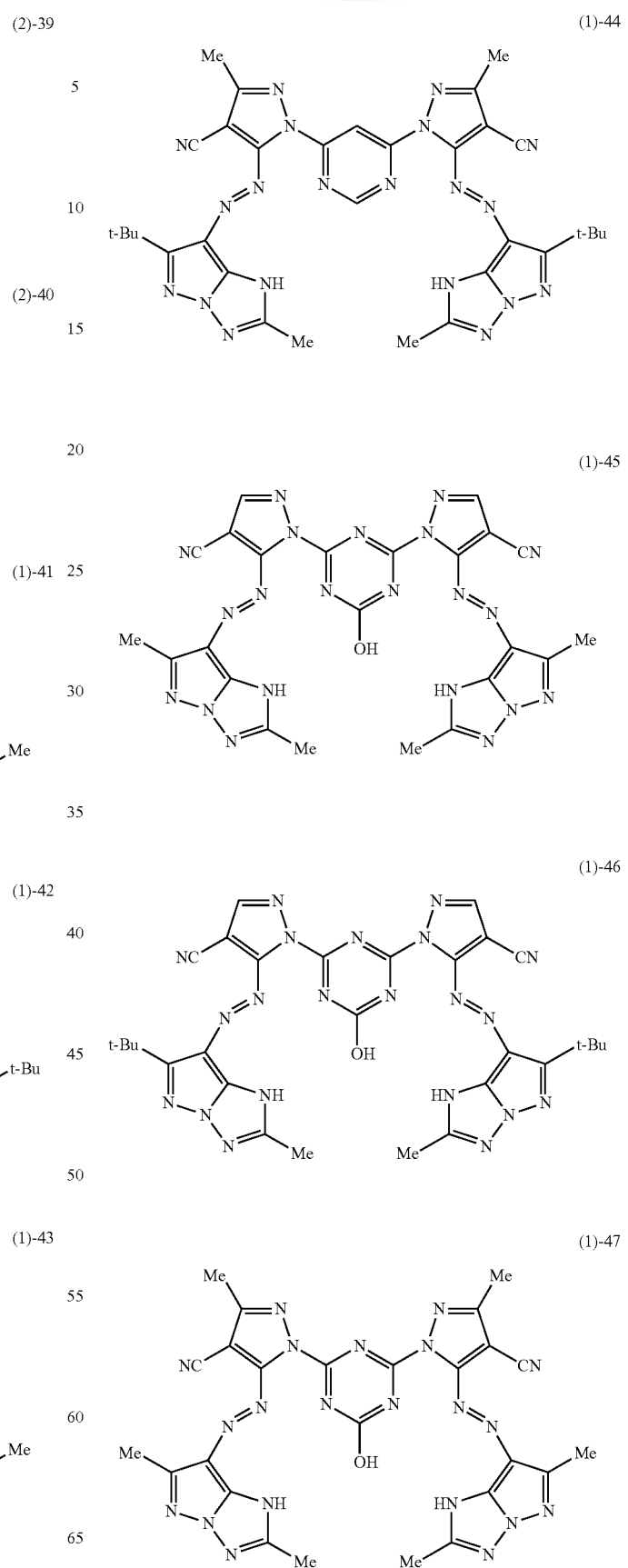

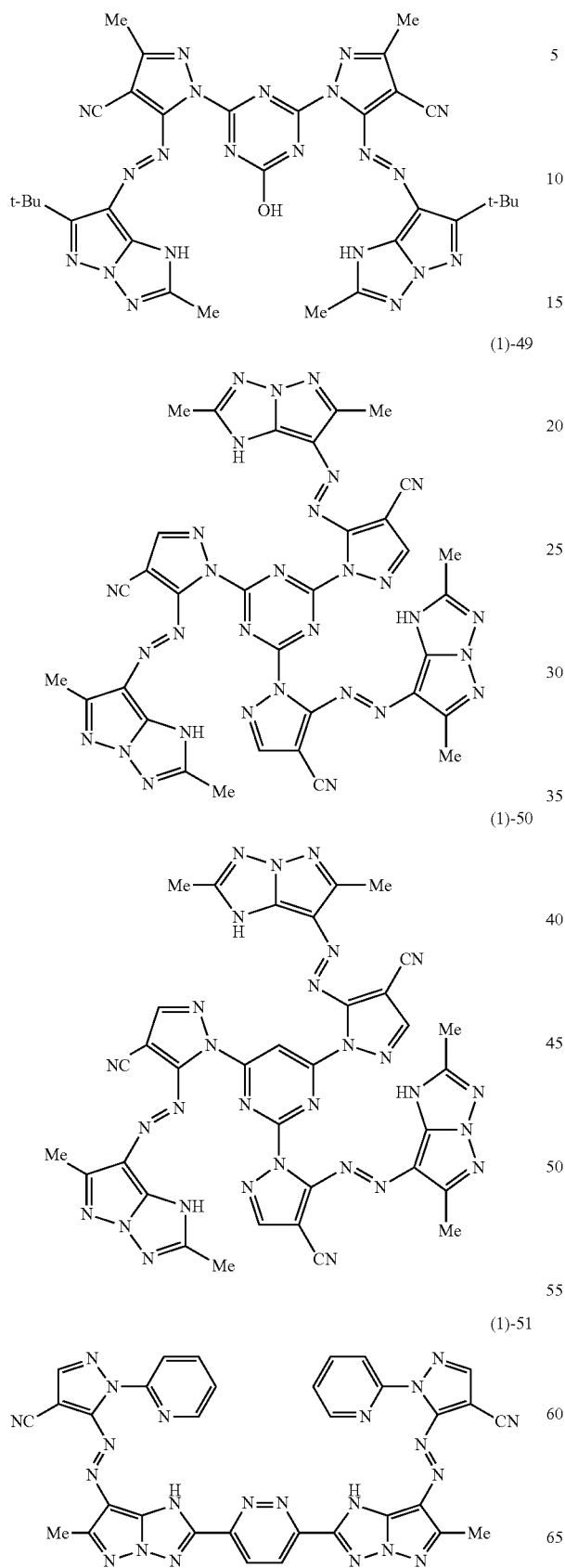
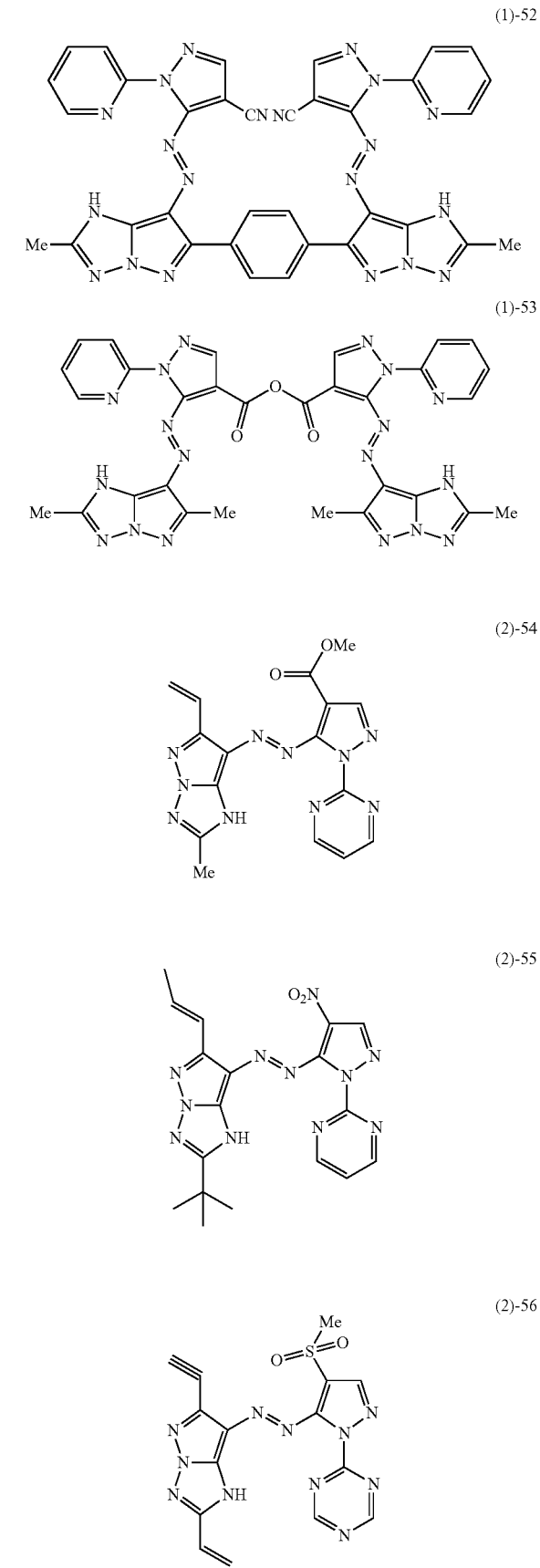

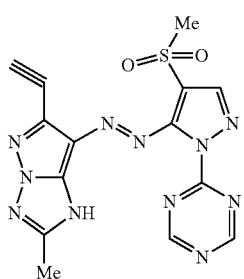

(2)-57

The pigments of the invention represented by the general formulae (1), (2), (4), (5), and (6) may have a chemical structure represented by the general formula (1), (2), (4), (5), or (6) or may be the tautomers thereof, and may be of any crystal form called polymorphic form.

Polymorphism means that crystals having the same chemical composition can be different from each other in the conformation of building block (molecules or ions) in the crystal. Chemical and physical properties of the pigments are decided by the crystal structure, and polymorphic forms of the same pigment can be discriminated from each other by rheology, color, and other color characteristics. Also, different polymorphic forms can be confirmed by X-Ray Diffraction (results of powder X-ray diffractiometry) or by X-Ray Analysis (results of X-ray analysis of crystal structure). In the case where the pigments of the invention represented by the general formulae (1), (2), (4), (5), and (6), exhibit polymorphism, they may be in any polymorphic forms and may be a mixture of two or more polymorphic forms. However, pigments wherein a single crystal form is predominant are preferred. That is, pigments not contaminated with polymorphic form crystals are preferred. The content of the azo pigment having a single crystal form is from 70% to 100%, preferably from 80% to 100%, more preferably from 90% to 100%, still more preferably from 95% to 100%, particularly preferably 100%, based on the entire azo pigment. When the azo pigment contains a single crystal form azo pigment as a major component, regularity of alignment of the pigment molecules is improved, and the intramolecular and intermolecular interaction is enhanced, thus a high-level three-dimensional network being easily formed. As a result, performances required for pigments, such as hue, light fastness, heat fastness, humidity fastness, fastness to an oxidative gas, and solvent resistance, are improved, thus the above-described content being preferred.

The mixing ratio of polymorphic forms in the azo pigment can be confirmed from values obtained by physicochemical measurement such as X-ray crystal structure analysis of single crystal, powder X-ray diffractometry (XRD), microscopic photography of the crystals (TEM), or IR (KBr method).

Control of the above-described tautomerism and/or polymorphism may be achieved by controlling production conditions upon coupling reaction.

With those which have acid groups among the azo pigments of the invention represented by the general formulae (1), (2), (4), (5), and (6), part or all of the acid groups may be in a salt form, or the pigment may be a mixture of a salt type pigment and a free acid type pigment. Examples of the salt type include salts of an alkali metal such as Na, Li, or K, salts of ammonium optionally substituted by an alkyl group or a hydroxyalkyl group, and salts of an organic amine. Examples of the organic amine include a lower alkyl amine, a hydroxyl-substituted lower alkyl amine, a carboxy-substituted lower alkyl amine, and a polyamine having from 2 to 10 alkyleneimine units containing from 2 to 4 carbon atoms. With these salt type pigments, they are not necessarily limited to one as to kind, but may be in a mixture of two or more thereof.

Further, as to the structure of the pigment to be used in the invention, in the case where plural acid groups exist in one molecule, the plural acid groups may be of a salt type or an acid type, and may be different from each other.

The azo pigments represented by the foregoing general formulae (1), (2), (4), (5), and (6) may be hydrates which contain water molecules within the crystal.

Synthesis of the azo pigments of the invention will be described in detail hereinafter.

The azo pigments of the invention can be synthesized by, for example, subjecting a diazonium salt prepared from a diazo component of the general formula (7) according to a known process to an azo coupling reaction with a coupling component of the general formula (8).

General formula (7)

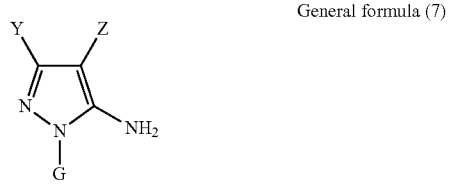

In the above general formula (7), Y, Z, and G are the same as defined for Y, Z, and G in the foregoing general formula (1).

General formula (8)

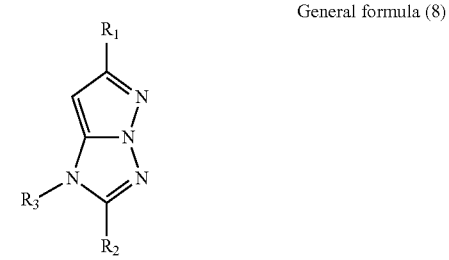

In the above general formula (8), $R_1$, $R_2$, and $R_3$ are the same as defined for $R_1$, $R_2$, and $R_3$ in the foregoing general formula (1).

Some of the heterocyclic amine (diazo component) represented by the amino compound of the above general formula (7) may be commercially available but, generally, the heterocyclic amines may be produced in a conventionally known manner by, for example, the process described in Japanese Patent No. 4,022,271. The diazotization reaction of the heterocyclic amine can be conducted, for example, by reacting it with a reagent such as sodium nitrite, nitrosylsulfonic acid, or isoamyl nitrite in an acidic solvent such as sulfuric acid, phosphoric acid, or acetic acid at a temperature of 15° C. or less for about 10 minutes to about 6 hours. The coupling reaction is preferably conducted by reacting the diazonium salt obtained by the above-mentioned process with the compound represented by the above general formula (8) at 40° C. or less, preferably 25° C. or less, for about 10 minutes to about 12 hours.

Regarding synthesis of the azo pigments of the general formulae (1) and (4) wherein n is 2 or more, they can be synthesized in the same manner as in the aforesaid scheme by synthesizing a starting material wherein a substitutable divalent, trivalent, or tetravalent substituent is introduced into $R_1$ to $R_3$, Y, Z, G, and the like in the general formula (7) or (8).

The reaction product may form precipitated crystals but, in general, water or an alcoholic solvent is added to the reaction solution to thereby precipitate crystals, and the precipitated crystals can be collected by filtration. Also, an alcoholic solvent and water may be added to the reaction solution to thereby precipitate crystals, and the precipitated crystals can be collected by filtration. The crystals thus collected by filtration are washed and dried, as needed, to obtain the azo pigment represented by the general formula (1).

Regarding processes for synthesizing the azo pigments of the general formulae (2), (5), and (6), the term "Y, Z, and G" of the foregoing general formula (7) in the above description shall be deemed to be replaced with "Y', Z', and $G_1$ (or $G_3$ or $G_4$)", respectively, and "$R_1$, $R_2$, and $R_3$" of the foregoing general formula (8) shall be deemed to be replaced with "$R'_1$, $R'_2$, and $R'_3$", respectively (here, $R'_1$, $R'_2$, $R'_3$, Y', Z', $G_1$, $G_3$, and $G_4$ are the same as defined for $R'_1$, $R'_2$, $R'_3$, Y', Z', $G_1$, $G_3$, and $G_4$ in the foregoing general formulae (2), (5), and (6), respectively.)

The compounds represented by the general formulae (1), (2), (4), (5), and (6) are obtained as a crude azo pigment by the above-described production process. In the case of using them as the pigment dispersion of the invention, they are preferably subjected to after-treatment. As methods of the after-treatment, there are illustrated, for example, a pigment particle-controlling step such as milling treatment (e.g., solvent-salt milling, salt milling, dry milling, solvent milling or acid pasting) or solvent heating treatment; and a surface-treating step using, for example, a resin, a surfactant or a dispersing agent.

The compounds of the invention represented by the general formulae (1), (2), (4), (5), and (6) are preferably subjected to the solvent heating treatment as the after-treatment. As a solvent to be used in the solvent heating treatment, there are illustrated, for example, water; aromatic hydrocarbon series solvents such as toluene and xylene; halogenated hydrocarbon series solvents such as chloroform, chlorobenzene, and o-dichlorobenzene; alcoholic solvents such as methanol, ethanol, isopropanol, and isobutanol; polar aprotic organic solvents such as acetone, N,N-dimethylformamide, N,N-dimethylacetamide, and N-methyl-2-pyrrolidone; glacial acetic acid; pyridine; and a mixture thereof. It is preferred to adjust the average particle size of the pigment to 0.01 µm to 1 µm by the after-treatment.

The compounds represented by the general formulae (1), (2), (4), (5), and (6) are obtained as a crude azo pigment (crude) by the above-described production process. In the case of using them as the pigments of the invention, they are preferably subjected to after-treatment. As methods of the after-treatment, there are illustrated, for example, a pigment particle-controlling step such as milling treatment (e.g., solvent-salt milling, salt milling, dry milling, solvent milling or acid pasting) or solvent heating treatment; and a surface-treating step using, for example, a resin, a surfactant or a dispersing agent.

The compounds of the invention represented by the general formulae (1), (2), (4), (5), and (6) are preferably subjected to the solvent heating treatment and/or the solvent-salt milling as the after-treatment.

As a solvent to be used in the solvent heating treatment, there are illustrated, for example, water, aromatic hydrocarbon series solvents such as toluene and xylene; halogenated hydrocarbon series solvents such as chlorobenzene and o-dichlorobenzene; alcoholic solvents such as isopropanol and isobutanol; polar aprotic organic solvents such as N,N-dimethylformamide, N,N-dimethylacetamide, and N-methyl-2-pyrrolidone; glacial acetic acid; pyridine; and a mixture thereof. An inorganic or organic acid or base may further be added to the above-described solvents. The temperature of the solvent heating treatment varies depending upon the desired primary particle size of the pigment, but is preferably from 40 to 150° C., more preferably from 60 to 100° C. The treating time is preferably from 30 minutes to 24 hours. As the solvent-salt milling, there is illustrated, for example, the procedure wherein a crude azo pigment, an inorganic salt, and an organic solvent which does not dissolve them are placed in a kneader, and knead-milling of the mixture is conducted therein. As the inorganic salt, water-soluble inorganic salts can preferably be used. For example, inorganic salts such as sodium chloride, potassium chloride, and sodium sulfate are preferably used. Also, it is more preferred to use inorganic salts having an average particle size of from 0.5 to 50 µm. The amount of the inorganic salt to be used is preferably a 3- to 20-fold amount by weight, more preferably a 5- to 15-fold amount by weight, based on the crude pigment. As the organic solvent, water-soluble organic solvents can preferably be used and, since the solvent becomes easily vaporizable due to an increase in temperature upon kneading, high-boiling solvents are preferred in view of safety. Examples of such organic solvents include diethylene glycol, glycerin, ethylene glycol, propylene glycol, liquid polyethylene glycol, liquid polypropylene glycol, 2-(methoxymethoxy)ethanol, 2-butoxyethanol, 2-(isopentyloxy)ethanol, 2-(hexyloxy)ethanol, diethylene glycol monomethyl ether, diethylene glycol monoethyl ether, diethylene glycol monobutyl ether, triethylene glycol, triethylene glycol monomethyl ether, 1-methoxy-2-propanol, 1-ethoxy-2-propanol, dipropylene glycol, dipropylene glycol monomethyl ether, dipropylene glycol monomethyl ether, dipropylene glycol, and a mixture thereof. The amount of the water-soluble organic solvent to be used is preferably a 0.1- to 5-fold amount based on the crude azo pigment. The kneading temperature is preferably from 20 to 130° C., particularly preferably from 40 to 110° C. As a kneader, there can be used, for example, a kneader and a mix muller.

[Pigment Dispersion]

The pigment dispersion of the invention is characterized in that it contains at least one of the azo pigments represented by the general formula (1), (2), (4), (5), and (6), the tautomers of the azo pigments, and the salts or hydrates thereof. Thus, there can be obtained a pigment dispersion having excellent coloring characteristics, durability, and dispersion stability.

The pigment dispersion of the invention may be aqueous or non-aqueous, but is preferably an aqueous pigment dispersion. As the aqueous liquid for dispersing the pigment in the aqueous pigment dispersion of the invention, a mixture containing water as a major component and, as needed, a hydrophilic organic solvent can be used. Examples of the hydrophilic organic solvent include alcohols such as methanol, ethanol, propanol, isopropanol, butanol, isobutanol, sec-butanol, t-butanol, pentanol, hexanol, cyclohexanol, and benzyl alcohol; polyhydric alcohols such as ethylene glycol, diethylene glycol, triethylene glycol, polyethylene glycol, propylene glycol, dipropylene glycol, polypropylene glycol, butylene glycol, hexanediol, pentanediol, glycerin, hexanetriol, and thiodiglycol; glycol derivatives such as ethylene glycol monomethyl ether, ethylene glycol monoethyl ether, ethylene glycol monobutyl ether, diethylene glycol monomethyl ether, diethylene glycol monobutyl ether, propylene glycol monomethyl ether, propylene glycol monobutyl ether, dipropylene glycol monomethyl ether, triethylene glycol monomethyl ether, ethylene glycol diacetate, ethylene glycol monomethyl ether acetate, triethylene glycol monomethyl ether, and ethylene glycol monophenyl ether; amines such as ethanolamine, diethanolamine, triethanolamine, N-methyldiethanolamine, N-ethyldiethanolamine, morpholine, N-ethylmorpholine, ethylenediamine, diethylenetriamine, triethylenetetramine, polyethyleneimine, and tetramethylpropylenediamine; formamide; N,N-dimethylformamide; N,N-dimethylacetamide; dimethylsulfoxide; sulfolane; 2-pyrrolidone; N-methyl-2-pyrrolidone; N-vinyl-2-pyrolidone; 2-oxazolidone; 1,3-dimethyl-2-imidazolidinone; acetonitrile; and acetone.

Further, the aqueous pigment dispersion of the invention may contain an aqueous resin. As the aqueous resin, there are illustrated water-soluble resins which dissolve in water, water-dispersible resins which can be dispersed in water, colloidal dispersion resins, and a mixture thereof. Specific examples of the aqueous resins include acryl series resins, styrene-acryl series resins, polyester resins, polyamide resins, polyurethane resins, and fluorine-containing resins.

Further, in order to improve dispersibility of the pigment and quality of image, a surfactant and a dispersing agent may be used. As the surfactant, there are illustrated anionic, nonionic, cationic, and amphoteric surfactants, and any of them may be used. However, anionic or nonionic surfactants are preferred to use. Examples of the anionic surfactants include aliphatic acid salts, alkyl sulfate salts, alkylbenzene sulfonate salts, alkylnaphthalene sulfonate salts, dialkyl sulfosuccinate salts, alkyldiaryl ether disulfonate salts, alkyl phosphate salts, polyoxyethylene alkyl ether sulfate salts, polyoxyethylene alkylaryl ether sulfate salts, naphthalenesulfonic acid-formalin condensates, polyoxyethylene alkyl phosphate salts, glycerol borate fatty acid esters, and polyoxyethylene glycerol fatty acid esters.

Examples of the nonionic surfactants include polyoxyethylene alkyl ethers, polyoxyethylene alkylaryl ethers, polyoxyethylene-oxypropylene block copolymers, sorbitan fatty acid esters, polyoxyethylene sorbitan fatty acid esters, polyoxyethylene sorbitol fatty acid esters, glycerin fatty acid esters, polyoxyethylene fatty acid esters, polyoxyethylene alkylamines, fluorine-containing surfactants, and silicon-containing surfactants.

The non-aqueous pigment dispersion of the invention comprises the pigment represented by the general formula (1), (2), (4), (5), or (6) dispersed in a non-aqueous vehicle. Examples of resin to be used as the non-aqueous vehicle include petroleum resin, casein, shellac, rosin-modified maleic acid resin, rosin-modified phenol resin, nitrocellulose, cellulose acetate butyrate, cyclized rubber, chlorinated rubber, oxidized rubber, rubber hydrochloride, phenol resin, alkyd resin, polyester resin, unsaturated polyester resin, amino resin, epoxy resin, vinyl resin, vinyl chloride, vinyl chloride-vinyl acetate copolymer, acryl resin, methacryl resin, polyurethane resin, silicone resin, fluorine-containing resin, drying oil, synthetic drying oil, styrene/maleic acid resin, styrene/acryl resin, polyamide resin, polyimide resin, benzoguanamine resin, melamine resin, urea resin, chlorinated polypropylene, butyral resin, and vinylidene chloride resin. It is also possible to use a photo-curable resin as the non-aqueous vehicle.

Examples of the solvents to be used in the non-aqueous vehicles include aromatic solvents such as toluene, xylene, and methoxybenzene; acetate series solvents such as ethyl acetate, butyl acetate, propylene glycol monomethyl ether acetate, and propylene glycol monoethyl ether acetate; propionate series solvents such as ethoxyethyl propionate; alcoholic solvents such as methanol and ethanol; ether series solvents such as butyl cellosolve, propylene glycol monomethyl ether, diethylene glycol ethyl ether, and diethylene glycol dimethyl ether; ketone series solvents such as methyl ethyl ketone, methyl isobutyl ketone, and cyclohexanone; aliphatic hydrocarbon series solvents such as hexane; nitrogen-containing compound series solvents such as N,N-dimethylformamide, N,N-dimethylacetamide, γ-butyrolactam, N-methyl-2-pyrrolidone, aniline, and pyridine; lactone series solvents such as γ-butyrolactone; and carbamic acid esters such as a 48:52 mixture of methyl carbamate and ethyl carbamate.

The pigment dispersion of the invention is obtained by dispersing the azo pigment and the aqueous or non-aqueous medium using a dispersing apparatus. As the dispersing apparatus which can be used, there are illustrated ball mill, sand mill, beads mill, roll mill, jet mill, attritor, an ultrasonic wave dispersing machine, and a disper.

In the invention, the volume-average particle size of the pigment in which is included the pigment dispersion is preferably from 10 nm to 250 nm. Additionally, the term "volume-average particle size of the pigment" means the particle size of the pigment itself or, in the case where an additive such as a dispersing agent is adhered to the pigment particles, means the size of the particle with the additive being adhered thereto. In the invention, as an apparatus for measuring the volume-average particle size of the pigment, a particle size analyzer of Nanotrac UPA (UPA-EX150; manufactured by Nikkiso Co., Ltd.) is used. The measurement is conducted according to a predetermined measuring method placing 3 ml of a pigment dispersion in a measuring cell. Additionally, with respect to parameters to be inputted upon measurement, an ink viscosity is used as a viscosity, and a pigment density is used as a density of the pigment.

The volume-average particle size of the pigment is more preferably from 20 nm to 250 nm, still more preferably from 20 nm to 230 nm. In case when the volume-average particle size of the particles in the pigment dispersion is less than 10 nm, storage stability might not be ensured in some cases whereas, in case when the volume-average particle size of the particles in the pigment dispersion exceeds 250 nm, the optical density might be reduced in some cases.

The content of the pigment contained in the pigment dispersion of the invention is preferably in the range of from 1 to 35% by weight, more preferably in the range of from 2 to 25% by weight. In case when the content is less than 1% by weight, a sufficient image density might not be obtained in some cases by using the pigment dispersion independently as an ink composition. In case when the content exceeds 35% by weight, the dispersion stability might be reduced in some cases.

A dispersion containing the azo compound of the invention can similarly contain the above-described components constituting the pigment dispersion, and a preferred content of the azo compound to be contained in the dispersion is also similar to that described with respect to the pigment dispersion.

As uses of the azo pigments and azo compounds of the invention, there are illustrated image recording materials for forming images, particularly color images. Specifically, there are illustrated inkjet system recording materials to be described in detail below, heat-sensitive recording materials, pressure-sensitive recording materials, recording materials for the electro-photographic system, transfer system silver halide light-sensitive materials, printing inks, and recording pens, preferably inkjet system recording materials, heat-sensitive recording materials, and recording materials for the electro-photographic system, more preferably inkjet system recording materials.

In addition, the pigments and the compounds can find application to color filters for recording and reproducing color images to be used in solid state imaging devices such as CCDs and in displays such as LCD and PDP and to a pigmenting solution for pigmenting various fibers.

[Coloring Composition]

The coloring composition of the invention means a coloring composition containing at least one kind of the azo pigments or azo compounds of the invention. The coloring composition of the invention can contain a medium and, in the case where a solvent is used as the medium, the composition is particularly appropriate as an ink composition for inkjet recording. The coloring composition of the invention can be prepared by using an oleophilic medium or an aqueous medium as the medium and dispersing the azo pigment of the invention in the medium. Preferably, the aqueous medium is used. The coloring composition of the invention includes an ink composition excluding the medium. The coloring composition of the invention may contain, as needed, other additives within the range of not spoiling the advantages of the invention. Examples of the other additives include known additives (described in JP-A-2003-306623) such as a drying-preventing agent (a wetting agent), an antifading agent, an emulsion stabilizer, a penetration accelerator, an ultraviolet ray absorbent, an antiseptic, an antifungal agent, a pH-adjusting agent, a surface tension-adjusting agent, an anti-foaming agent, a viscosity-adjusting agent, a dispersing agent, a dispersion stabilizer, a rust inhibitor, and a chelating agent. In the case of aqueous ink compositions, these various additives are added directly to the ink solution. In the case of oil based ink compositions, it is general to add to a dispersion after preparing the azo pigment dispersion, but they may be added to an oil phase or an aqueous phase upon preparation.

[Ink for Inkjet Recording]

Next, the ink of the invention for inkjet recording will be described below.

The ink of the invention for inkjet recording (hereinafter also referred to as "ink") contains the pigment dispersion described above, and is preferably prepared by mixing with a water-soluble solvent or water. However, in the case where no particular problems are involved, the pigment dispersion of the invention described above may be used as such.

In view of hue, color density, saturation, and transparency of an image formed on a recording medium, the content of the pigment dispersion in the ink of the invention is in the range of preferably from 1 to 100% by weight, particularly preferably from 3 to 20% by weight, most preferably from 3 to 10% by weight.

The azo pigment or azo compound of the invention is contained in an amount of from 0.1 part by weight to 20 parts by weight, more preferably from 0.2 part by weight to 10 parts by weight, still more preferably from 1 to 10 parts by weight, in 100 parts by weight of the ink composition of the invention. The ink of the invention may further contain other pigment in combination with the pigment of the invention. In the case of using two or more kinds of pigments, the total amount of the pigments is preferably within the above-described range.

The ink composition of the invention can be used for forming a full-color image as well as a mono-color image. In order to form the full-color image, a magenta tone ink, a cyan tone ink, and a yellow tone ink can be used and, further, a black tone ink can be used for adjusting tone.

Further, in the ink of the invention may be used other pigments in addition to the azo pigment of the invention. As yellow pigments to be applied, there are illustrated, for example, C.I.P.Y.-74, C.I.P.Y.-128, C.I.P.Y.-155, and C.I.P.Y.-213. As magenta pigments to be applied, there are illustrated C.I.P.V.-19 and C.I.P.R.-122. As cyan pigments to be applied, there are illustrated C.I. PB-15:3 and C.I.P.B-15:4. Apart from these pigments, any pigment may be used as each pigment. As a black color material, there can be illustrated a dispersion of carbon black as well as disazo, trisazo, and tetrazo pigments.

As the water-soluble solvents to be used in the ink of the invention, polyhydric alcohols, polyhydric alcohol derivatives, nitrogen-containing solvents, alcohols, and sulfur-containing solvents are used.

Specific examples of the polyhydric alcohols include ethylene glycol, diethylene glycol, propylene glycol, butylenes glycol, triethylene glycol, 1,5-pentanediol, 1,2,6-hexanetriol, and glycerin.

Examples of the polyhydric alcohol derivatives include ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, propylene glycol monobutyl ether, dipropylene glycol monobutyl ether, and an ethylene oxide adduct of diglycerin.

Also, examples of the nitrogen-containing solvents include pyrrolidone, N-methyl-2-pyrrolidone, cyclohexylpyrrolidone, and triethanolamine, examples of the alcohols include ethanol, isopropyl alcohol, butyl alcohol, and benzyl alcohol, and examples of the sulfur-containing solvents include thiodiethanol, thiodiglycerol, sulfolane, and dimethylsulfoxide. Besides, propylene carbonate and ethylene carbonate may also be used.

The water-soluble solvents to be used in the invention may be used alone or as a mixture of two or more thereof. As to the content of the water-soluble solvent, the solvent is used in an amount of from 1% by weight to 60% by weight, preferably from 5% by weight to 40% by weight, based on the total weight of the ink. In case when the content of the water-soluble solvent in the entire ink is less than 1% by weight, there might result an insufficient optical density in some cases whereas, in case when the content exceeds 60% by weight, there might result unstable jet properties of the ink liquid in some cases due to the large viscosity of the liquid.

The preferred physical properties of the ink of the invention are as follows. The surface tension of the ink is preferably from 20 mN/m to 60 mN/m, more preferably from 20 mN/m to 45 mN/m, still more preferably from 25 mN/m to 35 mN/m. In case when the surface tension is less than 20 mN/m, the liquid might, in some cases, overflow onto the nozzle surface of the recording head, thus normal printing not being performed. On the other hand, in case when the surface tension exceeds 60 mN/m, the ink might, in some cases, slowly penetrate into the recording medium, thus the drying time becoming longer.

Additionally, the surface tension is measured under the environment of 23° C. and 55% RH by using a Wilhelmy surface tension balance as is the same described above.

The viscosity of the ink is preferably from 1.2 mPa·s to 8.0 mPa·s, more preferably from 1.5 mPa·s to 6.0 mPa·s, still more preferably from 1.8 mPa·s to 4.5 mPa·s. In case when the viscosity is more than 8.0 mPa·s, ink ejection properties might, in some cases, be deteriorated. On the other hand, in case when the viscosity is less than 1.2 mPa·s, the long-term ejection properties might be deteriorated in some cases. Additionally, the viscosity (including that to be described hereinafter) is measured by using a rotational viscometer Rheomat 115 (manufactured by Contraves Co.) at 23° C. and a shear rate of 1,400 $s^{-1}$.

In addition to the above-mentioned individual components, water is added to the ink within an amount of providing the preferred surface tension and viscosity described above. The addition amount of water is not particularly limited, but is in the range of preferably from 10% by weight to 99% by weight, more preferably from 30% by weight to 80% by weight, based on the total weight of the ink composition.

Further, for the purpose of controlling characteristic properties such as improvement of ejection properties, there can be used, as needed, polyethyleneimine, polyamines, polyvinylpyrrolidone, polyethylene glycol, cellulose derivatives such as ethyl cellulose and carboxymethyl cellulose, polysaccharides and derivatives thereof, water-soluble polymers, polymer emulsions such as an acrylic polymer emulsion, a polyurethane series emulsion, and a hydrophilic latex, hydrophilic polymer gels, cyclodextrin, macrocyclic amines, dendrimers, crown ethers, urea and derivatives thereof, acetamide, silicone surfactants, and fluorine-containing surfactants.

Also, in order to adjust electrical conductivity and pH, there can be used compounds of alkali metals such as potassium hydroxide, sodium hydroxide, and lithium hydroxide; nitrogen-containing compounds such as ammonium hydroxide, triethanolamine, diethanolamine, ethanolamine, and 2-amino-2-methyl-1-propanol; compounds of alkaline earth metals such as calcium hydroxide; acids such as sulfuric acid, hydrochloric acid, and nitric acid; and salts between a strong acid and a weak alkali, such as ammonium sulfate. Besides, pH buffers, antioxidants, antifungal agents, viscosity-adjusting agents, electrically conductive agents, and ultraviolet ray absorbents may also be added as needed.

[Inkjet Recording Method, Inkjet Recording Apparatus, Ink Tank for Inkjet Recording, and Recorded Product]

The inkjet recording method of the invention is a method of forming an image on the surface of a recording medium by using an ink of the invention for inkjet recording, and ejecting the ink onto the surface of the recording medium from a recording head according to record signals.

Also, the inkjet recording apparatus of the invention is an apparatus wherein the ink of the invention for inkjet recording is used and a recording head capable of ejecting the ink (if necessary, a processing solution) onto the surface of a recording medium is provided, with the ink being ejected onto the surface of the recording medium from the recording head. Additionally, the inkjet recording apparatus of the invention can feed the ink to the recording head, and may be equipped with an ink tank for inkjet recording (hereinafter also referred to as "ink tank") which is removable from the main body of the inkjet recording apparatus. In this case, the ink of the invention is contained in the ink tank for inkjet recording.

As the inkjet recording apparatus of the invention, an ordinary inkjet recording apparatus equipped with a printing system capable of using the ink of the invention for inkjet recording can be utilized. In addition, there may be employed an inkjet recording apparatus having mounted thereon a heater or the like for controlling drying of the ink, or an inkjet recording apparatus equipped with a transfer mechanism which ejects (print) an ink and a processing solution onto an intermediate body, and then transfers the image on the intermediate body onto a recording medium such as paper.

Also, as the ink tank of the invention for inkjet recording, any of conventionally known ink tank can be utilized as long as it is removable from the inkjet recording apparatus equipped with a recording head and has a constitution that it can feed, in a state of being mounted on the inkjet recording apparatus, an ink to a recording head.

In view of the effect of reducing blurring and inter-color bleeding, it is preferred to employ a thermal inkjet recording system or a piezo inkjet recording system.

With the thermal inkjet recording system, an ink is heated upon ejection to have a low viscosity, and the temperature of the ink decreases when the ink reaches onto a recording medium, leading to a sharp increase in viscosity. This serves to provide the effect of reducing blurring and inter-color bleeding. On the other hand, with the piezo inkjet recording system, a liquid with high viscosity can be ejected and, since the liquid with high viscosity can suppress its spread in the direction of paper surface on a recording medium, it serves to provide the effect of reducing blurring and inter-color bleeding.

In the inkjet recording method (apparatus) of the invention, replenishment (feeding) of the ink to the recording head is conducted preferably from an ink tank filled with an ink liquid (including, as needed, a processing solution tank). This ink tank is preferably a cartridge system tank which is removable from the main body of the apparatus. Replenishment of the ink can be conducted with ease by exchanging the cartridge system ink tank.

The recorded products of the invention can be obtained by using the inkjet ink, and can preferably be obtained by employing the above-described inkjet recording method. According to such recorded products, there can be provided recorded products having excellent coloring characteristics and fastness.

EXAMPLES

The invention will be described in more detail by reference to Examples which, however, are not to be construed as limiting the invention. Additionally, in Examples, "parts" are by weight.

Example 1

In the present invention, the diazo component represented by the general formula (7) can be synthesized according to known processes (described in, for example, *Bioorganic & Medicinal Chemistry Letter*, 14 (2004), 2121-2125).

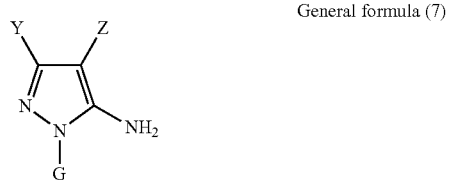

General formula (7)

In the above general formula (7), Y, Z, and G are respectively the same as defined for Y, Z, and G in the foregoing general formula (1).

In the invention, the coupling component represented by the general formula (8) can be synthesized according to, for example, the following route.

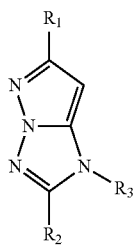

General formula (8)

In the above general formula (8), $R_1$, $R_2$, and $R_3$ are respectively the same as defined for $R_1$, $R_2$, and $R_3$ in the foregoing general formula (1).

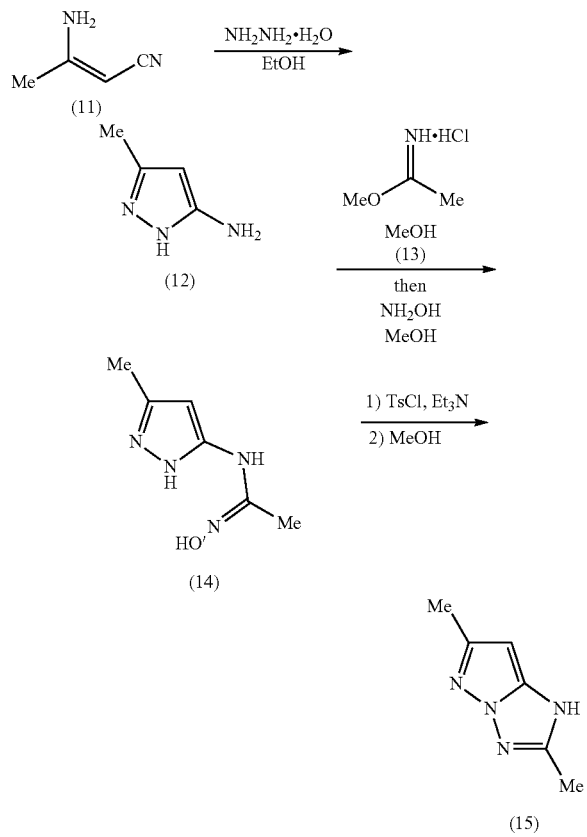

Synthesis of Compound (12)

58.6 parts of 3-aminocrotonnitrile (11) is dissolved in 310 parts (or ml) of ethanol at room temperature, and 35.7 parts of hydrous hydrazine is added thereto, followed by stirring the mixture at room temperature. The mixture is heated to an internal temperature of 65° C., and stirring is conducted for 12 hours. After cooling the mixture to room temperature, the solvent is distilled off under reduced pressure to obtain 69.0 parts of a brown oily compound (12). $^1$H NMR (400 MHz in CDCl$_3$; δ ppm; J Hz) 2.20 (3H, s), 5.42 (1H, s) MALDI-TOF-MS: 98.1 [M+H$^+$]

Synthesis of Compound (14)

50 parts of compound (12) is dissolved in 400 parts of methanol at room temperature. Separately, 60.3 parts of compound (13) is dissolved in 300 parts of methanol at room temperature and is cooled with ice to keep the internal temperature at 5° C. or lower. Then, the above-described methanol solution of compound (12) is dropwise added thereto over 1 hour with keeping the internal temperature at 5° C. or lower. After completion of the dropwise addition, the mixture is stirred for 3 hours at room temperature. Separately, 43 parts of hydroxylammonium chloride is suspended in 120 parts of methanol at room temperature, and the resulting suspension is cooled to an internal temperature of 5° C. or lower. 120 parts of a 28% methanol solution of sodium methoxide is dropwise added thereto over 40 minutes with keeping the internal temperature at 10° C. or lower. After completion of the dropwise addition and stirring for 30 minutes at 10° C. or lower, the internal temperature is increased to room temperature, followed by stirring for 30 minutes. A precipitated solid product is removed by filtration to obtain a methanol solution of hydroxylamine. After cooling the above-described reaction solution of compound (12) and compound (13) with ice to an internal temperature of 5° C. or lower, the above-described methanol solution of hydroxylamine is dropwise added to the reaction solution over 1 hour with keeping the internal temperature at 15° C. or lower and, after completion of the dropwise addition, the temperature of the reaction solution is increased to room temperature, followed by further stirring for 2 hours. A solid product precipitated is collected by filtration, spray-washed with 100 parts of water and 100 parts of ethyl acetate, and dried for 12 hours at room temperature to obtain 47 parts of compound (14) as a white solid product. $^1$H NMR (400 MHz in DMSO-d6; δ ppm; J Hz) 1.90 (3H, s), 2.15 (3H, s), 5.68 (1H, s), 7.57 (1H, s), 9.50 (1H, s) MALDI-TOF-MS: 155.1 [M+H$^+$]

Synthesis of Compound (15)

47 parts of compound (14) is suspended in 700 parts of acetonitrile at room temperature, and the resulting suspension is cooled with ice to an internal temperature of 5° C. or lower. 64 parts of p-toluenesulfonyl chloride is added thereto by portions with keeping the internal temperature at 10° C. or lower. After the exothermic reaction is subsided, 46.5 ml of triethylamine is added thereto over 30 minutes with keeping the internal temperature at 10° C. or lower, followed by stirring for 20 minutes at the same temperature. Then, the temperature of the mixture is increased to room temperature, followed by further stirring for 2 hours. Separately, 1,500 parts of a saturated aqueous solution of sodium chloride cooled to an internal temperature of 10° C. or lower with ice is prepared, and the above-described reaction solution is poured into the aqueous solution. After allowing to stand at the same temperature for 1 hour, precipitated crystals are collected by filtration, and spray-washed with 200 parts of cold water of 10° C. or lower in internal temperature and 150 parts of ethyl acetate to obtain a white solid product.

The thus-obtained solid product is suspended in 1,000 parts of methanol at room temperature, and is heated to an internal temperature of 65° C., followed by stirring for 1 hour. After cooling to room temperature, the solvent is distilled off under reduced pressure to obtain an oily product. This product is cooled with ice. Separately, 30 parts of saturated sodium hydrogen carbonate is dissolved in 300 parts of water and, under cooling with ice, the resulting solution is added by portions to the above-described oily product. Crystals precipitated are spray-washed with 100 parts of water and 100 parts of ethyl acetate, and dried at room temperature for 12 hours to obtain 18.3 parts of compound (15) as a yellow solid product. $^1$H NMR (400 MHz in DMSO-d6; δ ppm; J Hz) 2.20 (3H, s), 2.35 (3H, s), 5.48 (1H, s) MALDI-TOF-MS: 137.1 [M+H$^+$]

Example 2

Specific Illustrative Compound (2)-1

Specific illustrative compound (2)-1 is synthesized according to the following route.

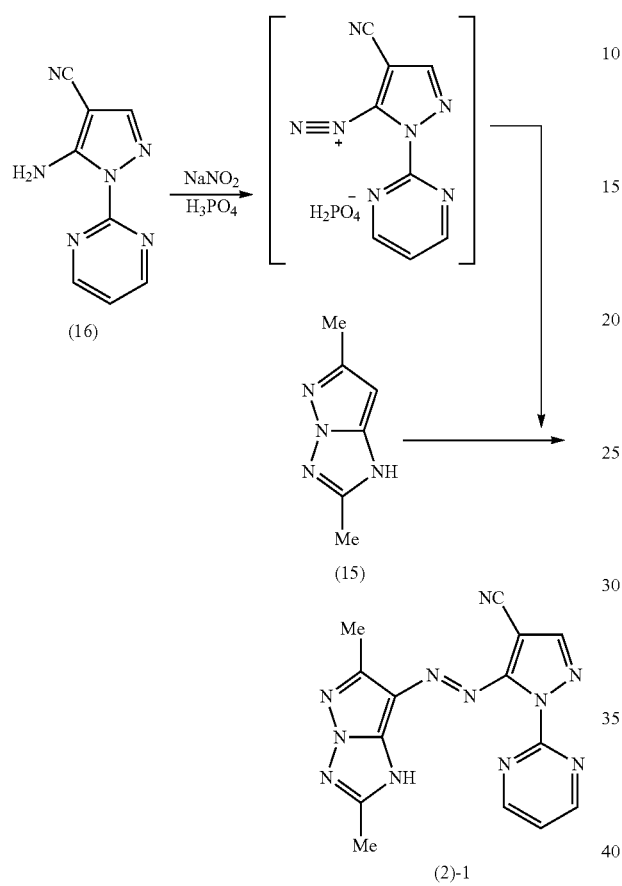

Synthesis of Pigment (2)-1

1.7 parts of compound (16) is added to 21 parts of phosphoric acid at room temperature, and the mixture is heated to an internal temperature of 60° C. to dissolve. This solution is cooled with ice and, while keeping the internal temperature at −5 to 0° C., 0.8 part of sodium nitrite is added thereto, followed by stirring at the same temperature for 1 hour to obtain a diazonium salt solution. Separately, 1 part of compound (15) is suspended in 50 parts of methanol, and the resulting suspension is cooled with ice to keep the internal temperature at 5° C. or lower. To this is gradually added the above-described diazonium salt solution in such manner that the internal temperature is kept at 5° C. or lower. After stirring the mixture at the same temperature for 1 hour, the ice bath is removed, followed by stirring the mixture for 1 hour at room temperature. Crystals precipitated are collected by filtration, and spray-washed with 50 parts of methanol, then sufficiently spray-washed with water. The thus-obtained crystals are added, without drying, to a mixture of 30 parts of methanol and 15 parts of water, and the mixture is heated to an internal temperature of 60° C. or higher, followed by stirring for 3 hours. Thereafter, the mixture is stirred for 1 hour under cooling in air and, after cooling to an internal temperature of room temperature, crystals precipitated are collected by filtration and washed with 30 parts of methanol. The crystals are dried for 12 hours at room temperature to obtain 2.3 parts of pigment (2)-1 of the invention. Yield: 93.2%. Infrared absorption spectrum (KBr method) of the pigment (2)-1 is shown in FIG. 1.

Example 3

Specific Illustrative Compound (2)-2

Specific illustrative compound (2)-2 is synthesized according to the following route.

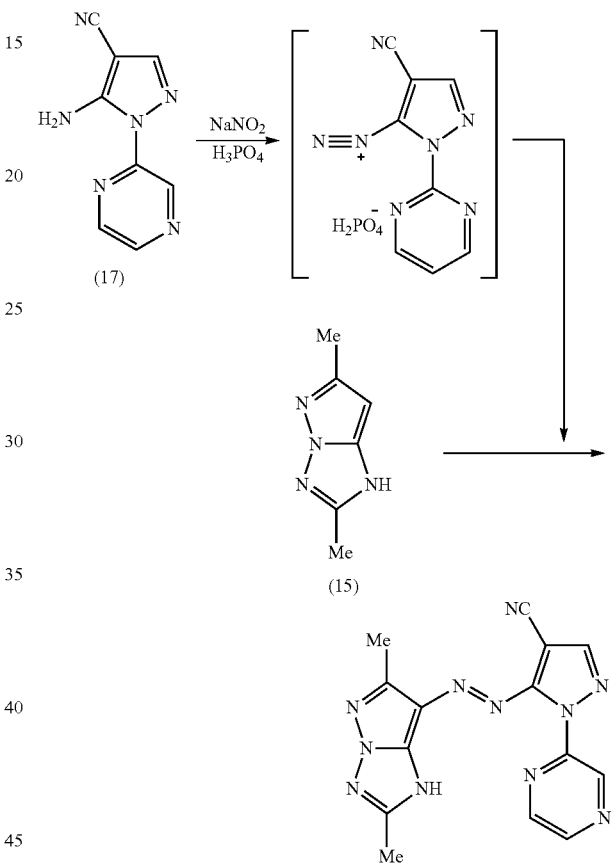

Synthesis of Pigment (2)-2

Figure 2:
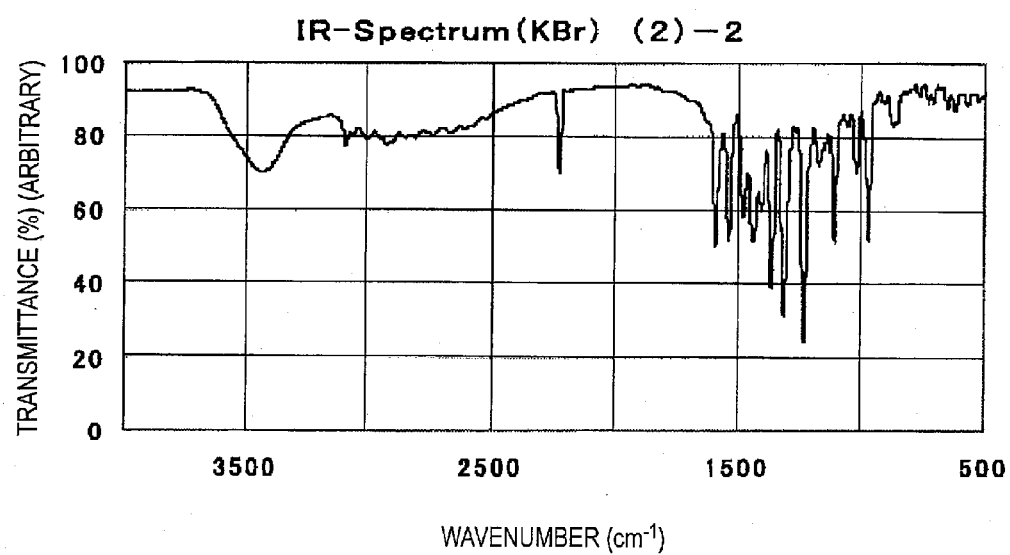
FIG. 2 is an infrared absorption spectrum of an illustrative compound (2)-2 of the azo pigment obtained in Example 3.

1.7 parts of compound (17) is added to 20 parts of phosphoric acid at room temperature, and the mixture is heated to an internal temperature of 60° C. to dissolve. This solution is cooled with ice and, while keeping the internal temperature at −5 to 0° C., 0.8 part of sodium nitrite is added thereto by portions, followed by stirring at the same temperature for 1 hour to obtain a diazonium salt solution. Separately, 1 part of compound (15) is suspended in 50 parts of methanol to prepare a suspension, and the resulting suspension is cooled with ice to keep the internal temperature at 5° C. or lower. To this is gradually added the above-described diazonium salt solution in such manner that the internal temperature is kept at 5° C. or lower. After stirring the mixture at the same temperature for 1 hour, the ice bath is removed, followed by stirring the mixture for 1 hour at room temperature. Crystals precipitated are collected by filtration, and spray-washed with 50 parts of methanol, then sufficiently spray-washed with water. The thus-obtained crystals are added, without drying, to a mixture of 30 parts of methanol and 15 parts of water, and the mixture is heated to an internal temperature of 65° C. under stirring for 3 hours. Thereafter, the mixture is stirred for 1 hour under cooling in air and, after cooling to an internal temperature of room temperature, crystals precipitated are collected by filtration and washed with 30 parts of methanol. The crystals are dried for 12 hours at room temperature to obtain 1.9 parts of pigment (2)-2 of the invention. Yield: 77.5%. Infrared absorption spectrum (KBr method) of the pigment (2)-2 is shown in FIG. 2.

Example 4

Specific Illustrative Compound (2)-3

Specific illustrative compound (2)-3 is synthesized according to the following route.

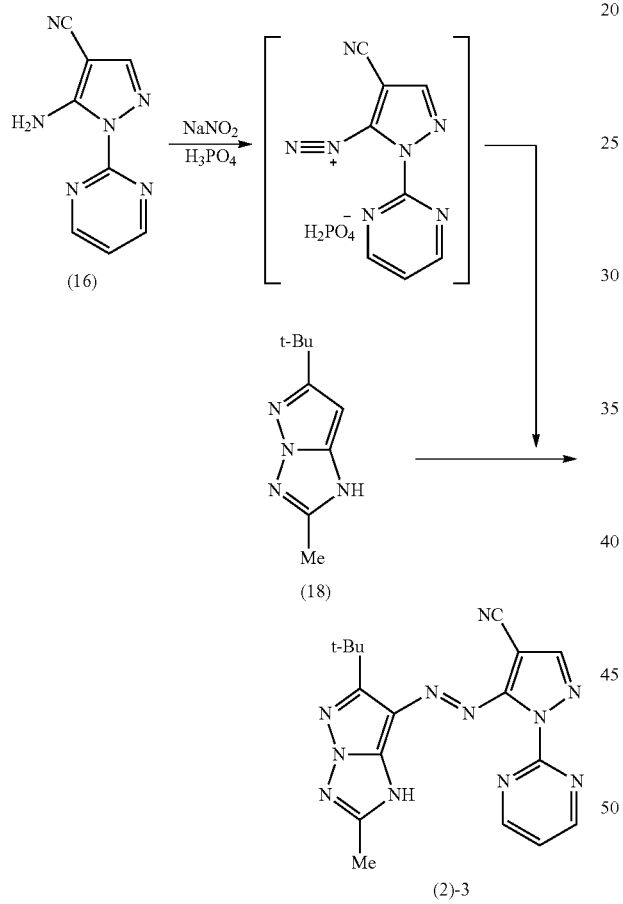

(2)-3

Synthesis of Pigment (2)-3

Figure 3:
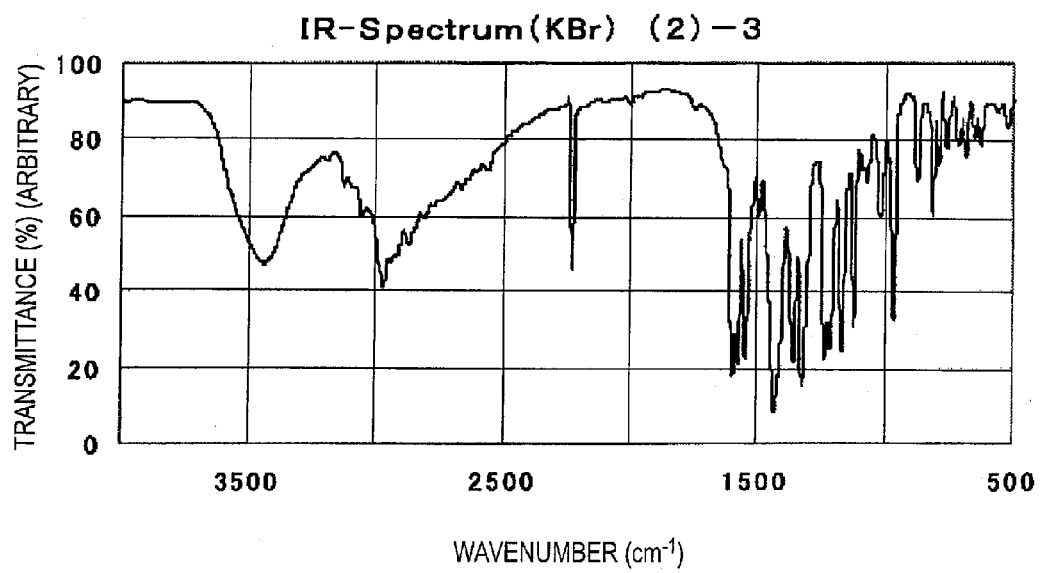
FIG. 3 is an infrared absorption spectrum of an illustrative compound (2)-3 of the azo pigment obtained in Example 4.

1.0 part of compound (16) is added to 12 parts of phosphoric acid at room temperature, and the mixture is heated to an internal temperature of 60° C. to dissolve. This solution is cooled with ice and, while keeping the internal temperature at −5 to 0° C., 0.5 part of sodium nitrite is added thereto, followed by stirring at the same temperature for 1 hour to obtain a diazonium salt solution. Separately, 0.8 part of compound (18) is suspended in 40 parts of methanol to prepare a suspension, and the resulting suspension is cooled with ice to keep the internal temperature at 5° C. or lower. To this is gradually added the above-described diazonium salt solution in such manner that the internal temperature is kept at 5° C. or lower. After stirring the mixture at the same temperature for 1 hour, the ice bath is removed, followed by stirring the mixture for 1 hour at room temperature. Crystals precipitated are collected by filtration, and spray-washed with 50 parts of methanol, then sufficiently spray-washed with water. The thus-obtained crystals are added, without drying, to a mixture of 30 parts of methanol and 15 parts of water, and the mixture is heated to an internal temperature of 65° C. under stirring for 3 hours. Thereafter, the mixture is stirred for 1 hour under cooling in air and, after cooling to an internal temperature of room temperature, crystals precipitated are collected by filtration and washed with 30 parts of methanol. The crystals are dried for 12 hours at room temperature to obtain 1.2 parts of pigment (2)-3 of the invention. Yield: 79.2%. Infrared absorption spectrum (KBr method) of the pigment (2)-3 is shown in FIG. 3.

Example 5

Specific Illustrative Compound (2)-5

Specific illustrative compound (2)-5 is synthesized according to the following route.

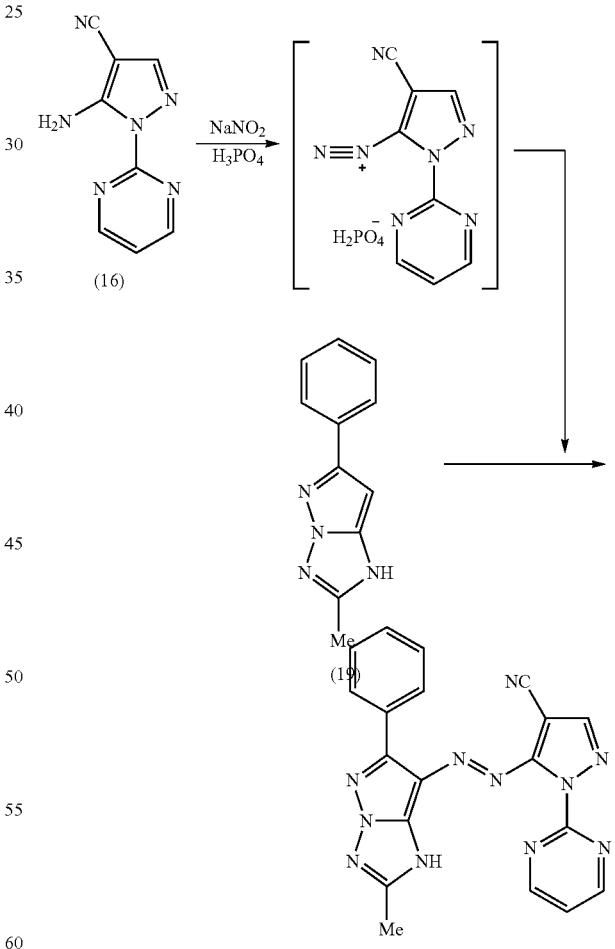

(2)-5

Synthesis of Pigment (2)-5

Figure 4:
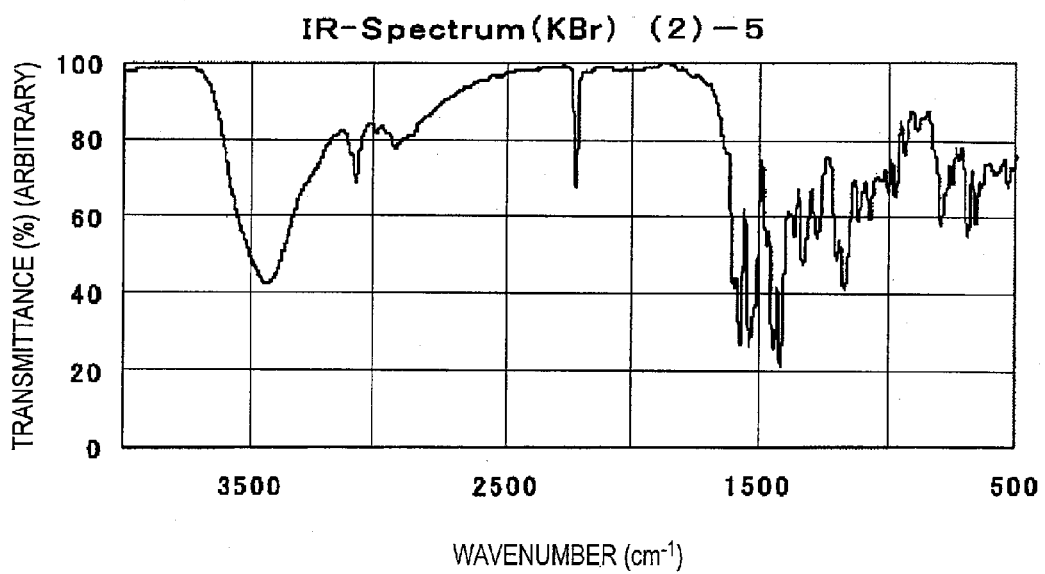
FIG. 4 is an infrared absorption spectrum of an illustrative compound (2)-5 of the azo pigment obtained in Example 5.

1.3 parts of compound (16) is added to 16 parts of phosphoric acid at room temperature, and the mixture is heated to an internal temperature of 60° C. to dissolve. This solution is cooled with ice and, while keeping the internal temperature at −5 to 0° C., 0.6 part of sodium nitrite is added thereto by portions, followed by stirring at the same temperature for 1 hour to obtain a diazonium salt solution. Separately, 1.2 parts of compound (19) is suspended in 60 parts of methanol to prepare a suspension, and the resulting suspension is cooled with ice to keep the internal temperature at 5° C. or lower. To this is gradually added the above-described diazonium salt solution in such manner that the internal temperature is kept at 5° C. or lower. After stirring the mixture at the same temperature for 1 hour, the ice bath is removed, followed by stirring the mixture for 1 hour at room temperature. Crystals precipitated are collected by filtration, and spray-washed with 50 parts of methanol, then sufficiently spray-washed with water. The thus-obtained crystals are added, without drying, to a mixture of 30 parts of methanol and 15 parts of water, and the mixture is heated to an internal temperature of 65° C. under stirring for 3 hours. Thereafter, the mixture is stirred for 1 hour under cooling in air and, after cooling to an internal temperature of room temperature, crystals precipitated are collected by filtration and washed with 30 parts of methanol. The crystals are dried for 12 hours at room temperature to obtain 1.6 parts of pigment (2)-5 of the invention. Yield: 69.1%. Infrared absorption spectrum (KBr method) of the pigment (2)-5 is shown in FIG. 4.

Example 6

Specific Illustrative Compound (2)-6

Specific illustrative compound (2)-6 is synthesized according to the following route.

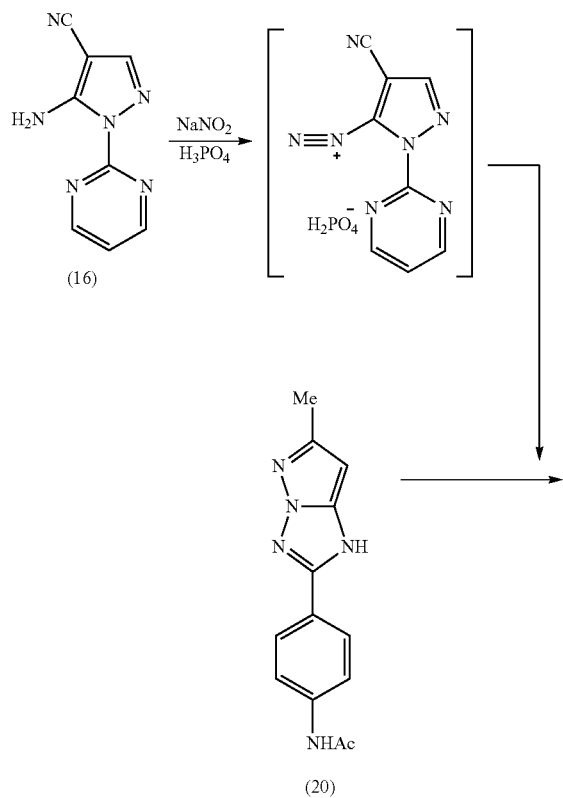

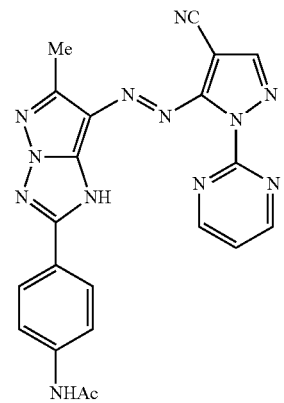

(2)-6

Synthesis of Pigment (2)-6

Figure 5:
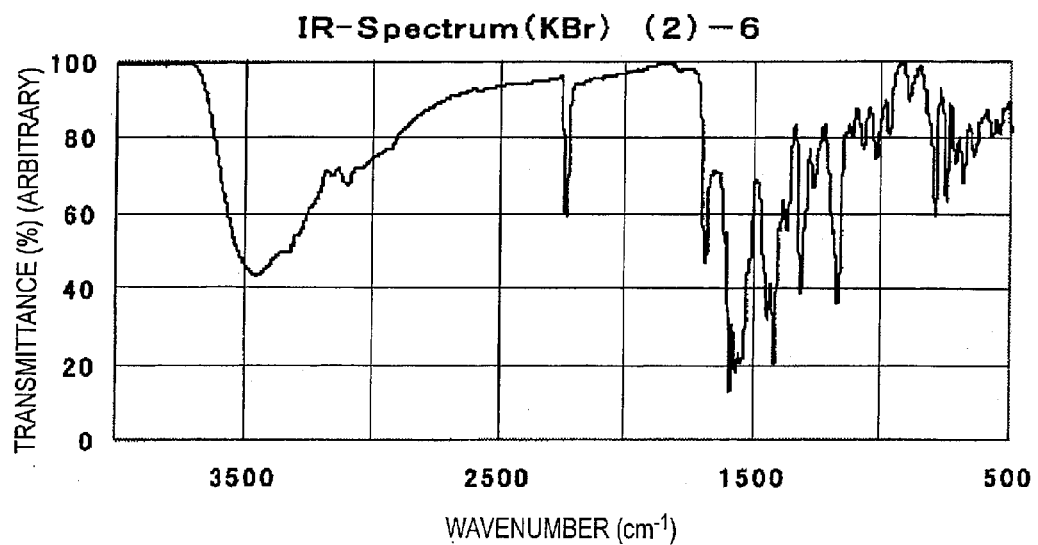
FIG. 5 is an infrared absorption spectrum of an illustrative compound (2)-6 of the azo pigment obtained in Example 6.

1.1 parts of compound (16) is added to 14 parts of phosphoric acid at room temperature, and the mixture is heated to an internal temperature of 60° C. to dissolve. This solution is cooled with ice and, while keeping the internal temperature at −5 to 0° C., 0.6 part of sodium nitrite is added thereto by portions, followed by stirring at the same temperature for 1 hour to obtain a diazonium salt solution. Separately, 1.4 parts of compound (20) is suspended in 70 parts of methanol to prepare a suspension, and the resulting suspension is cooled with ice to keep the internal temperature at 5° C. or lower. To this is gradually added the above-described diazonium salt solution in such manner that the internal temperature is kept at 5° C. or lower. After stirring the mixture at the same temperature for 1 hour, the ice bath is removed, followed by stirring the mixture for 1 hour at room temperature. Crystals precipitated are collected by filtration, and spray-washed with 50 parts of methanol, then sufficiently spray-washed with water. The thus-obtained crystals are added, without drying, to a mixture of 30 parts of methanol and 15 parts of water, and the mixture is heated to an internal temperature of 65° C. under stirring for 3 hours. Thereafter, the mixture is stirred for 1 hour under cooling in air and, after cooling to an internal temperature of room temperature, crystals precipitated are collected by filtration and washed with 30 parts of methanol. The crystals are dried for 12 hours at room temperature to obtain 0.7 part of pigment (2)-6 of the invention. Yield: 50.4%. Infrared absorption spectrum (KBr method) of the pigment (2)-6 is shown in FIG. 5.

Example 7

Specific Illustrative Compound (2)-7

Specific illustrative compound (2)-7 is synthesized according to the following route.

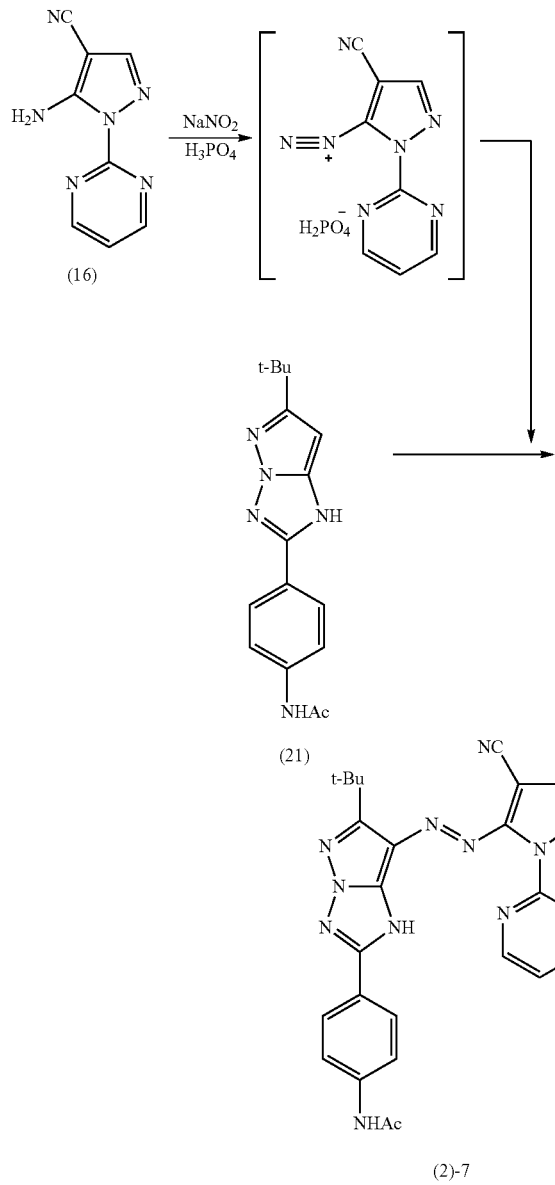

(2)-7

Synthesis of Pigment (2)-7

Figure 6:
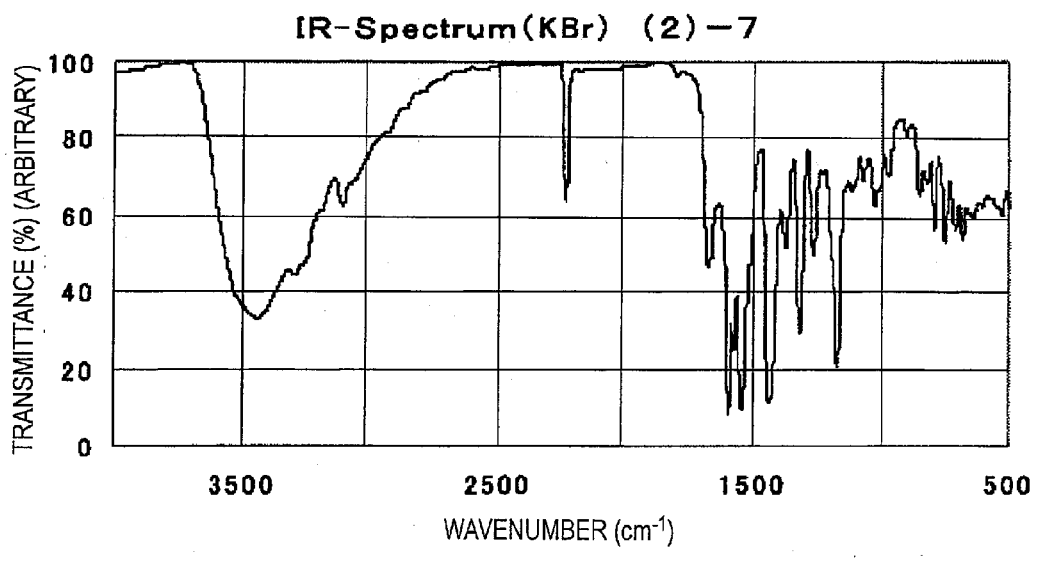
FIG. 6 is an infrared absorption spectrum of an illustrative compound (2)-7 of the azo pigment obtained in Example 7.

1.1 parts of compound (16) is added to 14 parts of phosphoric acid at room temperature, and the mixture is heated to an internal temperature of 60° C. to dissolve. This solution is cooled with ice and, while keeping the internal temperature at −5 to 0° C., 0.6 part of sodium nitrite is added thereto by portions, followed by stirring at the same temperature for 1 hour to obtain a diazonium salt solution. Separately, 1.5 parts of compound (21) is suspended in 60 parts of methanol to prepare a suspension, and the resulting suspension is cooled with ice to keep the internal temperature at 5° C. or lower. To this is gradually added the above-described diazonium salt solution in such manner that the internal temperature is kept at 5° C. or lower. After stirring the mixture at the same temperature for 1 hour, the ice bath is removed, followed by stirring the mixture for 1 hour at room temperature. Crystals precipitated are collected by filtration, and spray-washed with 50 parts of methanol, then sufficiently spray-washed with water. The thus-obtained crystals are added, without drying, to a mixture of 30 parts of methanol and 15 parts of water, and the mixture is heated to an internal temperature of 65° C. under stirring for 3 hours. Thereafter, the mixture is stirred for 1 hour under cooling in air and, after cooling to an internal temperature of room temperature, crystals precipitated are collected by filtration and washed with 30 parts of methanol. The crystals are dried for 12 hours at room temperature to obtain 1.5 parts of pigment (2)-7 of the invention. Yield: 60.0%. Infrared absorption spectrum (KBr method) of the pigment (2)-7 is shown in FIG. 6.

Example 8

Specific Illustrative Compound (2)-8

Specific illustrative compound (2)-8 is synthesized according to the following route.

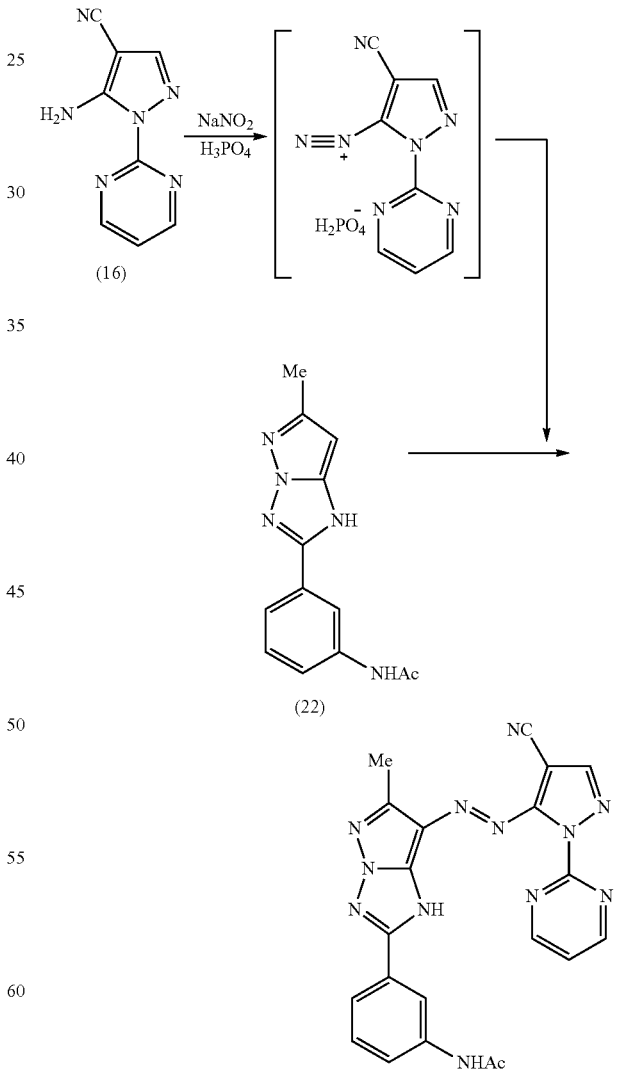

(2)-8

Synthesis of Pigment (2)-8

Figure 7:
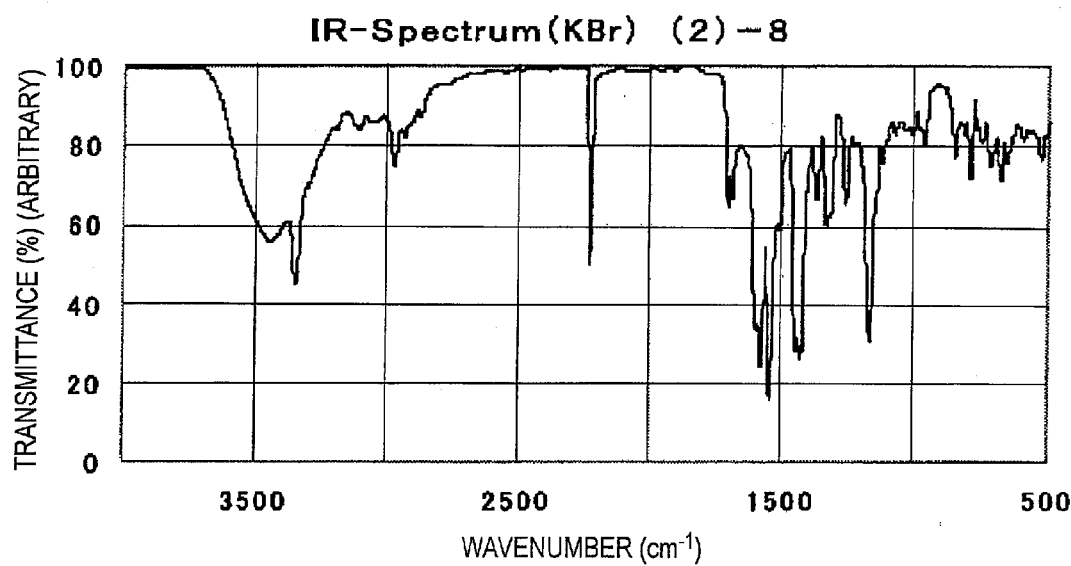
FIG. 7 is an infrared absorption spectrum of an illustrative compound (2)-8 of the azo pigment obtained in Example 8.

1.1 parts of compound (16) is added to 14 parts of phosphoric acid at room temperature, and the mixture is heated to an internal temperature of 60° C. to dissolve. This solution is cooled with ice and, while keeping the internal temperature at −5 to 0° C., 0.6 part of sodium nitrite is added thereto by portions, followed by stirring at the same temperature for 1 hour to obtain a diazonium salt solution. Separately, 1.4 parts of compound (22) is suspended in 60 parts of methanol to prepare a suspension, and the resulting suspension is cooled with ice to keep the internal temperature at 5° C. or lower. To this is gradually added the above-described diazonium salt solution in such manner that the internal temperature is kept at 5° C. or lower. After stirring the mixture at the same temperature for 1 hour, the ice bath is removed, followed by stirring the mixture for 1 hour at room temperature. Crystals precipitated are collected by filtration, and spray-washed with 50 parts of methanol, then sufficiently spray-washed with water. The thus-obtained crystals are added, without drying, to a mixture of 30 parts of methanol and 15 parts of water, and the mixture is heated to an internal temperature of 65° C. under stirring for 3 hours. Thereafter, the mixture is stirred for 1 hour under cooling in air and, after cooling to an internal temperature of room temperature, crystals precipitated are collected by filtration and washed with 30 parts of methanol. The crystals are dried for 12 hours at room temperature to obtain 1.8 parts of pigment (2)-8 of the invention. Yield: 75.2%. Infrared absorption spectrum (KBr method) of the pigment (2)-8 is shown in FIG. 7.

Example 9

Specific Illustrative Compound (2)-14

Specific illustrative compound (2)-14 is synthesized according to the following route.

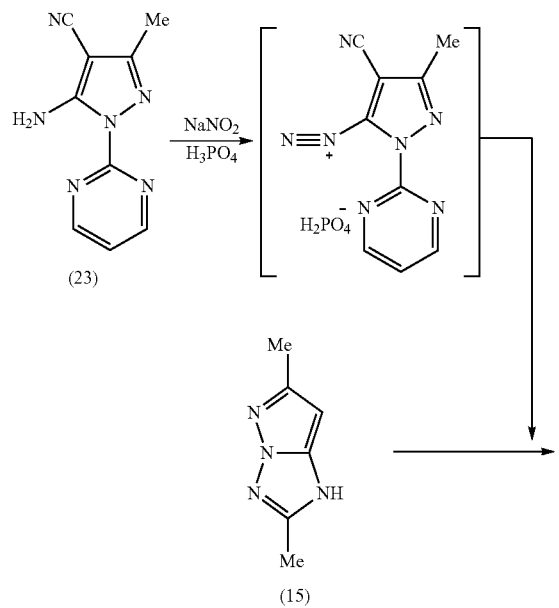

-continued

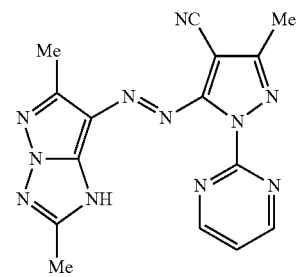

(2)-14

Synthesis of Pigment (2)-14

Figure 8:
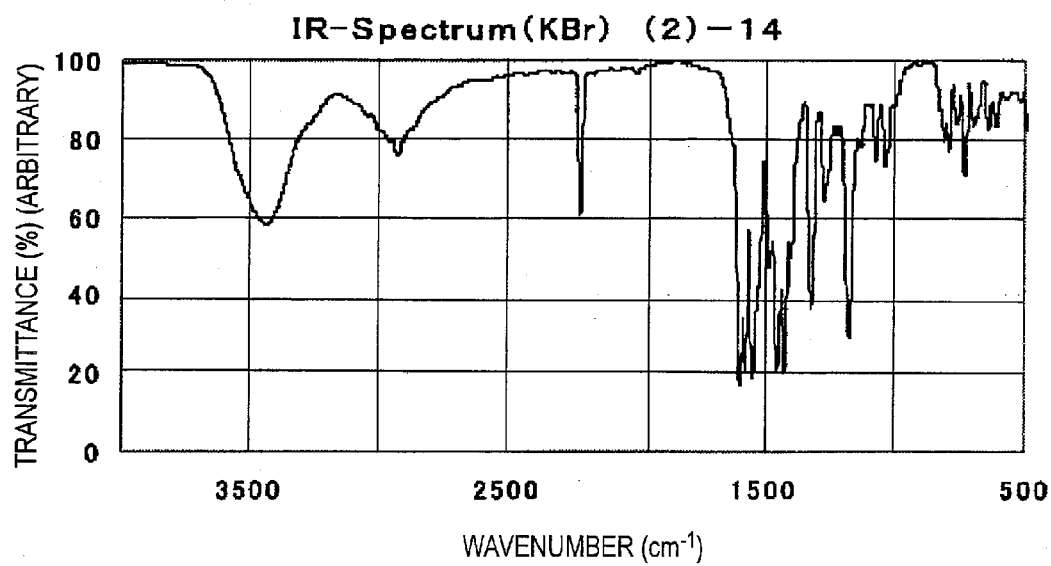
FIG. 8 is an infrared absorption spectrum of an illustrative compound (2)-14 of the azo pigment obtained in Example 9.

1.6 parts of compound (23) is added to 19.5 parts of phosphoric acid at room temperature, and the mixture is heated to an internal temperature of 60° C. to dissolve. This solution is cooled with ice and, while keeping the internal temperature at −5 to 0° C., 0.6 part of sodium nitrite is added thereto by portions, followed by stirring at the same temperature for 1 hour to obtain a diazonium salt solution. Separately, 1 part of compound (15) is suspended in 40 parts of methanol to prepare a suspension, and the resulting suspension is cooled with ice to keep the internal temperature at 5° C. or lower. To this is gradually added the above-described diazonium salt solution in such manner that the internal temperature is kept at 5° C. or lower. After stirring the mixture at the same temperature for 1 hour, the ice bath is removed, followed by stirring the mixture for 1 hour at room temperature. Crystals precipitated are collected by filtration, and spray-washed with 50 parts of methanol, then sufficiently spray-washed with water. The thus-obtained crystals are added, without drying, to a mixture of 30 parts of methanol and 15 parts of water, and the mixture is heated to an internal temperature of 65° C. under stirring for 3 hours. Thereafter, the mixture is stirred for 1 hour under cooling in air and, after cooling to an internal temperature of room temperature, crystals precipitated are collected by filtration and washed with 30 parts of methanol. The crystals are dried for 12 hours at room temperature to obtain 2.1 parts of pigment (2)-14 of the invention. Yield: 81.2%. Infrared absorption spectrum (KBr method) of the pigment (2)-14 is shown in FIG. 8.

Example 10

Specific Illustrative Compound (2)-21

Specific illustrative compound (2)-21 is synthesized according to the following route.

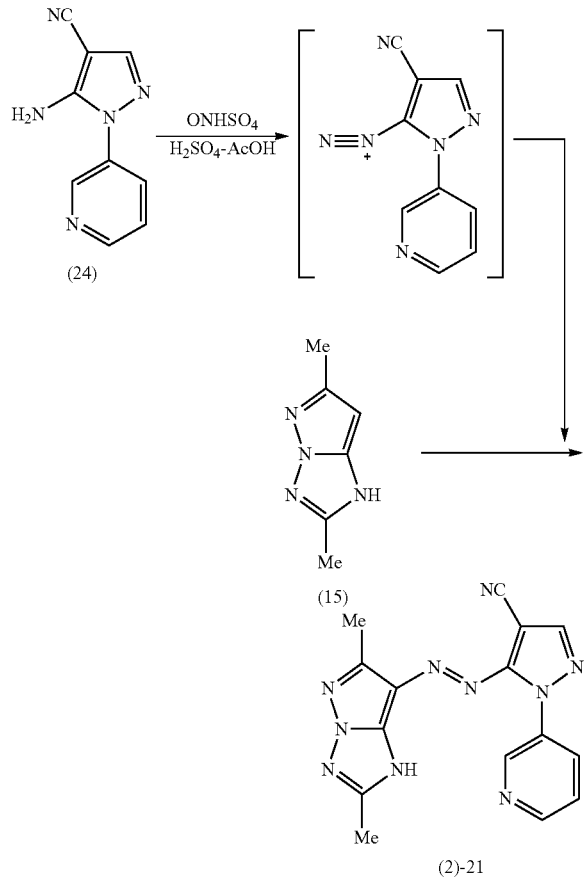

Synthesis of Pigment (2)-21

Figure 9:
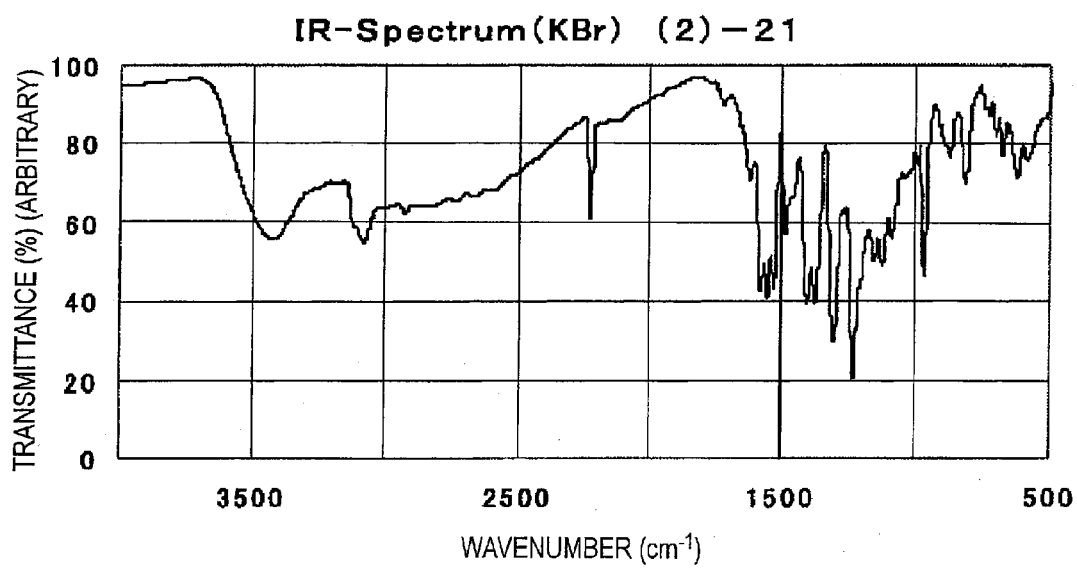
FIG. 9 is an infrared absorption spectrum of an illustrative compound (2)-21 of the azo pigment obtained in Example 10.

24 parts of concentrated sulfuric acid and 49 parts of acetic acid are cooled with ice, and 8.2 parts of compound (24) is added thereto by portions to dissolve in such manner that the internal temperature is kept at 10° C. or lower. The internal temperature of this solution is kept at 0 to 5° C., and 15.4 parts of 43% by weight nitrosylsulfuric acid is added thereto, followed by stirring at the same temperature for 1 hour to obtain a diazonium salt solution. Separately, 5 parts of compound (15) is added to 200 parts of methanol to prepare a suspension, and the resulting suspension is cooled with ice to keep the internal temperature at 5° C. or lower. To this is gradually added the above-described diazonium salt solution in such manner that the internal temperature is kept at 5° C. or lower. After stirring the mixture at the same temperature for 1 hour, the ice bath is removed, followed by stirring the mixture for 1 hour at room temperature. A solid product precipitated is collected by filtration, and spray-washed with 50 parts of methanol, then sufficiently spray-washed with water. The thus-obtained solid product is added, without drying, to a mixture of 50 parts of methanol and 25 parts of water, and the mixture is heated to an internal temperature of 65° C. under stirring for 3 hours. Thereafter, the mixture is stirred for 1 hour under cooling in air and, after cooling to an internal temperature of room temperature, crystals precipitated are collected by filtration and washed with 30 parts of methanol. The crystals are dried for 12 hours at room temperature to obtain 6.5 parts of pigment (2)-21 of the invention. Yield: 53.1%. Infrared absorption spectrum (KBr method) of the pigment (2)-21 is shown in FIG. 9.

Example 11

Specific Illustrative Compound (1)-41

Specific illustrative compound (1)-41 is synthesized according to the following route.

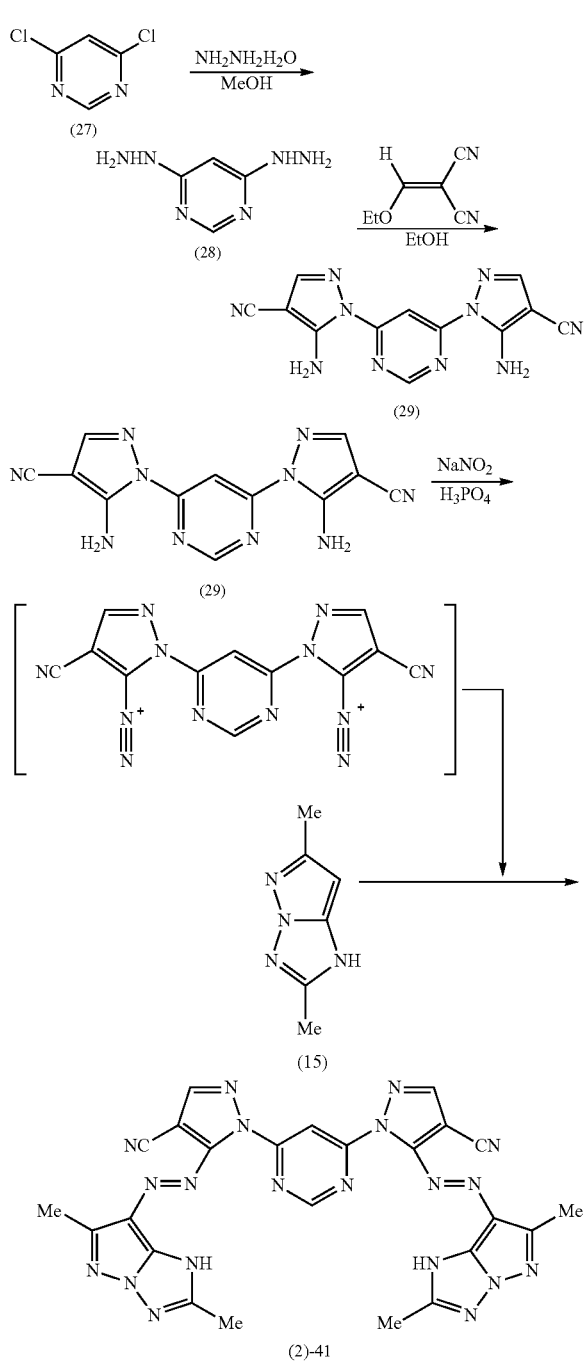

Synthesis of Intermediate (28)

298 mL of methanol is added to 387 mL (7.98 mol) of hydrazine monohydrate, and the mixture is cooled to 10° C.

(internal temperature). To this mixed solution is gradually added 149 g (1.00 mol) of 4,6-dichloropyrimidine (at an internal temperature of 20° C. or lower), then the ice bath is removed to increase the temperature to room temperature, followed by stirring at the same temperature for 30 minutes. Thereafter, the mixture is further heated to an internal temperature of 60° C., and is stirred at the same temperature for 5 hours. After completion of the reaction, 750 ml of water is added thereto, and then the mixture is cooled to an internal temperature of 8° C. with ice. Crystals precipitated are collected by filtration, spray-washed with water, then spray-washed with isopropanol. The crystals are dried at room temperature for 36 hours to obtain 119 g (white powder; yield: 84.5%) of the intermediate (28). Results of NMR measurement of the thus-obtained intermediate (28) are as follows. $^1$H-NMR (300 MHz, d-DMSO) 7.80 (s, 1H), 7.52 (s, 2H), 5.98 (s, 1H), 4.13 (s, 4H)

Synthesis of Intermediate (29)

50 mL of ethanol is added to 10 g (71.3 mmol) of the intermediate (28), followed by stirring at room temperature. To the resulting suspension is added 21.8 g (178 mmol) of ethoxymethylenemalononitrile and, after dropwise adding thereto a 12M hydrochloric acid aqueous solution at the same temperature so as to adjust the pH of the mixture to 3. Then, the mixture is heated to an internal temperature of 80° C., followed by stirring at the same temperature for 1.5 hours. After completion of the reaction, the mixture is cooled to room temperature, and crystals precipitated are collected by filtration, and spray-washed with 30 ml of water and 30 ml of isopropanol. The thus-obtained crystals are dried at 60° C. under reduced pressure to obtain 18.8 g (gray powder; yield: 90.3%) of the foregoing intermediate (29).

Results of NMR measurement of the thus-obtained intermediate (29) are as follows. $^1$H-NMR (300 MHz, d-DMSO) 8.94 (s, 1H), 8.35 (s, 4H), 8.03 (s, 2H), 8.01 (s, 1H)

Synthesis of Pigment (1)-41

Figure 10:
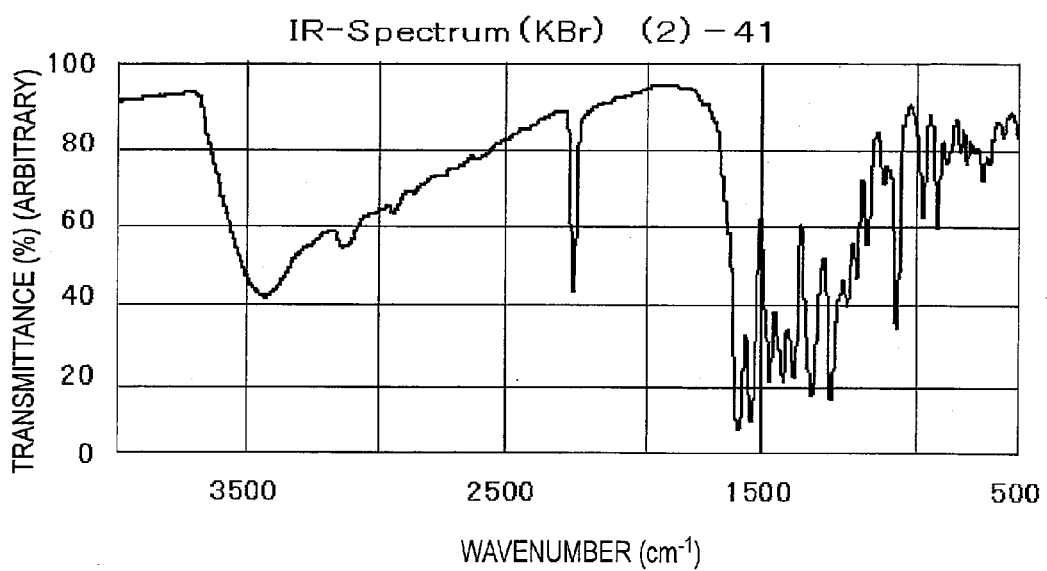
FIG. 10 is an infrared absorption spectrum of an illustrative compound (2)-41 of the azo pigment obtained in Example 11.

40 parts of phosphoric acid and 10 parts of sulfuric acid are added to 2 parts of the intermediate (29), and the mixture is heated to an internal temperature of 60° C., followed by stirring for 30 minutes. This suspension is cooled and, while keeping the internal temperature at 3 to 5° C., 1.2 parts of sodium nitrite is added thereto, followed by stirring at the same temperature for 2 hours to obtain a diazonium salt solution. To this is gradually added compound (15) as a powder in such manner that the internal temperature is kept at 5° C. or lower. After stirring the mixture at the same temperature for 1.5 hours, the ice bath is removed, followed by stirring the mixture for 30 minutes at room temperature. 60 parts of methanol is added to this mixture and, after stirring for 30 minutes, this reaction solution is poured into 200 parts of water, followed by stirring at room temperature for 30 minutes. Crystals precipitated are collected by filtration, and spray-washed with 100 parts of water and 50 parts of methanol. The thus-obtained crystals are added, without drying, to a mixture of 20 parts of methanol and 20 parts of water, and the mixture is heated to an internal temperature of 65° C. under stirring for 3 hours. Thereafter, the mixture is stirred for 1 hour under cooling in air and, after cooling to an internal temperature of room temperature, crystals precipitated are collected by filtration and washed with 30 parts of methanol. The crystals are dried for 12 hours at room temperature to obtain 3.1 parts of pigment (1)-41 of the invention. Yield: 77.3% Infrared absorption spectrum (KBr method) of the pigment (1)-41 is shown in FIG. 10.

Comparative Example 1

Comparative Compound (25)

Comparative compound (25) is synthesized according to the following route.

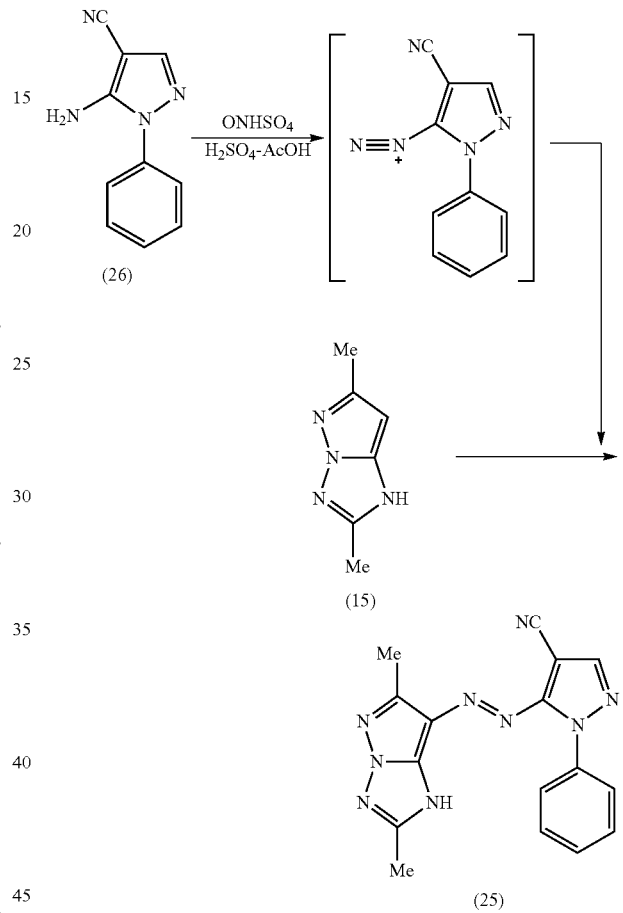

Synthesis of Comparative Compound (25)

Figure 11:
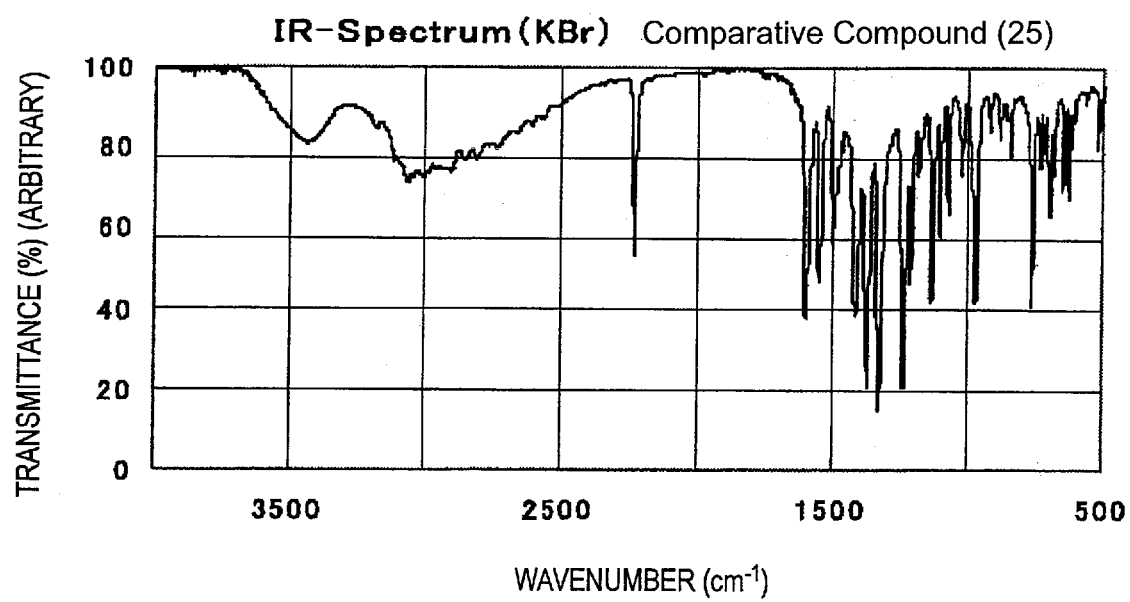
FIG. 11 is an infrared absorption spectrum of an illustrative compound (25) of the azo pigment obtained in Comparative Example 1.

2.7 parts of 40% by weight nitrosylsulfuric acid is dissolved in 3.9 parts of concentrated sulfuric acid and 17.2 parts of acetic acid at room temperature to dissolve. This solution is cooled with ice to keep the internal temperature thereof at 0 to 5° C., and 1.4 parts of compound (26) is added by portions in such manner that the internal temperature is kept at 5° C. or lower, followed by stirring at the same temperature for 1 hour to obtain a diazonium salt solution. Separately, 1 part of compound (15) is added to 40 parts of methanol to prepare a suspension, and the resulting suspension is cooled with ice to keep the internal temperature at 5° C. or lower. To this is gradually added the above-described diazonium salt solution in such manner that the internal temperature is kept at 5° C. or lower. After stirring the mixture at the same temperature for 1 hour, the ice bath is removed, followed by stirring the mixture for 1 hour at room temperature. Crystals precipitated are collected by filtration, and spray-washed with 50 parts of methanol, then sufficiently spray-washed with water. The thus-obtained crystals are added, without drying, to a mixture of 50 parts of methanol and 25 parts of water, and the mixture is heated to an internal temperature of 65° C. under stirring for 3 hours. Thereafter, the mixture is stirred for 1 hour under cooling in air and, after cooling to an internal temperature of room temperature, crystals precipitated are collected by filtration and washed with 30 parts of methanol. The crystals are dried for 12 hours at room temperature to obtain 1.8 parts of comparative compound (25). Yield: 75.3%. Infrared absorption spectrum (KBr method) of the pigment (25) is shown in FIG. 11.

Example 12

2.5 parts of the pigment (2)-1 synthesized in Example 2, 0.5 part of sodium oleate, 5 parts of glycerin, and 42 parts of water are mixed, and the resulting mixture is subjected to dispersing procedure together with 100 parts of 0.1-mm diameter zirconia beads for 6 hours at 300 rpm in a planetary ball mill. After completion of the dispersing procedure, the zirconia beads are removed to obtain a yellow pigment dispersion 1.

Example 13

2.5 parts of the pigment (2)-2 synthesized in Example 3, 0.5 part of sodium oleate, 5 parts of glycerin, and 42 parts of water are mixed, and the resulting mixture is subjected to dispersing procedure together with 100 parts of 0.1-mm diameter zirconia beads for 6 hours at 300 rpm in a planetary ball mill. After completion of the dispersing procedure, the zirconia beads are removed to obtain a yellow pigment dispersion 2.

Example 14

2.5 parts of the pigment (2)-3 synthesized in Example 4, 0.5 part of sodium oleate, 5 parts of glycerin, and 42 parts of water are mixed, and the resulting mixture is subjected to dispersing procedure together with 100 parts of 0.1-mm diameter zirconia beads for 6 hours at 300 rpm in a planetary ball mill. After completion of the dispersing procedure, the zirconia beads are removed to obtain a yellow pigment dispersion 3.

Example 15

2.5 parts of the pigment (2)-5 synthesized in Example 5, 0.5 part of sodium oleate, 5 parts of glycerin, and 42 parts of water are mixed, and the resulting mixture is subjected to dispersing procedure together with 100 parts of 0.1-mm diameter zirconia beads for 6 hours at 300 rpm in a planetary ball mill. After completion of the dispersing procedure, the zirconia beads are removed to obtain a yellow pigment dispersion 4.

Example 16

2.5 parts of the pigment (2)-6 synthesized in Example 6, 0.5 part of sodium oleate, 5 parts of glycerin, and 42 parts of water are mixed, and the resulting mixture is subjected to dispersing procedure together with 100 parts of 0.1-mm diameter zirconia beads for 6 hours at 300 rpm in a planetary ball mill. After completion of the dispersing procedure, the zirconia beads are removed to obtain a yellow pigment dispersion 5.

Example 17

2.5 parts of the pigment (2)-7 synthesized in Example 7, 0.5 part of sodium oleate, 5 parts of glycerin, and 42 parts of water are mixed, and the resulting mixture is subjected to dispersing procedure together with 100 parts of 0.1-mm diameter zirconia beads for 6 hours at 300 rpm in a planetary ball mill. After completion of the dispersing procedure, the zirconia beads are removed to obtain a yellow pigment dispersion 6.

Example 18

2.5 parts of the pigment (2)-8 synthesized in Example 8, 0.5 part of sodium oleate, 5 parts of glycerin, and 42 parts of water are mixed, and the resulting mixture is subjected to dispersing procedure together with 100 parts of 0.1-mm diameter zirconia beads for 6 hours at 300 rpm in a planetary ball mill. After completion of the dispersing procedure, the zirconia beads are removed to obtain a yellow pigment dispersion 7.

Example 19

2.5 parts of the pigment (1)-41 synthesized in Example 11, 0.5 part of sodium oleate, 5 parts of glycerin, and 42 parts of water are mixed, and the resulting mixture is subjected to dispersing procedure together with 100 parts of 0.1-mm diameter zirconia beads for 6 hours at 300 rpm in a planetary ball mill. After completion of the dispersing procedure, the zirconia beads are removed to obtain a yellow pigment dispersion 8.

Comparative Example 2

The same procedures as described in Example 12 are conducted except for using the comparative compound (25) in place of the pigment (2)-1 used in Example 12. After dispersing procedure for 6 hours, a pigment dispersion cannot be obtained, it is gelated.

Comparative Example 3

The same procedures as described in Example 12 are conducted except for using C.I. Pigment Yellow 128 (CROMOPHTAL YELLOW 8GN; manufactured by CIBA Specialty Chemicals) in place of the pigment (2)-1 used in Example 12.

Comparative Example 4

The same procedures as described in Example 12 are conducted except for using C.I. Pigment Yellow 74 (Iralite YELLOW GO; manufactured by CIBA Specialty Chemicals) in place of the pigment (2)-1 used in Example 12.

Comparative Example 5

The same procedures as described in Example 12 are conducted except for using C.I. Pigment Yellow 155 (INKJET YELLOW 4G VP2532; manufactured by Clariant Co.) in place of the pigment (2)-1 used in Example 12.
<Evaluation of Light Fastness>

Each of the pigment dispersions obtained is coated on a photo mat paper manufactured by Seiko Epson Corporation by using a No. 3 bar coater. Image density of each of the thus-obtained coated products is measured by means of a reflection densitometer (X-Rite 938; manufactured by X-Rite Co.), and a coated product having an image density of 1.0 is irradiated with xenon light (170000 Lux; in the presence of a cut filter which cuts light having a wavelength of 325 nm or less) for 14 days using a fade meter. Image density before and after irradiation with xenon light is measured using the reflection densitometer, and the pigment dispersions 1, 3, 4, 6, 8, and comparative pigment dispersions 1 to 3 are evaluated in terms of colorant residual ratio [(density after irradiation/density before irradiation)×100%] according to the following criteria: samples with a colorant residual ratio of 90% or more are ranked A; samples with a colorant residual ratio of 70% or more and less than 90% are ranked B; and samples with a colorant residual ratio of less than 70% are ranked C. The results are shown in Table 1.

Each of the thus-obtained pigment dispersions is coated on plain paper 4024 manufactured by Xerox Corporation using a No. 3 bar coater. When each of the coated products is subjected to evaluation of light fastness in the same manner as with the photo mat paper, there are obtained similar results.

<Dispersibility>

2.5 parts of the pigment, 0.5 part of sodium oleate, 5 parts of glycerin, and 42 parts of water are mixed, and the resulting mixture is subjected to dispersing procedure together with 100 parts of 0.1-mm diameter zirconia beads for 6 hours at 300 rpm in a planetary ball mill. After the dispersing procedure, dispersibility of each of the pigment dispersions 1, 3, 4, 6, 8, and comparative pigment dispersions 1 to 3 is evaluated according to the following criteria: samples which can be dispersed with a sufficiently small particle size without gelation are ranked A; and samples which can not be dispersed in such manner are ranked B. The results are shown in Table 1.

TABLE 1

|  | Light Fastness (Photo Mat Paper) | Light Fastness (Plain Paper) | Dispersibility |
|---|---|---|---|
| Pigment dispersion 1 | A | A | A |
| Pigment dispersion 3 | A | A | A |
| Pigment dispersion 4 | A | A | A |
| Pigment dispersion 6 | A | A | A |
| Pigment dispersion 8 | A | A | A |
| Comparative compound (25) | — | — | B |
| Comparative pigment dispersion 1 | B | B | A |
| Comparative pigment dispersion 2 | C | C | A |
| Comparative pigment dispersion | C | C | A |

From the results of Table 1, it is seen that the pigment dispersions using the pigments of the invention show excellent light fastness and excellent dispersibility.

INDUSTRIAL APPLICABILITY

According to the present invention, there can be provided an azo compound and an azo pigment showing excellent coloring characteristics such as tinctorial strength and hue and showing excellent fastness such as light fastness and ozone fastness, a dispersion containing the azo compound or azo pigment, a coloring composition, ink for inkjet recording, an ink tank for inkjet recording using the ink, an inkjet recording method, and a recorded product having the above-described excellent coloring characteristics and fastness.

Although the invention has been described in detail and by reference to specific embodiments, it is apparent to those skilled in the art that it is possible to add various alterations and modifications insofar as the alterations and modifications do not deviate from the spirit and the scope of the invention.

This application is based on a Japanese patent application filed on Mar. 7, 2008 (Japanese Patent Application No. 2008-58712) and a Japanese patent application filed on Dec. 26, 2008 (Japanese Patent Application No. 2008-334956), and the contents thereof are incorporated herein by reference.

The invention claimed is:

1. An azo pigment represented by the general formula (1), a tautomer, salt, or hydrate thereof:

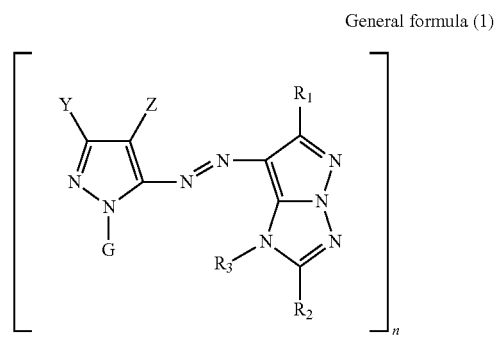

General formula (1)

wherein $R_1$, $R_2$, $R_3$, Y, Z, and G each independently represents a hydrogen atom or a substituent;

n represents an integer of from 2 to 4;

when n=2, the general formula (1) represents a dimer formed through $R_1$, $R_2$, $R_3$, Y, Z, or G;

when n=3, the general formula (1) represents a trimer formed through $R_1$, $R_2$, $R_3$, Y, Z, or G; and when n=4, the general formula (1) represents a tetramer formed through $R_1$, $R_2$, $R_3$, Y, Z, or G.

2. An azo pigment represented by the following general formula (2), a tautomer, salt, or hydrate thereof:

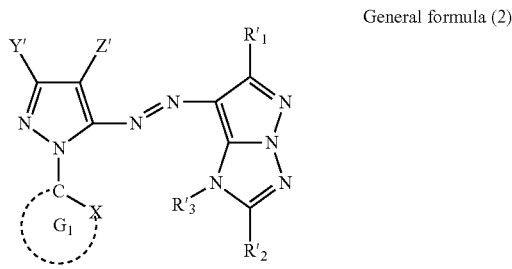

General formula (2)

wherein $R'_1$, $R'_2$, and Y' each independently represents a hydrogen atom, a straight or branched alkyl group containing from 1 to 4 carbon atoms, an alkenyl group containing from 2 to 4 carbon atoms, an alkynyl group containing from 2 to 4 carbon atoms, an acyl group containing from 1 to 5 carbon atoms, an aralkyl group containing from 7 to 9 carbon atoms, a 5- to 8-membered, saturated or unsaturated hydrocarbon ring group, or a 5- to 8-membered, saturated or unsaturated heterocyclic group;

$R'_3$ represents a hydrogen atom or a monovalent substituent;

Z' represents an electron-withdrawing group having a Hammett σp value of 0.2 or more;

X represents a hetero atom adjacent to the carbon atom;

$G_1$ represents atoms necessary for forming a 5- to 8-membered, saturated or unsaturated heterocyclic ring;

when any one of $R'_1$, $R'_2$, Y', and $G_1$ represents a 5- to 8-membered, saturated or unsaturated heterocyclic ring, it represents a monocyclic ring or a condensed ring; and when any one of $R'_1$, $R'_2$, $R'_3$, Y', and $G_1$ represents a 5-membered unsaturated heterocyclic ring, it has two or more nitrogen atoms within the ring.

3. The azo pigment, tautomer, salt or hydrate according to claim 2, wherein X in the general formula (2) is a nitrogen atom.

4. The azo pigment, tautomer, salt or hydrate according to claim 2, wherein $G_1$ in the general formula (1) is selected from the substituent group represented by the following general formulae (3)-1 to (3)-6:

General formula (3)

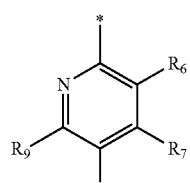
(3)-1

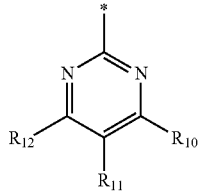
(3)-2

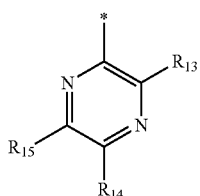
(3)-3

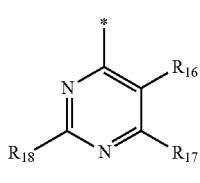
(3)-4

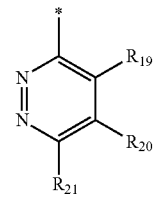
(3)-5

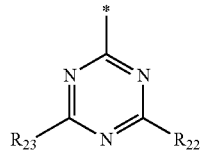
(3)-6 wherein $R_6$ to $R_{23}$ each independently represents a hydrogen atom or a substituent; and $R_6$ to $R_{21}$ may be connected to each other to form a ring.

5. The azo pigment, tautomer, salt or hydrate according to claim 1, wherein the azo pigment represented by the general formula (1) is an azo pigment represented by the following general formula (4):

General formula (4)

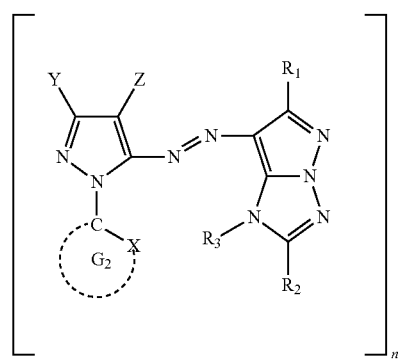

wherein n, $R_1$, $R_2$, $R_3$, Y, and Z are respectively the same as defined for n, $R_1$, $R_2$, $R_3$, Y, and Z in the general formula (1);

X represents a hetero atom adjacent to the carbon atom;

$G_2$ represents atoms necessary for forming a 5- to 8-membered, saturated or unsaturated heterocyclic ring;

when n=2, the general formula (4) represents a dimer formed through $R_1$, $R_2$, $R_3$, Y, Z, or $G_2$;

when n=3, the general formula (4) represents a trimer formed through $R_1$, $R_2$, $R_3$, Y, Z, or $G_2$;

when n=4, the general formula (4) represents a tetramer formed through $R_1$, $R_2$, $R_3$, Y, Z, or $G_2$; and when any one of $R_1$, $R_2$, $R_3$, Y and $G_2$ represents a 5- to 8-membered, saturated or unsaturated heterocyclic ring, it represents a monocyclic ring or a condensed ring.

6. The azo pigment, tautomer, salt or hydrate according to claim 5, wherein X in the general formula (4) is a nitrogen atom.

7. The azo pigment, tautomer, salt or hydrate according to claim 5, wherein $G_2$ in the general formula (4) is a group selected from the substituent group represented by the following general formulae (3)-1 to (3)-6:

General formula (3)

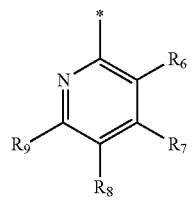
(3)-1

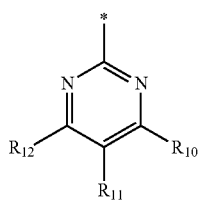
(3)-2

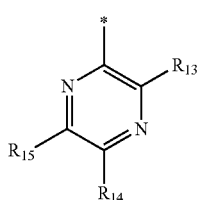
(3)-3

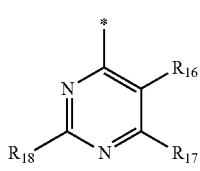
(3)-4

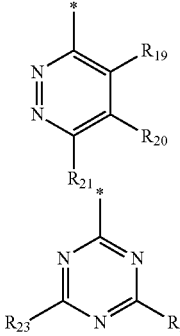
(3)-5

(3)-6 wherein $R_6$ to $R_{23}$ each independently represents a hydrogen atom or a substituent; and
$R_6$ to $R_{21}$ may be connected to each other to form a ring.

8. An azo compound represented by the following general formula (2):

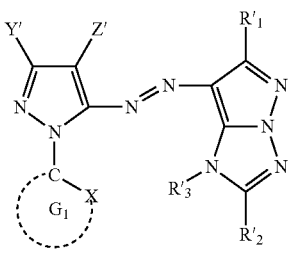

General formula (2)

wherein $R'_1$, $R'_2$, and Y' each independently represents a hydrogen atom, a straight or branched alkyl group containing from 1 to 4 carbon atoms, an alkenyl group containing from 2 to 4 carbon atoms, an alkynyl group containing from 2 to 4 carbon atoms, an acyl group containing from 1 to 5 carbon atoms, an aralkyl group containing from 7 to 9 carbon atoms, a 5- to 8-membered, saturated or unsaturated hydrocarbon ring group, or a 5- to 8-membered, saturated or unsaturated heterocyclic group;

$R'_3$ represents a hydrogen atom or a monovalent substituent;

Z' represents an electron-withdrawing group having a Hammett σp value of 0.2 or more;

X represents a hetero atom adjacent to the carbon atom;

$G_1$ represents atoms necessary for forming a 5- to 8-membered, saturated or unsaturated heterocyclic ring;

when any one of $R'_1$, $R'_2$, Y', and $G_1$ represents a 5- to 8-membered, saturated or unsaturated heterocyclic ring, it represents a monocyclic ring or a condensed ring; and when any one of $R'_1$, $R'_2$, $R'_3$, Y', and $G_1$ represents a 5-membered unsaturated heterocyclic ring, it has two or more nitrogen atoms within the ring.

9. The azo compound according to claim 8,
wherein $G_1$ in the general formula (2) is selected from the substituent group represented by the following general formulae (3)-1 to (3)-6:

General formula (3)

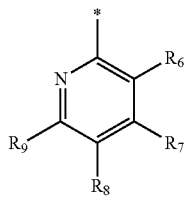
(3)-1

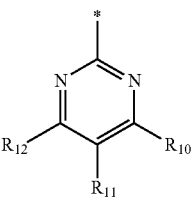
(3)-2

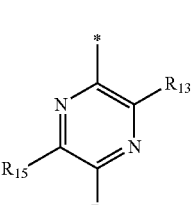
(3)-3

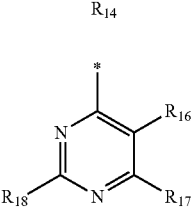
(3)-4

(3)-5

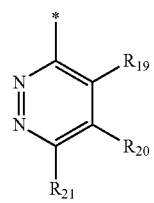

(3)-6

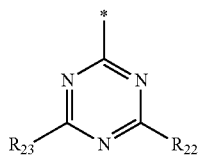

wherein $R_6$ to $R_{23}$ each independently represents a hydrogen atom or a substituent, and $R_6$ to $R_{21}$ may be connected to each other to form a ring.

10. An azo compound represented by the following general formula (4):

General formula (4)

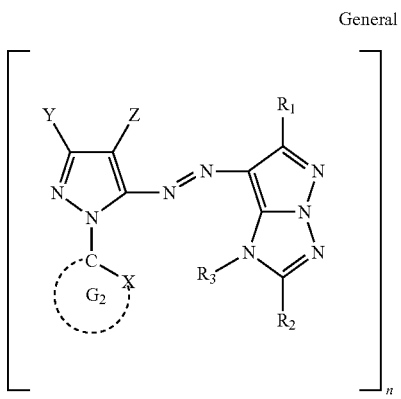

wherein $R_1$, $R_2$, $R_3$, Y, and Z each independently represents a hydrogen atom or a substituent;

n represents an integer of 2 to 4;

X represents a hetero atom adjacent to the carbon atom, $G_2$ represents atoms necessary for forming a 5- to 8-membered, saturated or unsaturated heterocyclic ring;

when n=2, the general formula (4) represents a dimer formed through $R_1$, $R_2$, $R_3$, Y, Z, or $G_2$;

when n=3, the general formula (4) represents a trimer formed through $R_1$, $R_2$, $R_3$, Y, Z, or $G_2$;

when n=4, the general formula (4) represents a tetramer formed through $R_1$, $R_2$, $R_3$, Y, Z, or $G_2$; and when any one of $R_1$, $R_2$, $R_3$, Y, Z and $G_2$ represents a 5- to 8-membered, saturated or unsaturated heterocyclic ring, it represents a monocyclic ring or a condensed ring.

11. The azo compound according to claim 10;

wherein $G_2$ in the general formula (4) is a group selected from the substituent group represented by the following general formulae (3)-1 to (3)-6:

General formula (3)

(3)-1

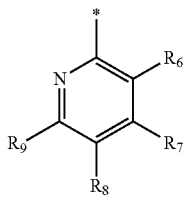

(3)-2

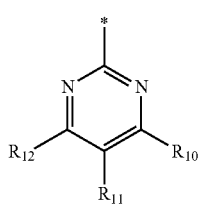

(3)-3

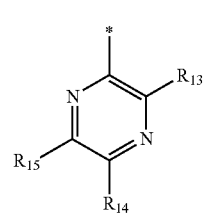

(3)-4

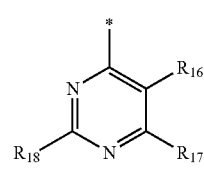

(3)-5

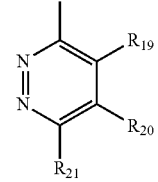

(3)-6

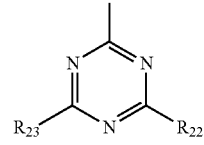

wherein $R_6$ to $R_{23}$ each independently represents a hydrogen atom or a substituent, and $R_6$ to $R_{21}$ may be connected to each other to form a ring.

12. A dispersion which comprises at least one of the azo pigments described in claim 1, the tautomers, salts, and hydrates thereof or at least one of the azo compounds described in claim 8.

13. A coloring composition, which comprises the dispersion recited in claim 12.

14. An ink for inkjet recording, which contains the dispersion recited in claim 12.

15. An ink tank for inkjet recording, which comprises the ink for inkjet recording recited in claim 14.

16. An inkjet recording method comprising using the ink for inkjet recording recited in claim 14.

17. A recorded product obtained by using the ink for inkjet recording recited in claim 14.

18. The azo pigment, tautomer, salt or hydrate according to claim 6, wherein $G_2$ in the general formula (4) is a group selected from the substituent group represented by the following general formulae (3)-1 to (3)-6:
General formula (3)
(3)-1
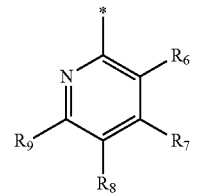
(3)-2
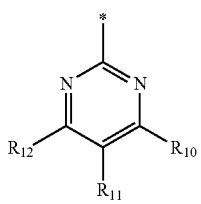
(3)-3
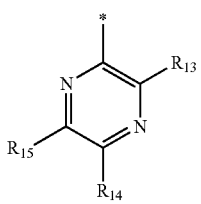
-continued
(3)-4
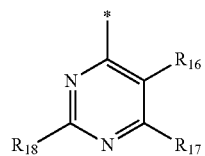
(3)-5
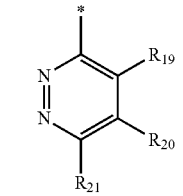
(3)-6
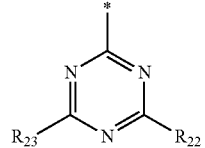
wherein $R_6$ to $R_{23}$ each independently represents a hydrogen atom or a substituent; and
$R_6$ to $R_{21}$ may be connected to each other to form a ring.
* * * * *